(12) United States Patent
Kwagh et al.

(10) Patent No.: US 6,515,120 B1
(45) Date of Patent: Feb. 4, 2003

(54) METHOD FOR SEQUENCING AND CHARACTERIZING POLYMERIC BIOMOLECULES USING APTAMERS AND A METHOD FOR PRODUCING APTAMERS

(75) Inventors: Jae-Gyu Kwagh, Fairless Hills, PA (US); John J. Macklin, Wenonah, NJ (US); Paul G. Mitsis, Trenton, NJ (US); Kevin M. Ulmer, Cohasset, MA (US)

(73) Assignee: Praelux Incorporated, Lawrenceville, NJ (US)

( * ) Notice: Subject to any disclaimer, the term of this patent is extended or adjusted under 35 U.S.C. 154(b) by 0 days.

(21) Appl. No.: 09/578,634

(22) Filed: May 25, 2000

Related U.S. Application Data

(60) Provisional application No. 60/135,863, filed on May 25, 1999.

(51) Int. Cl.[7] .................. C07H 21/00; C07H 21/02; C07H 21/04; C12Q 1/68; C12P 19/34
(52) U.S. Cl. .................. 536/25.4; 435/6; 435/91.1; 536/23.1; 536/24.2; 536/24.3; 536/24.31; 536/24.32
(58) Field of Search .................. 435/6, 91.1, 91.5; 536/23.1, 24.3, 24.31, 24.33, 25.3

(56) References Cited

U.S. PATENT DOCUMENTS

| | | |
|---|---|---|
| 4,962,037 A | 10/1990 | Jett et al. |
| 5,270,163 A | 12/1993 | Gold et al. |
| 5,322,796 A | 6/1994 | Ishikawa |
| 5,528,046 A | 6/1996 | Ishikawa |
| 5,582,981 A | 12/1996 | Toole et al. |
| 5,631,146 A | 5/1997 | Szostak et al. |
| 5,674,743 A | 10/1997 | Ulmer |
| 5,753,454 A | 5/1998 | Lee |
| 5,776,674 A | 7/1998 | Ulmer |

FOREIGN PATENT DOCUMENTS

| | | |
|---|---|---|
| WO | WO 89//03432 | 4/1989 |
| WO | WO 94/18218 | 8/1994 |
| WO | WO 98/45700 | 10/1998 |

OTHER PUBLICATIONS

Molecular Cloning, A Laboratory Manual Sambrook et al. 1989 Cold Spring Harbor pp. 13.2–13.81. Laboratory Press.*

Famulok, M., "Molecular Recognition of Amino Acids by RNA–aptamers: an L–Citrulline Binding RNA Motif and its Evolution into an L–arginine Binder." *J. Amer. Chem. Soc.*, 116, pp. 1698–1706, (1994).

Xu, W., et al., "Anti–peptide Aptamers Recognize Amino Acid Sequence and Bind a Protein Epitope." *Proc. Natl. Acad. Sci*, 93, pp. 7475–7478, (1996).

Database EMBL: accession No. AC005081. Published Jun. 15, 1998, Sulston and Waterson: "Homo sapiens BAC clone CTA–270D13 from 7q11.2–q22, complete sequence" XP002182386.

Gregory J. Connell, et al., "RNAs with Dual Specificity and Dual RNAs with Similar Specificity," *Science*, 264, pp. 1137–1141 (1994).

Bruce E. Eaton, et al., "Post SELEX Combinational Optimization of Aptamers," *Bioorganic & Medicinal Chemistry*, 5(6), pp. 1087–1096 (1997).

C.J. Edge, et al., "Fast Sequencing of Oligosaccharides: The Reagent–Array Analysis Method,"*Proc. Natl. Acad. Sci*, 89, pp. 6338–6342 (1992).

Albert Geiger et al., "RNA Aptamers that Bind–L–Arginine with Sub–Micromolar Dissociation Constants and High Enantioselectivity," *Nucleic Acids Research*, 24(6), pp. 1029–1036 (1996).

Igor German, et al., "Aptamers as Ligands in Affinity Probe Capillary Electrophoresis," *Anal. Chem.*, pp. 4540–4545 (1998).

Aurelia A. Haller, et al., "*In vitro* Selection of a 7–Methyl–Guanosine Binding RNA That Inhibits Translation of Capped mRNA Molecules," *Proc. Natl. Acad. Sci*, 94 pp. 8521–8526 (1997).

Thomas Hermann, et al., "Adaptive Recognition by Nucleic Acid Aptamers," *Science*, 287, pp. 820–825 (2000).

David E. Huizenga, et al., "A DNA Aptamer That Binds Adenosine and ATP," *Biochemistry*, 34, pp. 656–665 (1995).

Daisuke Kiga, et al., "An RNA Aptamer to the Xanthine/ Guanine Base with a Distinctive Mode of Purine Recognition," *Nucleic Acids Res.*, 26, pp. 1755–60 (1998).

Makoto Koizumi, et al., "Allosteric Selection of Ribozymes that Respond to the Second Messengers cGMP and cAMP", *Nature Structural Biology*, 6(11), pp. 1062–1071 (1999).

Charles T. Lauhon., et al., "RNA Aptamers That Bind Flavin and Nicotinamide Redox Cofactors," *J. Am. Chem. Soc.*, 117, pp. 1246–1257 (1995).

(List continued on next page.)

*Primary Examiner*—Sean McGarry
*Assistant Examiner*—Jane Zara
(74) *Attorney, Agent, or Firm*—Fish & Neave; James F. Haley, Jr.

(57) ABSTRACT

The present invention relates to methods for sequencing a polymeric biomolecule and methods for structurally characterizing the same comprising using aptamers. In a preferred embodiment of this invention, these methods relate to using the single polymeric biomolecule. The invention also relates to a method for selecting aptamers useful for sequencing nucleic acids and aptamers generated by the method. The invention also provides aptamers that recognize and bind to AMP, dAMP, GMP, dGMP, CMP and dCMP.

15 Claims, 28 Drawing Sheets

OTHER PUBLICATIONS

Sally Prime, et al., "Exoglycosidase Sequencing of N–linked Glucans by the Reagent Array Analysis Method(RAAM)," *Methods in Molecular Biology: Glycoanalysis Protocols*, 2nd Ed., Hounsell, E., ed., 76, pp. 53–69 (1998).

Stacia M. Rink, et al., "Creation of RNA Molecules That Recognize The Oxidative Lesion 7,8–Dihydro–8–Hydroxy–2'–Deoxyguanosine (8–oxodG) in DNA," *Proc. Natl. Acad. Sci*, 95, pp. 11619–11624 (1998).

Mandana Sassanfar, et al., "An RNA Motif That Binds ATP," *Nature*, 364, pp. 550–553 (1993).

Mark L. Stolowitz, "Chemical Protein Sequencing and Amino Acid Analysis," *Current Opinion in Biotechnology*, 4, pp. 9–13 (1993).

Craig Tuerk, et al., "Systemic Evolution of Ligands of Exponential Enrichment: RNA Ligands of Bacteriophage T4 DNA Polymerase," *Science*, 249, pp. 505–510 (1990).

\* cited by examiner

FIG. 4

(a) dAMP-aptamer clones:

```
dA20   ggcaagcttgggcctcatgtcgaaGGCGGTCAGTCGCCGCTGC         GGA CGG A GGAGG T ACGG G GGAG A gagcaatggcgatgacggatcctca         2X
dA7'   ggcaagcttgggcctcatgtcgaaGGCGGTCAGTCGCCGCTGC         GGA CGG A GGAGG T ACGG G GGAG   gagcaatggcgatgacggatcctca
dA3'   ggcaagcttgggcctcatgtcgaaGGCGGCCAGTCGCCGCTGC         GGA CGG A GGAGG Y ACGG G GGAG G gagcaatggcgatgacggatcctca         4X
dA13'       ggcaagcttggcctcatgtcgaaCCTACT                  GGA CGG A GGAGG A ACGG G GGAG GGAAGTAGGTGAGGgagcaatggcgatgacggatcctca
dA19         ggcaagcttgggcctcatgtcgaaAGCCATG GCGGGGGA       ATG CGG G ACGG A GGAG   CATCGGTGgagcaatggcgatgacggatcctca
dA12'        ggcaagcttgggcctcatgtcgaaAGCCATG GCGGGGGAG      ATG CGG G GGTGG C GGAG A CATCGGTGgagcaatggcgatgacggatcctca dA21   ggcaagcttgggcctcatgtcgaaGCGGAAGGTACAGTCAGAAGTAGTT GCGGGGGAG   GCA CGG A GGAGG T ACGG A GGAG TGCACGGAGgagcaatggcgatgacggatcctca   11X
dA18   ggcaagcttgggcctcatgtcgaaGCGGAAGGTACAGTCAGAAGTNGTT GCGGGGGAG   ATG CGG A GGAGG T ACGG A GGAG TGCACGGAGgagcaatggcgatgacggatcctca
dA4    ggcaagcttgggcctcatgtcgaaGCGGAAGGTACAGTCAGAAGTAGTT GCGGGGGAG   GGCA CGG A GGAGG T ACGG A GGAG TGCACGGAGgagcaatggcgatgacggatcctca   2X
dA6    ggcaagcttgggcctcatgtcgaaGCGGAAGGTACAGTCAGAAGTAGTT GCGGGGGAG   GGTA CGG A GGAGG T ACGG A GGAG TGCACGGAGgagcaatggcgatgacggatcctca
dA12   ggcaagcttgggcctcatgtcgaaGCGGAAGGTACAGTCAGAAGTAGTT GCGGGGGAG   AGCA CGG A GGAGG T ACGG A GGAG TGCACGGAGgagcaatggcgatgacggatcctca
dA9'   ggcaagcttgggcctcatgtcgaaGAAGGAGCACGAAATCGGCAATCA GCGGGGGAG    AGCA CGG G GGGAGG T ACGG A GGAG WGCACGGAGgagcaatggcgatgacggatcctca
dA9    ggcaagcttgggcctcatgtcgaaGCCCGAGTGAGGTTAACGCCAG GCGGGGGAG      GCGA CGG A GGAGG T ACGG A GGAG TGCACGGAGgagcaatggcgatgacggatcctca
dA13   ggcaagcttgggcctcatgtcgaaGCTGAGCGGAGAGTAATCGCTGT GCGGGGGAG     GCGA CGG A GGAGG T ACGG A GGAG TGCACGGAGgagcaatggcgatgacggatcctca
dA33   ggcaagcttgggcctcatgtcgaaGGTGAGCGGGGTCAGAGTGGAGCCGT GCGGGGGAG  GGCA CGG A GGAGG T ACGG A GGAG TGCACGGAGgagcaatggcgatgacggatcctca   2X
dA28   ggcaagcttgggcctcatgtcgaaGGAAGCCGAGAGGATTGGCATCGT GCGGGGGAG    GCA CGG A GGAGG T ACGG A GGAG TGCACGGAGgagcaatggcgatgacggatcctca
dA17   ggcaagcttgggcctcatgtcgaaCAAGTATGGGAACGCGAGCGTT GTGGGGGAG      GCA CGG T ACGG A GGAG TGCACGGAGgagcaatggcgatgacggatcctca
dA23   ggcaagcttgggcctcatgtcgaaGGTGGCGGGTCAGAGTGGAGCBGT GCGNGNSAG    GGCA CGG T ACGG A GGAG TGCACGGAGgagcaatggcgatgacggatcctca
dA22   ggcaagcttgggcctcatgtcgaaGGAAGTGTGGAGTCAAATGTAW CGGGAGNGNCCG   CGG G GGAGG G ACGG A GGAG TGCACGGAGgagcaatggcgatgacggatcctca
dA31   ggcaagcttggcctcaaGTTGGCACCGTAGCCCATGGGT CGGAGAGCGGGCG         GCG CGG G GGAAG G ACGG G GGAG CGGCGTGGGGgagcaatgcgatgacggatcctca
dA1    ggcaagcttggcctcatgtcgaaTGAGACGGCATC GGGAGACGGCATC             GCG CGG G GGAAG A ATGG A GGAG CGCCCCGGgagcaatgcgatgacggatcctca
dA14'  ggcaagcttggcctcatgtcgaaTGAGACGGTT GGGAGACGGCATC               GCG CGG G GGAAG A GGAG CAATTGCGGGAAGTATGGAGgagcaatgcgatgacggatcctca
```

(b) Abridged dAMP-aptamers:

```
dA34.100  tcatgtcgaaGCGGAAGGTATAGTCAGAAGTAGTTG    CGG G ACGG C GGAGG G GGAG GTACGAGGAGGAGTGTACGGAGgagcaatgcgatgacggatcctca
dA20.77    tcatgtcgaaGCGGTCAGTCCGCCGCTGCGA       CGG A GGAGG T ACGG G GGAG Agagcaatgcgatgacggatcctca
dA19.81         tcatgtcgaaAGCCATGGCGGGGATG         CGG G ACGG A GGAG   CATCGGTGgagcaatgcgatgacggatcctca
dA13'.91   ggcaagcttggcctcatgtcgaaCCTACTGGA       CGG A ACGG A GGAG GGAAGTAGGTGAGGgagcaatgcgatgacggatcctca
dA19.30                     GAGATG              CGG G ACGG A GGAG CATCG
dA19.43    AGCCATGGCGGGGGAGATGCCTAGCATCGGTGACCAATGGCG
dA13'.58           gcctcatgtcgaaCCTACTGGA        CGG A GGAGG A ACGG G GGAG GGAAGTAGGTGAGgag
dA13'.51                gcctcacCTACTGGA           CGG A GGAGG A ACGG G GGAG GGAAGTAGGTGAGGgag
dA13'.37              CCTACTGGA                  CGG A GGAGG A ACGG G GGAG GGAAGTAGG
```

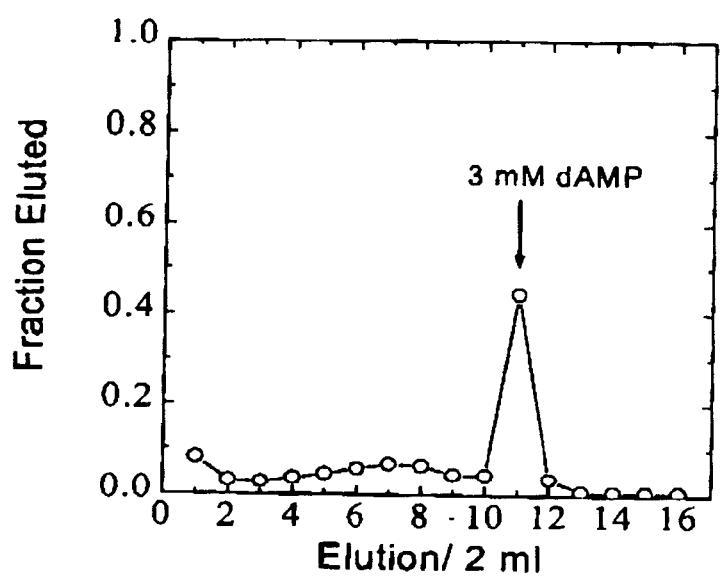
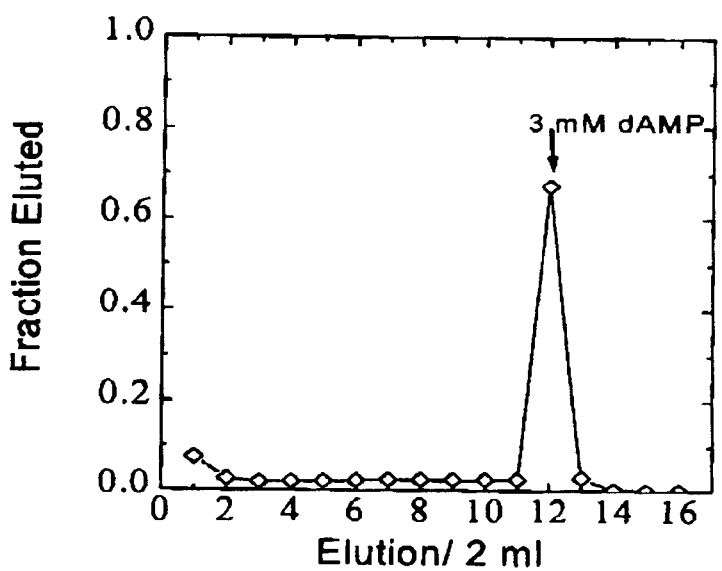
FIG. 8

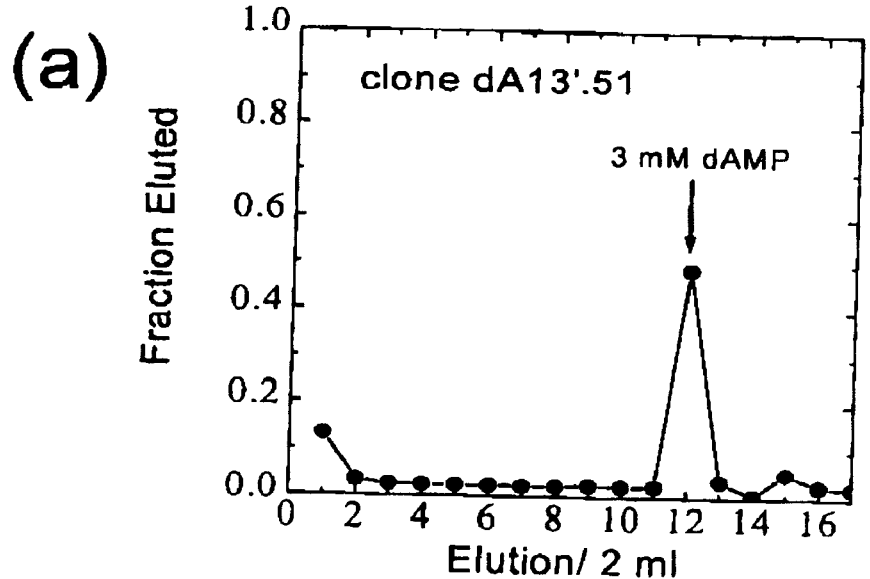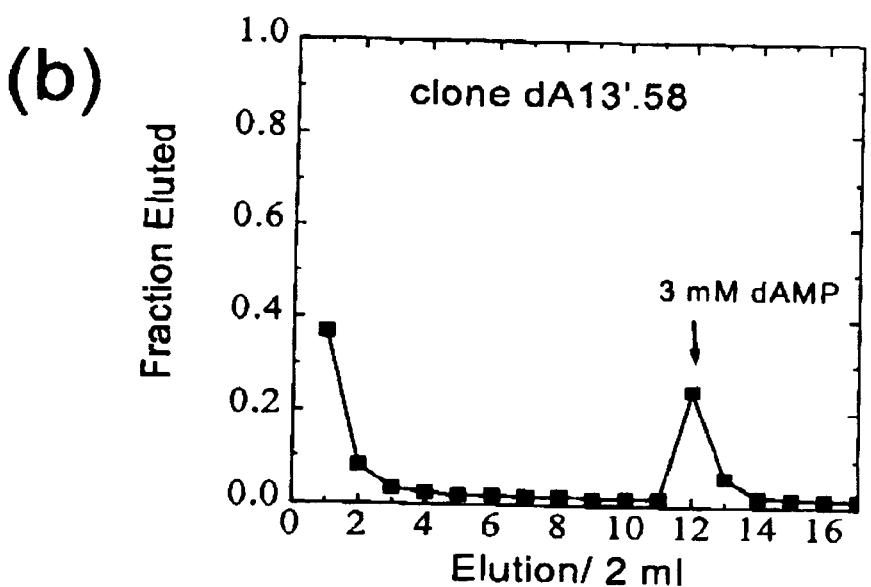
FIG. 11

(a) dGMP-aptamer clones

```
dG17              ggcaagcttgggcctcatgtcgaaGTGACACCAC                  TGGG T TGGG TA TGGG T AGGGT TGTGAATCACgagcaatggcgatgacgacggatcctca      8X
dG20              ggcaagcttgggcctcatgtcgaaGTGACACCAC                  TGGG T TGGG TA DGGG T AGGKT GTGGAATCACgagcaatggcgatgacgacggatcctca
dG26              ggcaagcttgggcctcatgtcgaaGTGACACCAC                  TGGG T TGGG TA NGGG T AGGGT TGTGGAATCACgagcaatggcgatgacgacggatcctca
dG5               ggcaagcttgggcctcatgtcgaaGTGACACCAC                  TGGG T TGGG T YGGG T AGGGT TGTGGAATCACgagcaatggcgatgacgacggatcctca     2X
dG7               ggcaagcttgggcctcatgtcgaaGTGACACCAC                  TGGG T TGGG T NGGG T AGGGT TGTGGAATCACgagcaatggcgatgacgacggatcctca     2X
dG4               ggcaagcttgggcctcatgtcgaaGCTATGCAGATCGCCATAAG        TGGG T TGGG CA TGGG A AGGGT Ggagcaatggcgatgacggatcctca                   4X
dG32              ggcaagcttgggcctcatgtcgaaGCTACGCAAATCGCCACAAG        TGGAGT TGGG AC TGGG AGMAAGGT Ggagcaatggcgatgacgacggatcctca
dG14              ggcaagcttgggcctcatgtcgaaTCAGGCAGCGCTGCGATT          TGGG C TGGG AA TGGG A AGGGT TAgagcaatggcgatgacgacgatcctca                 2X
dG29              ggcaagcttgggcctcatgtcgaaCCGGCATCGTTAGTGTAA          TGGG C TGGG CA TGGG TTAGGGT GAgagcaatggcgatgacgacgatcctca                2X
dG8               ggcaagcttgggcctcatgtcgaaGCATGGCCACATTGGGAA          TGGG C TGGG AA TGGG T AGGGT TCgagcaatggcgatgacgacgatcctca
dG21              ggcaagcttgggcctcatgtcgaaGTCGTCGCCGATGTCTCGG         TGGG G TGGG TA TGGG T AGGGT AACgagcaatggcgatgacggatcctca
dG36              ggcaagcttgggcctcatgtcgaagCCGAA                      TGGG C TGGG AA TGGTGT AGGGT TTTCGGCTATGTCCgagcaatggcgatgacggatcctca
dG3                   ggcaagcttgggcctcatgtcgaagTAGG                   TGGG A TGGG CA TGGG G AGGGT GGCTACTGGAACGTGAgagcaatggcgatgacggatcctca
dG35                  ggcaagcttgggcctcatgtcgaaTACAG                   TGGGTGTAGGG AA TGNN T GGGT TAWTATTTGTGTTTgagcaatggcgatgacggatcctca
dG37                    ggcaagcttgggcctcatgtcgaaCGGCagTgTCC             GGG T TGGG CB                 GGGaaGGBaNGGTCGCCTGgagcaatggcgatgacggatcctca
dG15                    ggcaagcttgggcctcatgtcgaaGGGGTTATGCA             TGGG CGTGGG AA TGG                  CCGACAAGGAGCCCCgagcaatggcgatgacggatcctca
dG19                    ggcaagcttgggcctcatgtcgaaGGGGGCGTA               TGAAATCTGGG TG CGGG G GGAT GAGCCGATACgagcaatggcgatgacggatcctca
```

(b) Abridged dGMP-aptamers

```
dG17.44                                 agGTGACACCAC TGGG T TGGG TA TGGG T AGGGT TGTGAATCAC
dG17.44.g                               agGTGACACCAC TGGG G TGGG TA TGGG T AGGGT TGTGAATCAC
dG4.48                         AGATCGCCATAAG TGGG T TGGG CA TGGG A AGGGT Ggagcaatggcgat
dG21.52             GTCGTGCCGATGTCTCGG TGGG G TGGG TA TGGG T AGGGT AACgagcaatggc
dG15.42                    aGGGGTATGCA TGGG CGTGGG AA TGG CCGACAAGGAGCCCC
```

FIG. 15

(a) CMP-aptamer clones

```
C3     ggcaagcttgggcctcatgtcgaaGGGGCGTATG GGC      TTTG GGGAG GGT TTC GG C G ACA   TG TCCTCAgagcaatggcgatgacggatcctca  11x
C10    ggcaagcttgggcctcatgtcgaaGGGGCGTATG GGC      TTTG GGGAG GGT TTC GG C G ACA   TG ATGTCgagcaatggcgatgacggatcctca
C30    ggcaagcttgggcctcatgtcgaaGGGGCGTATG GGC      TTTG GGGAG GGT TTC GG C G ACA   TG GTGCCgagcaatggcgatgacggatcctca
C9     ggcaagcttgggcctcatgtcgaaTCCATTGATCCGC GGC    AGTGC GGGAG GGT GGA GG T G TGCT TGgagcaatgcgatgacgatcctca          4x
C25    ggcaagcttgggcctcatgtcgaaTCCATTGATCCGC GGC    AGTGC GGGAG GGT AGA GG T G TGCT TGgagcaatgcgatgacgatcctca          2x
C12    ggcaagcttgggcctcatgtcgaaGCTTAACTAGGGT CGC    CATGC GGGAG GGT AGA GG T G TGCT TGgagcaatgcgatgacgatcctca          2x
C8     ggcaagcttgggcctcatgtcgaaGGTGACGTGTATT GGC    AGTGC GGGAGTGGT AGA GG T G TGCT TGgagcaatggcgatgacggatcctca
C32    ggcaagcttgggcctcatgtcgaaTCCATTGATCCGCGC      AGTGC SGGAG GGT ARA GG T G TGCT TGgagcaatggcgatgacggatcctca
C29          ggcaagcttgggcctcatgtcgaaG GGAGT GGGAG GGT TGA GG G G TGCT TG GAACGGCTGCGACACAgagcaatggcgatgacggatcctca  2x
C6           ggcaagcttgggcctcatgtcgaaG GGAGT GGGAGGGGT TGA GG G G TGCT TG GAACGACTGCGACACAgagcaatggcgatgacggatcctca
C1           ggcaagcttgggcctcatgtcgaaGGCGTATA GGGAGCGGGT  AC    GG T G               GAAGGGGTTAGCCTACATgagcaatggcgatgacggatcctca  3x C38    ggcaagcttgggcctcatgtcgaaGGTGGGCGTATGAAATCTG  GGT GCG GG G G TA    TG ACCTTATACgagcaatggcgatgacggatcctca
C21    ggcaagcttgggcctcatgtcgaaGGTGGGCGTATGAAATCTG  GGT GCG GG G G GA    TG AGCCGATACgagcaatggcgatgacggatcctca
C17    ggcaagcttgggcctcatgtcgaaGGTGGGCGTATGAAATCTG  GGT GCG GG G G TA    TG AGCCGATACgagcaatggcgatgacggatcctca
C5     ggcaagcttgggcctcatgtcgaaGGTGGGCGTATGAAATCTG  GGT GCG GG G G        TRKCCCCTTGKRGgagcaatggcgatgacggatcctca
C2     ggcaagcttgggcctcatgtcgaaGGGTGGGCTAGGCATAGTGAACA  GGT AGG GG C G ACTAGGGACgagcaatggcgatgacggatcctca           2x
```

(b) Abridged CMP-aptamers

```
C3.48        tcatgtcgaaGGGGCGTATGGGCTTTG GGGAG GGT TTC GG C G ACATGT
C9.58        TGATCCGGGCAGTGC GGGAG GGT GGA GG T G TGCTTGgagcaatggcgatgacggatc
```

FIG. 23

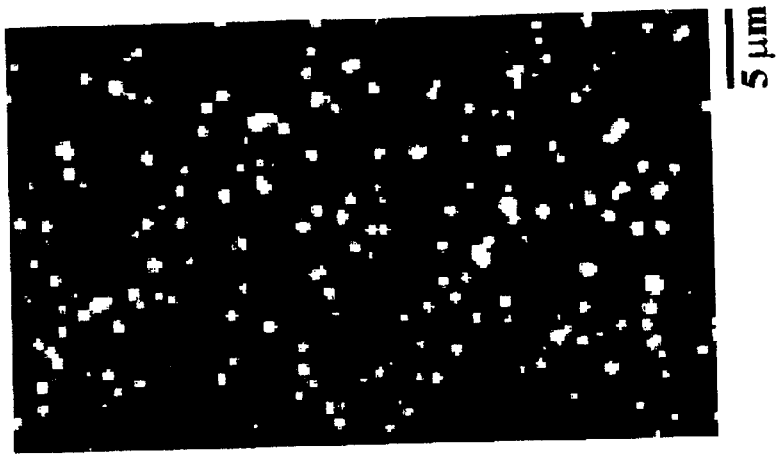
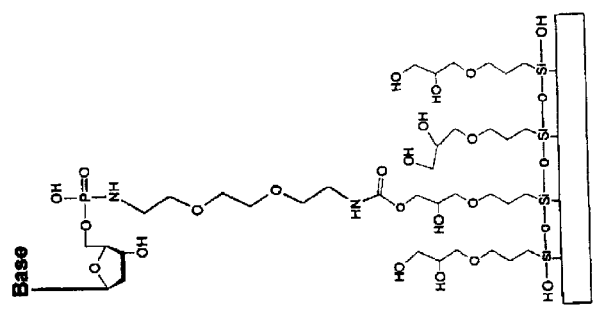
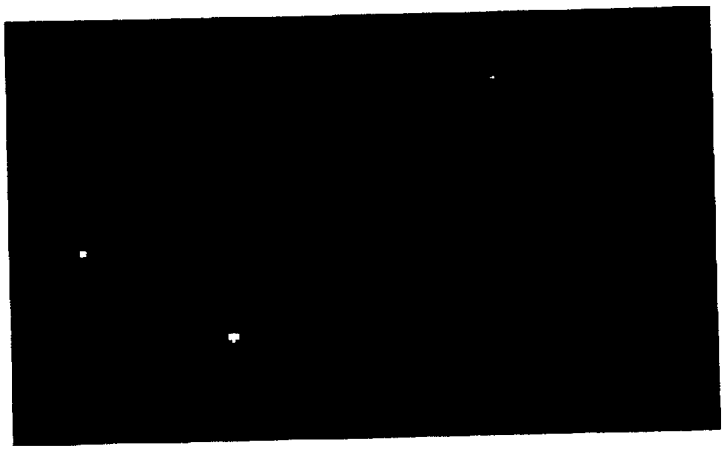
Figure 28

SEQUENCE LISTING

```
<160> NUMBER OF SEQ ID NOS: 90

<210> SEQ ID NO 1
<211> LENGTH: 19
<212> TYPE: DNA
<213> ORGANISM: Artificial Sequence
<220> FEATURE:
<221> NAME/KEY: misc_feature
<222> LOCATION: 1...19
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 1
cggrggaggn acggrggag                                                  19

<210> SEQ ID NO 2
<211> LENGTH: 15
<212> TYPE: DNA
<213> ORGANISM: Artificial Sequence
<220> FEATURE:
```

```
<221> NAME/KEY: misc_feature
<222> LOCATION: 1...15
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 2
gggagggtnn nggng                                                      15

<210> SEQ ID NO 3
<211> LENGTH: 10
<212> TYPE: DNA
<213> ORGANISM: Artificial Sequence
<220> FEATURE:
<221> NAME/KEY: misc_feature
<222> LOCATION: 1...10
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 3 ggtnnnggng                                                            10

<210> SEQ ID NO 4
<211> LENGTH: 21
<212> TYPE: DNA
<213> ORGANISM: Artificial Sequence
<220> FEATURE:
<221> NAME/KEY: misc_feature
<222> LOCATION: 1...21
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 4
tgggntgggn ntgggnaggg t                                               21

<210> SEQ ID NO 5
<211> LENGTH: 91
<212> TYPE: DNA
<213> ORGANISM: Artificial Sequence
<220> FEATURE:
<221> NAME/KEY: misc_feature
<222> LOCATION: 1...91
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 5
ggcaagcttg ggcctcatgt cgaannnnnn nnnnnnnnnn nnnnnnnnnn nnnnnnnnnn      60
nnnnnngagc aatggcgatg acggatcctc a                                    91

<210> SEQ ID NO 6
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 6
ggcaagcttg ggcctcatgt cgaaggcggt cagtcgccgc tgcggacgga ggaggtacgg      60
gggagagagc aatggcgatg acggatcctc a                                    91
```

```
<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 7
ggcaagcttg ggcctcatgt cgaaggcggt cagtcgccgc tgcggacgga ggaggtacgg      60
gggaggagca atggcgatga cggatcctca                                      90

<210> SEQ ID NO 8
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 8
ggcaagcttg ggcctcatgt cgaaggcggc cagtcgccgc tgcggacgga ggaggyacgg      60
gggagggagc aatggcgatg acggatcctc a                                    91

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 9
ggcaagcttg ggcctcatgt cgaacctact ggacggagga ggaacggggg agggagtagg      60
tgagggagca atggcgatga cggatcctca                                      90

<210> SEQ ID NO 10
<211> LENGTH: 94
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 10
ggcaagcttg ggcctcatgt cgaaagccat ggcgggggaa tgcgggggag gcacggagga      60
gcatcggtgg agcaatggcg atgacggatc ctca                                 94

<210> SEQ ID NO 11
<211> LENGTH: 95
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 11
ggcaagcttg ggcctcatgt cgaaagccat ggcgggggag atgcgggggt ggcacggagg      60
agcatcggtg gagcaatggc gatgacggat cctca                                95

<210> SEQ ID NO 12
<211> LENGTH: 114
<212> TYPE: DNA
<213> ORGANISM: Artificial Sequence
```

<220> FEATURE:
<223> OTHER INFORMATION: Description of Artificial Sequence: Synthetic
      DNA sequence

<400> SEQUENCE: 12
ggcaagcttg ggcctcatgt cgaagcggaa ggtacagtca gaagtagttg cgggggaggc    60 acggggagg tacggaggag tgcacggagg agcaatggcg atgacggatc ctca          114

<210> SEQ ID NO 13
<211> LENGTH: 114
<212> TYPE: DNA
<213> ORGANISM: Artificial Sequence
<220> FEATURE:
<221> NAME/KEY: misc_feature
<222> LOCATION: 1...114
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 13
ggcaagcttg ggcctcatgt cgaagcggaa ggtacagtca gaagtngttg cgggggagat    60 gcggggagg tacggaggag tgcacggagg agcaatggcg atgacggatc ctca           114

<210> SEQ ID NO 14
<211> LENGTH: 115
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 14
ggcaagcttg ggcctcatgt cgaagcggaa ggtacagtca gaagtagttg cgggggaggg    60 cacggggag gtacggagga gtgcacggag gagcaatggc gatgacggat cctca          115

<210> SEQ ID NO 15
<211> LENGTH: 115
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 15
ggcaagcttg ggcctcatgt cgaagcggaa ggtacagtca gaagtagttg cgggggaggg    60 tacggggag gtacggagga gtgcacggag gagcaatggc gatgacggat cctca          115

<210> SEQ ID NO 16
<211> LENGTH: 115
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 16
ggcaagcttg ggcctcatgt cgaagcggaa ggtacagtca gaagtagttg cgggggagag    60 cacggggag gtacggagga gtgcacggag gagcaatggc gatgacggat cctca          115

<210> SEQ ID NO 17
<211> LENGTH: 115
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 17
ggcaagcttg ggcctcatgt cgaagaagga gcacgaaatc ggcaatcagc gggggagagc    60
acggggggag gtacggagga gwgcacggag gagcaatggc gatgacggat cctca         115

<210> SEQ ID NO 18
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 18
ggcaagcttg ggcctcatgt cgaagcgcgg agtgaggtta acgccaggcg gaggagtggc    60 acggggagg tacggaggag tgcacggagg agcaatggcg atgacggatc ctca           114

<210> SEQ ID NO 19
<211> LENGTH: 115
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 19
ggcaagcttg ggcctcatgt cgaagctgga gcggagagta atcgctgtgc ggagggaggg    60 cacggggag gtacggagga gtgcacggag gagcaatggc gatgacggat cctca          115

<210> SEQ ID NO 20
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 20
ggcaagcttg ggcctcatgt cgaaggtgga gcggagagta atcgctgtgc gggggagggc    60 acggggagg tacggaggag tgcacggagg agcaatggcg atgacggatc ctca           114

<210> SEQ ID NO 21
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 21
ggcaagcttg ggcctcatgt cgaaggtggc gggtcagagt ggagccgtgc gggggagggc    60 acggggagg tacggaggag tgcacggagg agcaatggcg atgacggatc ctca           114

<210> SEQ ID NO 22
<211> LENGTH: 113
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 22
ggcaagcttg ggcctcatgt cgaaggaagc cgagaggatt ggcatcgtgc gggggaggca      60
cgggggaggt acggaggagt gcacggagga gcaatggcga tgacggatcc tca            113

<210> SEQ ID NO 23
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 23
ggcaagcttg ggcctcatgt cgaagcaagt atgggaacgg cgagcgttgt gggggagggc      60 acggggagg tacggaggag tgcacggagg agcaatggcg atgacggatc ctca             114

<210> SEQ ID NO 24
<211> LENGTH: 114
<212> TYPE: DNA
<213> ORGANISM: Artificial Sequence
<220> FEATURE:
<221> NAME/KEY: misc_feature
<222> LOCATION: 1...114
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE:    24 ggcaagcttg ggcctcatgt cgaaggtggc gggtcagagt ggagcbgtgc gngnsagggc      60 acggggagg tacggaggag tgcacggagg agcaatggcg atgacggatc ctca             114

<210> SEQ ID NO 25
<211> LENGTH: 115
<212> TYPE: DNA
<213> ORGANISM: Artificial Sequence
<220> FEATURE:
<221> NAME/KEY: misc_feature
<222> LOCATION: 1...115
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 25
ggcaagcttg ggcctcatgt cgaaggaagt gtggagtcaa atgtawcggg ggagngccgc      60 ggggaggaa cggaggagcg gcgtggggga gagcaatggc gatgacggat cctca            115

<210> SEQ ID NO 26
<211> LENGTH: 110
<212> TYPE: DNA
<213> ORGANISM: Artificial Sequence
<220> FEATURE:
<221> NAME/KEY: misc_feature
<222> LOCATION: 1...110
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 26
ggcaagcttg ggcctcatgt cgaagttggc accgtagccc atgggtcgga ggagcggcgc      60
gngggaggga cggaggcgcc gcggggagca atggcgatga cggatcctca                 110

<210> SEQ ID NO 27
<211> LENGTH: 116
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 27
ggcaagcttg ggcctcatgt cgaatgagac ggttgggaga cggcatcgcg cggggggaagg      60 atggaggagc aattgcgggg aaagtatgga ggagcaatgg cgatgacgga tcctca          116

<210> SEQ ID NO 28
<211> LENGTH: 100
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 28
tcatgtcgaa gcggaaggta tagtcagaag tagttgcggg ggaggcacgg gggaggtacg      60
gaggagtgta cggaggagca atggcgatga cggatcctca                            100

<210> SEQ ID NO 29
<211> LENGTH: 77
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 29
tcatgtcgaa ggcggtcagt cgccgctgcg gacggaggag gtacggggga gagagcaatg      60
gcgatgacgg atcctca                                                     77

<210> SEQ ID NO 30
<211> LENGTH: 79
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 30
tcatgtcgaa agccatggcg ggggatgcgg gggaggcacg gaggagcatc ggtggagcaa      60
tggcgatgac ggatcctca                                                   79

<210> SEQ ID NO 31
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 31
ggcaagcttg ggcctcatgt cgaacctact ggacggagga ggaacggggg agggaagtag      60
gtgagggagc aatggcgatg acggatcctc a                                     91

<210> SEQ ID NO 32
<211> LENGTH: 30
<212> TYPE: DNA
<213> ORGANISM: Artificial Sequence

```
<220> FEATURE:
<223> OTHER INFORMATION: Description of Artificial Sequence: Synthetic
      DNA sequence

<400> SEQUENCE: 32
gagatgcggg ggaggcacgg aggagcatcg                                        30

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 33
agccatggcg ggggagatgc gtagcatcgg tggagcaatg gcg                         43

<210> SEQ ID NO 34
<211> LENGTH: 58
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 34
gcctcatgtc gaacctactg gacggaggag gaacggggga gggaagtagg tgagggag         58

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 35
gcctcaccta ctggacggag gaggaacggg ggagggaagt aggtgaggga g                51

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 36
cctactggac ggaggaggaa cggggagggg aagtagg                                37

<210> SEQ ID NO 37
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 37
ggcaagcttg ggcctcatgt cgaagtgaca ccactgggtt gggtatgggt agggttgtgg       60
aatcacgagc aatggcgatg acggatcctc a                                      91

<210> SEQ ID NO 38
<211> LENGTH: 90
<212> TYPE: DNA
```

<213> ORGANISM: Artificial Sequence
<220> FEATURE:
<223> OTHER INFORMATION: Description of Artificial Sequence: Synthetic
      DNA sequence

<400> SEQUENCE: 38
ggcaagcttg ggcctcatgt cgaagtgaca ccactgggtt gggtadggt aggktgtgga      60 atcacgagca atggcgatga cggatcctca                                      90

<210> SEQ ID NO 39
<211> LENGTH: 91
<212> TYPE: DNA
<213> ORGANISM: Artificial Sequence
<220> FEATURE:
<221> NAME/KEY: misc_feature
<222> LOCATION: 1...91
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 39
ggcaagcttg ggcctcatgt cgaagtgaca ccactgggtt gggtanggt agggttgtgg      60 aatcacgagc aatggcgatg acggatcctc a                                    91

<210> SEQ ID NO 40
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 40
ggcaagcttg ggcctcatgt cgaagtgaca ccactgggtt gggtyggta gggttgtgga      60 atcacgagca atggcgatga cggatcctca                                      90

<210> SEQ ID NO 41
<211> LENGTH: 90
<212> TYPE: DNA
<213> ORGANISM: Artificial Sequence
<220> FEATURE:
<221> NAME/KEY: misc_feature
<222> LOCATION: 1...90
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 41
ggcaagcttg ggcctcatgt cgaagtgaca ccactgggtt gggtnggta gggttgtgga      60 atcacgagca atggcgatga cggatcctca                                      90

<210> SEQ ID NO 42
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 42
ggcaagcttg ggcctcatgt cgaagctatg cagatcgcca taagtgggtt ggcatggga     60 agggtggagc aatggcgatg acggatcctc a                                    91

<210> SEQ ID NO 43
<211> LENGTH: 94
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 43
ggcaagcttg ggcctcatgt cgaagctacg caaatcgcca caagtggagt tgggactggg    60
agmaaggtgg agcaatggcg atgacggatc ctca                                94

<210> SEQ ID NO 44
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 44
ggcaagcttg ggcctcatgt cgaatcaggc agcgctgcga tttgggctgg gaatgggaag    60
ggttagagca atggcgatga cggatcctca                                     90

<210> SEQ ID NO 45
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 45
ggcaagcttg ggcctcatgt cgaaccggca tcgttagtgt aatgggctgg gcatgggtta    60
gggtgagagc aatggcgatg acggatcctc a                                   91

<210> SEQ ID NO 46
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 46
ggcaagcttg ggcctcatgt cgaagcatgg ccacattggg aatgggctgg gaatgggtag    60
ggttcgagca atggcgatga cggatcctca                                     90

<210> SEQ ID NO 47
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 47
ggcaagcttg ggcctcatgt cgaagtcgtg ccgatgtctc ggtggggtgg gtatgggtag    60
ggtaacgagc aatggcgatg acggatcctc a                                   91

<210> SEQ ID NO 48
<211> LENGTH: 91
<212> TYPE: DNA
<213> ORGANISM: Artificial Sequence

```
<220> FEATURE:
<223> OTHER INFORMATION: Description of Artificial Sequence: Synthetic
      DNA sequence

<400> SEQUENCE: 48
ggcaagcttg ggcctcatgt cgaagccgaa tgggctggga atggtgtagg gttttcggct     60
atgtccgagc aatggcgatg acggatcctc a                                   91

<210> SEQ ID NO 49
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 49
ggcaagcttg ggcctcatgt cgaagtaggt gggatgggca tggggagggt ggctactgga     60
acgtgagagc aatggcgatg acggatcctc a                                   91

<210> SEQ ID NO 50
<211> LENGTH: 91
<212> TYPE: DNA
<213> ORGANISM: Artificial Sequence
<220> FEATURE:
<221> NAME/KEY: misc_feature
<222> LOCATION: 1...91
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 50
ggcaagcttg ggcctcatgt cgaatacagt gggtgtaggg aatgnntggg ttawgtattt     60
gtgtttgagc aatggcgatg acggatcctc a                                   91

<210> SEQ ID NO 51
<211> LENGTH: 89
<212> TYPE: DNA
<213> ORGANISM: Artificial Sequence
<220> FEATURE:
<221> NAME/KEY: misc_feature
<222> LOCATION: 1...89
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 51
ggcaagcttg ggcctcatgt cgaacggcag tgtccgggtt gggcbgggaa ggbanggtcg     60
cctggagcaa tggcgatgac ggatcctca                                      89

<210> SEQ ID NO 52
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 52
ggcaagcttg ggcctcatgt cgaaggggtt atgcatgggc gtgggaatgg ccgacaagga     60
gccccgagca atggcgatga cggatcctca                                     90
```

```
<210> SEQ ID NO 53
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 53
ggcaagcttg ggcctcatgt cgaaggggg cgtatgaaat ctgggtgcgg ggggatgagc      60
cgatacgagc aatggcgatg acggatcctc a                                    91

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 54
aggtgacacc actgggttgg gtatgggtag ggttgtggaa tcac                      44

<210> SEQ ID NO 55
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 55
aggtgacacc actggggtgg gtatgggtag ggttgtggaa tcac                      44

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 56
agatcgccat aagtgggttg ggcatgggaa gggtggagca atggcgat                  48

<210> SEQ ID NO 57
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 57
gtcgtgccga tgtctcggtg gggtgggtat gggtaggta acgagcaatg gc              52

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 58
aggggttatg catgggcgtg ggaatggccg acaaggagcc cc                        42
```

<210> SEQ ID NO 59
<211> LENGTH: 92
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 59
ggcaagcttg ggcctcatgt cgaaggggcg tatgggcttt ggggagggtt tcggcgacat    60
gtcctcagag caatggcgat gacggatcct ca                                  92

<210> SEQ ID NO 60
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 60
ggcaagcttg ggcctcatgt cgaaggggcg tatgggcttt ggggagggtt cggcgacatg    60
atgtcgagca atggcgatga cggatcctca                                     90

<210> SEQ ID NO 61
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 61
ggcaagcttg ggcctcatgt cgaaggggcg tatgggcttt ggggagggtt tcggcgacat    60
ggtgccgagc aatggcgatg acggatcctc a                                   91

<210> SEQ ID NO 62
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 62
ggcaagcttg ggcctcatgt cgaatccatt gatccgcggc agtgcgggag ggtggaggtg    60
tgcttggagc aatggcgatg acggatcctc a                                   91

<210> SEQ ID NO 63
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 63
ggcaagcttg ggcctcatgt cgaatccatt gatccgcggc agtgcgggag ggtagaggtg    60
tgcttggagc aatggcgatg acggatcctc a                                   91

<210> SEQ ID NO 64
<211> LENGTH: 90
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 64
ggcaagcttg ggcccatgtc gaagcttaac tagggtcgcc atgcgggagg gtagaggtgt      60
gcttggagca atggcgatga cggatcctca                                       90

<210> SEQ ID NO 65
<211> LENGTH: 92
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 65
ggcaagcttg ggcctcatgt cgaaggtgac gtgtattggc agtgcgggag tggtagaggt      60
gtgcttggag caatggcgat gacggatcct ca                                    92

<210> SEQ ID NO 66
<211> LENGTH: 92
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 66
ggcaagcttg ggcctcatgt cgaatccatt gatccgcgcg cagtgcsgga gggtaraggt      60
gtgcttggag caatggcgat gacggatcct ca                                    92

<210> SEQ ID NO 67
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 67
ggcaagcttg ggcctcatgt cgaagggagt gggaggggttg agggtgctt ggaacggctg      60 cgacaggagc aatggcgatg acggatcctc a                                     91

<210> SEQ ID NO 68
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 68
ggcaagcttg ggcctcatgt cgaagggagt gggaggggttg agggtgctt ggaacgactg      60 cgacaggagc aatggcgatg acggatcctc a                                     91

<210> SEQ ID NO 69
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 69
ggcaagcttg ggcctcatgt cgaaggcgta tagggagcgg gtacggtgga aggggttagc    60
ctacatgagc aatggcgatg acggatcctc a    91

<210> SEQ ID NO 70
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 70
ggcaagcttg ggcctcatgt cgaaggtggg cgtatgaaat ctgggtgcgg ggtatgacc    60 ttatacgagc aatggcgatg acggatcctc a    91

<210> SEQ ID NO 71
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 71
ggcaagcttg ggcctcatgt cgaaggggggg ggtatgaaat ctgggtgcgg ggggatgagc    60
cgatacgagc aatggcgatg acggatcctc a    91

<210> SEQ ID NO 72
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 72
ggcaagcttg ggcctcatgt cgaaggaagg cgtatgaaat ctgggtgcgg gggtatgagc    60
cgatacgagc aatggcgatg acggatcctc a    91

<210> SEQ ID NO 73
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 73
ggcaagcttg ggcctcatgt cgaaggtggg cgtatgaaat ctgggtgcgg gggtrkcccc    60
ttgkrggagc aatggcgatg acggatcctc a    91

<210> SEQ ID NO 74
<211> LENGTH: 91
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 74
ggcaagcttg ggcctcatgt cgaagggtgg gctaggcata gtgaacaggt aggggcgact    60
agggacgagc aatggcgatg acggatcctc a                              91

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 75
tcatgtcgaa ggggcgtatg ggctttgggg agggtttcgg cgacatgt            48

<210> SEQ ID NO 76
<211> LENGTH: 58
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 76
tgatccgcgg cagtgcggga gggtggaggt gtgcttggag caatggcgat gacggatc   58

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 77
gcctcatgtc gaacctactg ga                                        22

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 78
ggaagtaggt gagggag                                              17

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 79
tcatgtcgaa ggggcgtatg ggctttg                                   27

<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 80
tgatccgcgg cagtgc                                               16

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 81
tgcttggagc aatggcgatg acggatc                                         27

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 82
agtgacacca c                                                          11

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 83
tgtggaatca c                                                          11

<210> SEQ ID NO 84
<211> LENGTH: 13
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 84
agatcgccat aag                                                        13

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 85
ggagcaatgg cgat                                                       14

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 86
ggcaagcttg ggcctcatgt cgaa                                            24

```
<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 87
tgaggatccg tcatcgccat tgctc                                         25

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 88
ggcaagcttg ggcctcatgt cgaa                                          24

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 89
tgaggatccg tcatcgccat tgctc                                         25

<210> SEQ ID NO 90
<211> LENGTH: 20
<212> TYPE: DNA
<213> ORGANISM: Artificial Sequence
<220> FEATURE:
<221> NAME/KEY: misc_feature
<222> LOCATION: 1...20
<223> OTHER INFORMATION: Description of Artificial Sequence: Synthetic
      DNA sequence
<223> OTHER INFORMATION: Description of Artificial Sequence: n is any
      one of g, a, t or c

<400> SEQUENCE: 90
tgggntgggn tgggnagggt                                               20
```

METHOD FOR SEQUENCING AND CHARACTERIZING POLYMERIC BIOMOLECULES USING APTAMERS AND A METHOD FOR PRODUCING APTAMERS

This application claims benefit from U.S. Provisional Application No. 60/135,863 filed May 25, 1999.

The invention herein was made in part with Government support from the Department of Health and Human Services. Accordingly, the U.S. Government may have certain rights in this invention.

TECHNICAL FIELD OF THE INVENTION

The present invention provides aptamers that recognize and bind to guanosine (GMP), deoxyguanosine (dGMP), adenosine (AMP), deoxyadenosine (dAMP), cytosine (CMP) and deoxycytosine (dCMP). The present invention also relates to a method for sequencing a polymeric biomolecule and a method for structurally characterizing the same comprising the use of aptamers. In a preferred embodiment of this invention, these methods relate to the sequencing or characterization of a single polymeric biomolecule. The invention also relates to a method for selecting aptamers useful for sequencing nucleic acids.

BACKGROUND OF THE INVENTION

Knowing the primary structure and composition of polymeric biomolecules, such as DNA, RNA, polysaccharides, lipids and polypeptides, is important for scientific and medical research and the development of medical treatments. For example, information regarding the primary structure of certain polymeric biomolecules is important for studying the genetic basis of certain diseases, understanding role that polysaccharides play in cellular recognition processes, determining the DNA sequence of a purified protein and producing recombinant proteins for assays for screening drugs. Thus, fast, accurate and efficient methods for determinating the primary structure and composition of a polymeric biomolecule, especially a biomolecule that is long and/or is in short supply, are important for progress in research.

1.1 DNA Sequencing

Approaches to sequencing DNA have varied widely. The Maxam-Gilbert technique for sequencing (Maxam and Gilbert, 1977, PNAS USA 74:560) involves four separate chemical cleavage reactions using the same DNA molecules. The partial or total cleavage of the DNAs, which are end-labeled, produce varying sized DNAs which are run on a gel electrophoresis apparatus. The sequence of the DNA molecule is determined from the migratory position of the bands in the gel. The dideoxy method of sequencing (Sanger et al., 1977, PNAS USA 74:5463) involves four enzymatic reactions using DNA polymerase to synthesize fragments of varying lengths due to the incorporation of a chain terminating dideoxy nucleotide into each fragment. Typically, radioactively-labeled nucleotide(s) are incorporated into the growing chains. Variations on the Sanger method comprise the use of fluorescent dye-labeled primers or nucleotide chain terminators. The reactions are then run on a gel electrophoresis apparatus. The sequence of the DNA molecule is determined from the migratory position of the cleaved bands in the gel. Fluorescence emissions from the dyes are monitored. These gel-based, ladder-like output methods are disadvantageous, in part, because they (1) require substantial amounts of template DNA for the reactions to occur, (2) produce a relatively small number of resolvable, visual fragments per reaction, (3) require time for the separation of the fragments and generation of the ladder, (4) require resequencing and overlapping sequencing reactions to determine the primary sequence of a long piece of DNA. A typical DNA sequencing as described above may yield the sequence of 300–500 nucleotides of a desired nucleic acid.

Alternatively, sequencing methods involving the use of an exonuclease to cleave off a terminal nucleotide of a single DNA molecule have been described. Jett et al. (U.S. Pat. No. 4,962,037) describes a method wherein a complementary strand of the DNA to be sequenced is synthesized with nucleotides covalently bonded to a fluorescent dye. Then, the labeled complementary strand of the desired DNA is sequenced using exonuclease cleavage. In practice, the exonuclease cleavage is hindered by the presence of dye on each nucleotide. Ishikawa (U.S. Pat. No. 5,528,046) describes the use of monoclonal antibodies against nucleotides A, G, T or C for detecting nucleotides freed from the DNA being sequenced. The monoclonal antibody in Ishikawa may be conjugated to a light emitting reagent, particularly a luminescent enzyme, to facilitate detection of the freed nucleotide. However, the use of monoclonal antibodies is disadvantageous, inter alia, because the production of monoclonal antibodies is labor intensive and requires considerable animal and cell culture resources for production and screening.

Thus, there is a need for alternative, sensitive methods for rapidly and accurately obtaining the nucleic acid sequence information. This is especially true for nucleic acid sequences that are long (greater than 1000 bp) and/or in short supply (less than nanomolar range).

1.2 Protein Sequencing

Chemical protein sequencing has been and continues to be one of the most popular methods for determining the primary structure of proteins. See Stolowitz, "Chemical Protein Sequencing and Amino Acid Analysis," *Curr. Opin. Biotech.* 4:9–13 (1993) and Hunkapiller, M. W., "Contemporary Methodology for the Determination of the Primary Structure of Proteins," *Macromol. Seq. and Synthesis,* Ed. D. H. Schlesinger, pp.45–58, Alan R. Liss: New York, N.Y. (1988).

Traditional chemical amino-terminal sequencing includes a degradation step such as Edman degradation and a detection step. Edman degradation typically includes a coupling step, a cleavage step, and a conversion step. For example, in an Edman degradation, the amino terminus of a target polypeptide is coupled to an isothiocyanate reagent and then the derivatized N-terminal amino acid is cleaved from the polypeptide with a strong organic acid. The reagents of the Edman process may be delivered to the target polypeptide in a vapor (gas-phase method) or in a liquid pulse (pulsed-liquid method). The target polypeptide may be covalently (e.g., with carbonyldiimidazole) or non-covalently (e.g., with polybrene) attached to a solid support. Solid supports used in protein sequencing include polyvinylidene difluoride (PVDF), glass beads or polystyrene beads. The cleaved amino acid is typically converted to a more stable phenylthiohydantoin (PTH) form by treatment with an aqueous solution of strong organic acid. The PTH amino acid may be detected, for example, by high pressure liquid chromatography (HPLC) with UV absorbance detectors or by mass spectrometry (Aebersold, R., et al., "Design, Synthesis, and Characterization of a Protein Sequencing Reagent Yielding Amino Acid Derivatives with Enhanced Detectability by Mass Spectrometry," *Protein Science* 1:494–503 (1992)).

In an alternative chemical sequencing method, the degradation step involves the thioacetylation of the amino-terminal amino acid, which is detected by gas chromatography/mass spectrometry (Stolowitz, M L et al., "Thioacetylation Method of Protein Sequencing: Gas Chromatography/Ion Trap Mass Spectrometric Detection of 5-acetoxy-2-Methylthiazoles," *J. Protein Chem.* 11:360–361 (1992)). In another chemical sequencing process, a peptide ladder generated by Edman degradation is analyzed using matrix-assisted, laser desorption, time-of-flight mass spectrometry (Chait, et al., "Protein Ladder Sequencing," *Science* 262:89–92 (1993)).

Chemical cleavage of carboxy-terminal amino acids has been achieved through a variety of methods (Inglis, A. S., "Chemical Procedures for C-Terminal Sequencing of Peptides and Proteins," *Analytical Biochemistry* 195:183–196 (1991)). For example, the carboxy-terminus of a polypeptide has been coupled to a thiocyanate salt or thiocyanic acid (HSCN) to form a thiohydantoin or a peptidyl isothiocyanate which may be cleaved to form a thiohydantoin. The thiohydantoin-carboxy terminal amino acid can be detected by its UV absorption. Other carboxy-terminal cleavage reactions which do not involve the formation of a thiohydantoin can be characterized by the formation of (1) an acyl urea; (2) an O-peptidyl amino alcohol; (3) an N-peptidyl-2-oxazolidone; (4) an oxazole; and (5) an azide which is converted into an isocyanate. See, supra, Table 1 in Inglis.

Enzymatic digestion of terminal amino acids have been used to sequence polypeptides. Some amino-terminal and carboxy-terminal specific exopeptidases known in the art are carboxypeptidases (i.e. Y, A, B, and P), aminopeptidase 1, LAP, proline aminodipeptidase, leucine aminopeptidase, microsomal peptidase and cathepsin C. Serine carboxypeptidases have proven to be useful in sequentially cleaving residue by residue from the C-terminus of a protein or a peptide. Carboxypeptidase Y (CPY), in particular, is an attractive enzyme because it non-specifically cleaves all residues from the C-terminus, including proline. See, e.g., Breddam et al. (1987) *Carlsburg Res. Commun.* 52:55–63, U.S. Pat. No. 5,869,240 (Patterson); U.S. Pat. No. 5,792,664 (Chait et al.); and Tsugita et al. (1992) "C-terminal Sequencing of Protein: A Novel Partial Acid Hydrolysis and Analysis by Mass Spectrometry," *Eur. J. Biochem.* 206:691–696.

The methods described above require at a minimum subfemtomole concentrations of polypeptide. They are also sensitive to the purity of the polypeptide sample. For example, the presence of a co-purifying protein contaminant during the sequencing of a target polypeptide may give rise to sequencing errors. Further, carryover of incomplete amino-terminal cleavage into the next cycle results in a steadily increasing proportion of a population of molecules being out of phase with the expected order of release. Finally, recovery and detection of the cleaved amino acid can be difficult under current methods.

Thus, there is a need for alternative, sensitive methods for rapidly and accurately obtaining the primary amino acid sequence information of polypeptides, especially for longer chain polypeptides and/or for polypeptides that are in short supply.

1.3 Polysaccharide Sequencing

Polysaccharides play an important role in the regulation of biological processes in every life form from bacteria to plants to mammals. For example, carbohydrate moieties in glycoproteins are have been shown to be involved in protein targeting, cell-cell recognition, and antigen-antibody reaction (J. C. Paulson, *Trends Biochem. Sci.,* 14:272 (1989)).

Technologies for structurally characterizing target polysaccharides include the use of enzymes, gel permeation chromatography, high-performance anion exchange pulsed amperometric detection, electrospray or laser desorption mass spectrometry, capillary electrophoresis, hydrazinolysis, gas chromatography-mass spectrometry (GCMS), fast-atom bombardment and liquid secondary ion mass spectrometry and nuclear magnetic resonance (e.g., Geisow, M., "Shifting Gear in Carbohydrate Analysis," *Bio/Technology* 10:277–280). Methods for isolating and purifying polysaccharides from proteins or lipids are known (e.g., Welply, J., (1989) "Sequencing Methods for Carbohydrates and Their Biological Applications," *TIBTECH* 7:5–10; Pazur, J., "Neutral Polysaccharides," *Carbohydrate Analysis: A Practical Approach,* 2nd Ed., Eds. M. F. Chaplain and J. F. Kennedy, Oxford University Press, Inc.: New York, 1994).

Techniques for determining the sequence of target polysaccharides include proton NMR, fast atom bombardment mass spectroscopy, antibody or lectin-binding to the polypeptide to confirm the presence of a particular oligonucleotide sequence, and enzymatic digestion. Exoglycosidases commonly used for oligosaccharide sequencing include mannosidases, hexosaminidases, galactosidases, fucosidase, neuraminidases, and glucosidases (e.g., A. Kobata, *Anal. Biochem.,* 100:1–14 (1979)).

One approach to carbohydrate sequencing is sequential digestion of an oligosaccharide with an exoglycosidase of known specificity (e.g., A. Kobata, in *Biology of Carbohydrates,* vol. 2., Eds. V. Ginsburg et al., John Wiley & Sons: New York (1984); supra, A. Kobata, *Anal. Biochem.,* 100:1–14 (1979)). For example, a tritiated polysaccharide would be digested with an exoglycosidase. The cleavage reaction would be monitored by comparing the uncleaved portion of the polysaccharide before and after exposure to the enzyme using paper chromatography, gel electrophoresis, and gel permeation chromatography. This technique is disadvantageous in that it requires the repeated isolation and determination of the oligosaccharide size before and after enzyme incubation. Consequently, this method requires much starting material and time and effort to isolate the uncleaved portion of oligossacharide.

Another method, the reagent array analysis method (RAAM), has been used to sequence polysaccharides (e.g., Prime, S and T. Merry, "Exoglysidase Sequencing of N-linked Glycans by the Reagent Array Analysis Method (RAAM)," in *Methods in Molecular Biology, vol. 76: Glycoanalysis Protocols,* Ed., E. F. Hounsell, Humana Press Inc.: New Jersey (1998); C. T. Edge et al., *PNAS USA* 89:6338 (1992); U.S. Pat. No. 5,100,778 (Dwek et al.)). This method involves the digestion of an aliquot of target polypeptide with a defined mixture of exoglycosidases such that the polypeptide in each aliquot is digested up to a certain point. This is repeated with other aliquots of the polypeptide and different, defined mixtures of exoglycosidases. The uncleaved portion of the polypeptide in each aliquot is analyzed to identify the sequence of the original polysaccharide. Consequently, this method also requires much starting material and time and effort to isolate the uncleaved portion of the polysaccharide.

Thus, there is a need for alternative, sensitive methods for rapidly and accurately obtaining the primary monosaccharide sequence of polysaccharides, especially for longer chain polysaccharides and/or for polysaccharides samples which are limited in supply.

1.4 Aptamers

Aptamers are small single stranded RNAs or DNAs approximately 40–100 base pairs in length that form secondary and tertiary structures which bind to other biological molecules. Some aptamers having affinity to a specific protein, DNA, amino acid and nucleotides have been described (e.g., K. Y. Wang, et al., "A DNA Aptamer Which Binds to and Inhibits Thrombin Exhibits a New Structural Motif for DNA," *Biochemistry* 32:1899–1904 (1993); Pitner et al., U.S. Pat. No. 5,691,145; Gold, et al., "Diversity of Oligonucleotide Function," *Ann. Rev. Biochem.* 64: 763–97 (1995); Szostak et al., U.S. Pat. No. 5,631,146). High affinity and high specificity binding aptamers have been derived from combinatorial libraries (supra, Gold, et al.). Aptamers may have high affinities, with equilibrium dissociation constants ranging from micromolar to sub-nanomolar depending on the selection used. Aptamers may also exhibit high selectivity, for example, showing a thousand fold discrimination between 7-methylG and G (Haller, A. A., and Sarnow, P., "In Vitro Selection of a 7-Methyl-Guanosine Binding RNA That Inhibits Translation of Capped mRNA molecules, *PNAS USA* 94:8521–8526 (1997)) or between D and L-tryptophan (supra, Gold et al.).

General methods for screening randomized oligonucleotides for aptamer activity have been described. For example, Gold, et al. (U.S. Pat. No. 5,270,163) describes the "SELEX" (Systematic Evolution of Ligands by Exponential Enrichment) method. In Gold et al., a candidate mixture of single stranded nucleic acid having regions of randomized sequence is contacted with a target molecule. Those nucleic acids having an increased affinity to the target are partitioned from the remainder of the candidate mixture. The partitioned nucleic acids are amplified to yield a ligand enriched mixture. Szostak et al. (U.S. Pat. No. 5,631,146) describes a method for producing a single stranded DNA molecule which binds adenosine or an adenosine-5'-phosphate. In Szostak, aptamers with affinity for adenosine or adenosine-5'-phosphate are partitioned away from aptamers with less affinity using affinity column chromatography. The ATP column of Szostak has ATP linked to the agarose through the C8 carbon of the adenine base. The resulting selected aptamers are unable to recognize portions of the adenine base especially around the C8 region of the adenine base.

Aptamers with good specificity and affinity for adenosine and the bases of other nucleotides are useful, inter alia, for DNA and RNA sequencing according to the methods of this invention. Thus, there exists a need for a method for obtaining an improved selection of aptamers for sequencing and characterizing nucleic acid molecules.

The methods of this invention satisfy several objectives. They provide an alternative, highly sensitive and rapid method for sequencing a polymeric biomolecule of extended length that does not require labeling of the target polymeric biomolecule before sequencing and avoids the repeated isolation and analysis of uncleaved portions of a polymeric biomolecule of past sequencing methods. They provide a method for sequencing or characterizing a single polymeric biomolecule or an amount of polymeric biomolecule below subfemtomolar range.

SUMMARY OF THE INVENTION

The invention provides methods for sequencing a polymeric biomolecule comprising the steps of separating a terminal monomer from the polymeric biomolecule and identifying the separated terminal monomer using an aptamer. The separation step comprises using a cleaving reagent to catalyze the hydrolysis of the terminal monomer from the polymeric biomolecule. The polymeric biomolecule may be attached to a solid support. In a preferred embodiment of this invention, the cleaving agent is an enzyme such as an exonuclease, an exogylcosidase or an exopeptidase. In a preferred embodiment of this invention, the cleaved monomer is deposited onto a surface in a orderly manner for detection by the aptamer. In a more preferred embodiment of this invention, the surface onto which the monomer is deposited is a patterned surface with regions of differing hydrophilicity and/or is passivated against non-specific adsorption of the recognition molecules. In a preferred embodiment of this invention, the aptamer is labeled with an optically detectable species. Preferred polymeric biomolecules for use with the methods of this invention are DNA, RNA, polypeptides or polysaccharides. Particularly preferred biomolecules of this invention are polynucleotides.

The present invention provides an improved method for producing aptamers with strong binding affinity and selectivity for their target monomer comprising the steps of separating the desired aptamer from a mixture of aptamers by exposing the mixture of aptamers to an affinity system comprising the target monomer at low temperature, amplifying the aptamer that bound to the affinity system, and repeating the separation and amplification steps until the aptamer(s) having the desired affinity and selectivity are obtained. The low temperature is approximately a temperature between less than 10° C. to above freezing point. In a preferred embodiment, the low temperature is closer to the freezing point. The method of selection of this invention is particularly useful for developing aptamers useful for sequencing and characterizing DNA according to the methods of this invention.

The present invention also provides a method for producing an aptamer for recognizing a target nucleotide or nucleoside comprising the step of separating the aptamer from a mixture of aptamers using an affinity system, wherein the affinity system comprises the target nucleotide or nucleoside attached to a solid support through the 5' carbon of the sugar ring. According to a preferred embodiment of the invention the target nucleotide is attached to the solid support through the phosphate on the 5' carbon of the sugar ring. In a further embodiment of this method, the separation step is carried out at low temperature, i.e., approximately a temperature between less than 10° C. to above freezing point. In a preferred embodiment, the temperature is closer to the freezing point.

The invention provides a single-stranded nucleic acid molecule that recognizes and binds to AMP and dAMP. The invention also provides a single-stranded nucleic acid molecule that recognizes and binds to CMP and dCMP. This invention further provides a single-stranded nucleic acid molecule that recognizes and binds to GMP and dGMP. The invention also provides several specific nucleic molecules that recognize AMP, dAMP, CMP, dCMP, GMP or dGMP. In one preferred embodiment of the invention, the binding of the nucleic acid molecule to the nucleotide has a dissociation constant that is less than 3 $\mu$M.

BRIEF DESCRIPTION OF THE DRAWINGS

FIGS. 4a–4b discloses (4a) the sequence of clones obtained from Round 14 dAMP selection, and (4b) the sequence of abridged clones. DNA amplified from round 14 was either cloned without separating the DNA based on oligomer length (unprimed clone numbers), or first gel purified to isolate the band corresponding to 91-mers, (primed clone numbers). Clone sequence is composed of fixed sequence (lower case), variable sequence (uppercase), highly conserved or consensus sequence (boldtype), and complimentary regions (underlined) flanking the consensus. The sequences have been assigned the following sequence identifier numbers:

| Sequence | Sequence Identifier |
| --- | --- |
| dA20 | SEQ ID NO:6 |
| dA7' | SEQ ID NO:7 |
| dA3' | SEQ ID NO:8 |
| dA13' | SEQ ID NO:9 |
| dA19 | SEQ ID NO:10 |
| dA12' | SEQ ID NO:11 |
| dA21 | SEQ ID NO:12 |
| dA18 | SEQ ID NO:13 |
| dA4 | SEQ ID NO:14 |
| dA6 | SEQ ID NO:15 |
| dA12 | SEQ ID NO:16 |
| dA9' | SEQ ID NO:17 |
| dA9 | SEQ ID NO:18 |
| dA13 | SEQ ID NO:19 |
| dA33 | SEQ ID NO:20 |
| dA28 | SEQ ID NO:21 |
| dA17 | SEQ ID NO:22 |
| dA23 | SEQ ID NO:23 |
| dA22 | SEQ ID NO:24 |
| dA31 | SEQ ID NO:25 |
| dA1 | SEQ ID NO:26 |
| dA14' | SEQ ID NO:27 |
| dA34.100 | SEQ ID NO:28 |
| dA20.77 | SEQ ID NO:29 |
| dA19.81 | SEQ ID NO:30 |
| dA13'.91 | SEQ ID NO:31 |
| dA19.30 | SEQ ID NO:32 |
| dA19.43 | SEQ ID NO:33 |
| dA13'.58 | SEQ ID NO:34 |
| dA13'.51 | SEQ ID NO:35 |
| dA13'.37 | SEQ ID NO:36 |

FIGS. 5a–5D depicts the elution profiles for dAMP-aptamers tested for binding affinity on columns of dAMP-agarose. (5a) clone dA34.100, (5b) clone dA20.77, (5c) clone dA19.81, (5d) clone dA13'.91.

FIGS. 6a–6c depicts the calculated secondary structure for clones (6a) dA19.30, (6b) dA19.81, and (6c) dA19.43.

FIGS. 7a–7c depicts the elution profiles providing relative binding affinity for dAMP for clones (7a) dA19.81, (7b) dA19.30, and (7c) dA19.43.

FIGS. 8a–8b depicts the elution profile for Clone dA19.30 on dAMP-agarose with an (8a) ethylenediamine linker (8b) or triethyleneglycoldiamine (Jeffamine) linker.

FIGS. 9a–9d depicts the elution profile on affinity columns of dAMP-Jeffamine-agarose for clone dA13'.91 folded at (9a) 75° C., and (9b) 85° C., for clone dA13'.58 folded at (9c) 75° C., and (9d) 85° C.

Figure 10:
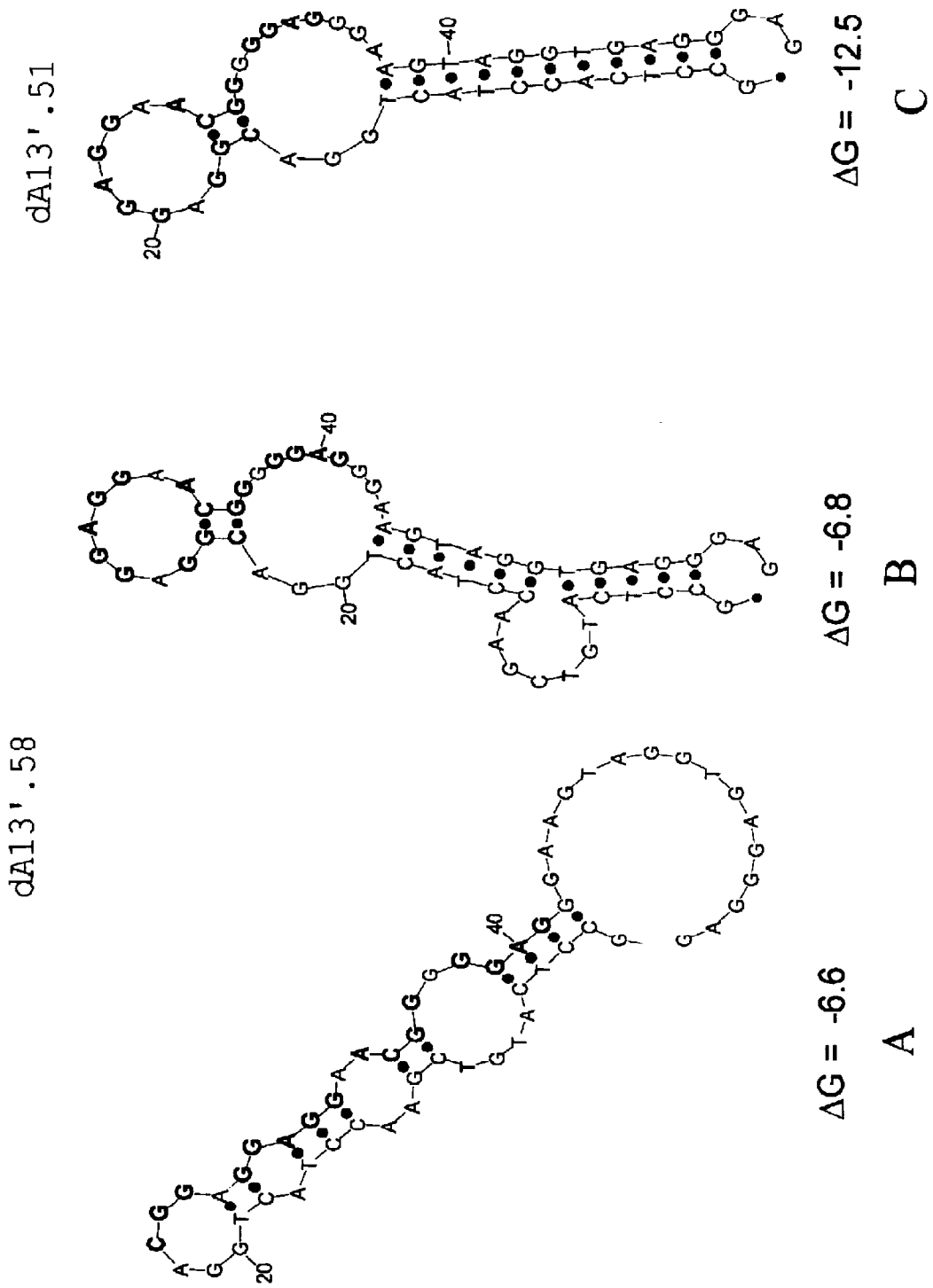

FIGS. 10a–10c depicts the calculated structure and free-energy for clone dA13'.58 with free energy of (10a) –6.6 kcal/mole, (10b) –6.8 kcal/mole, and for clone dA13'.51 with free energy of (10c) –12.5 kcal/mole.

FIGS. 11a–11b depicts the elution profile on affinity columns of dAMP-Jeffamine-agaro se for the dAMP-aptamers (11a) dA13'.51, and (11b) dA13'.58.

FIGS. 12a–12d depicts the elution profiles for the dAMP-aptamer dA13'.58 on affinity columns of dNMP-jeffamine-agarose, where the nucleotide N is (12a) dAMP, (12b) dGMP, (12c) TPM, and (12d) dCMP.

Figure 13:
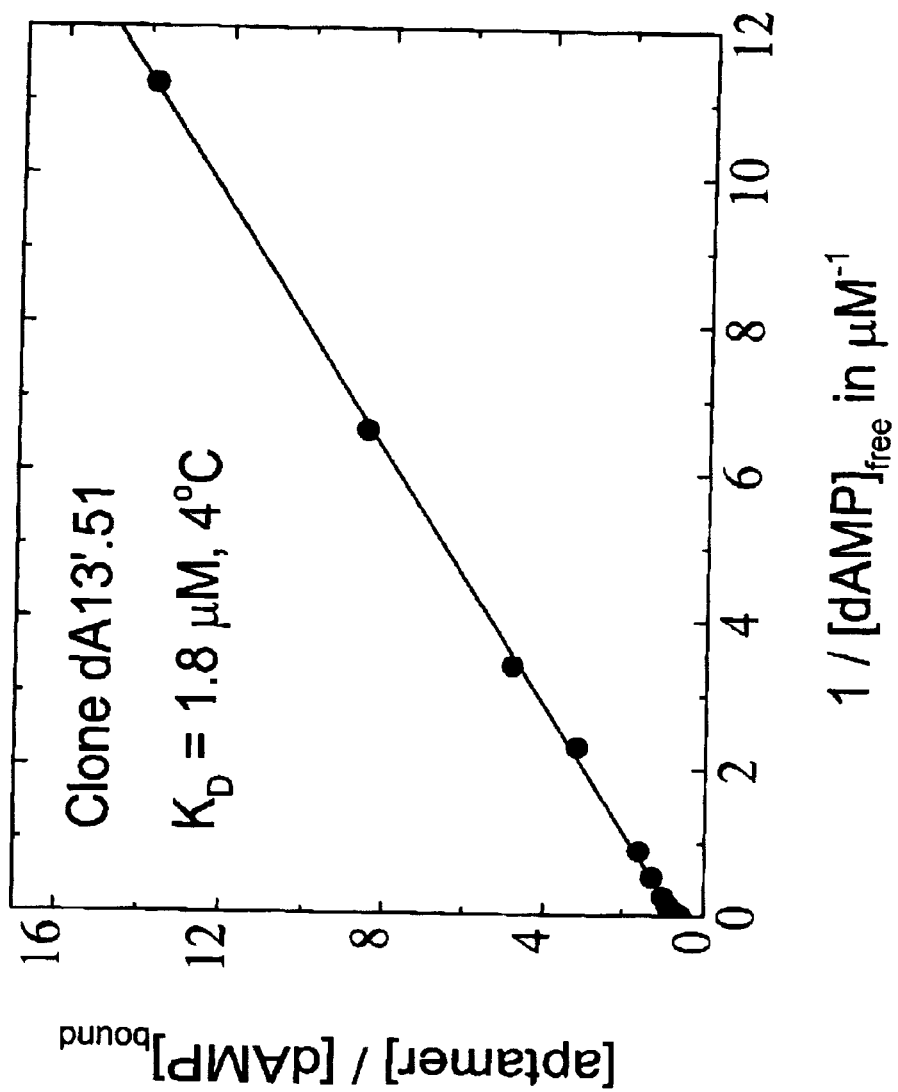

FIG. 13 depicts the solution binding titration based on analytical ultrafiltration for binding of dAMP and clone dA13'.58 at 4° C.

Figure 14:
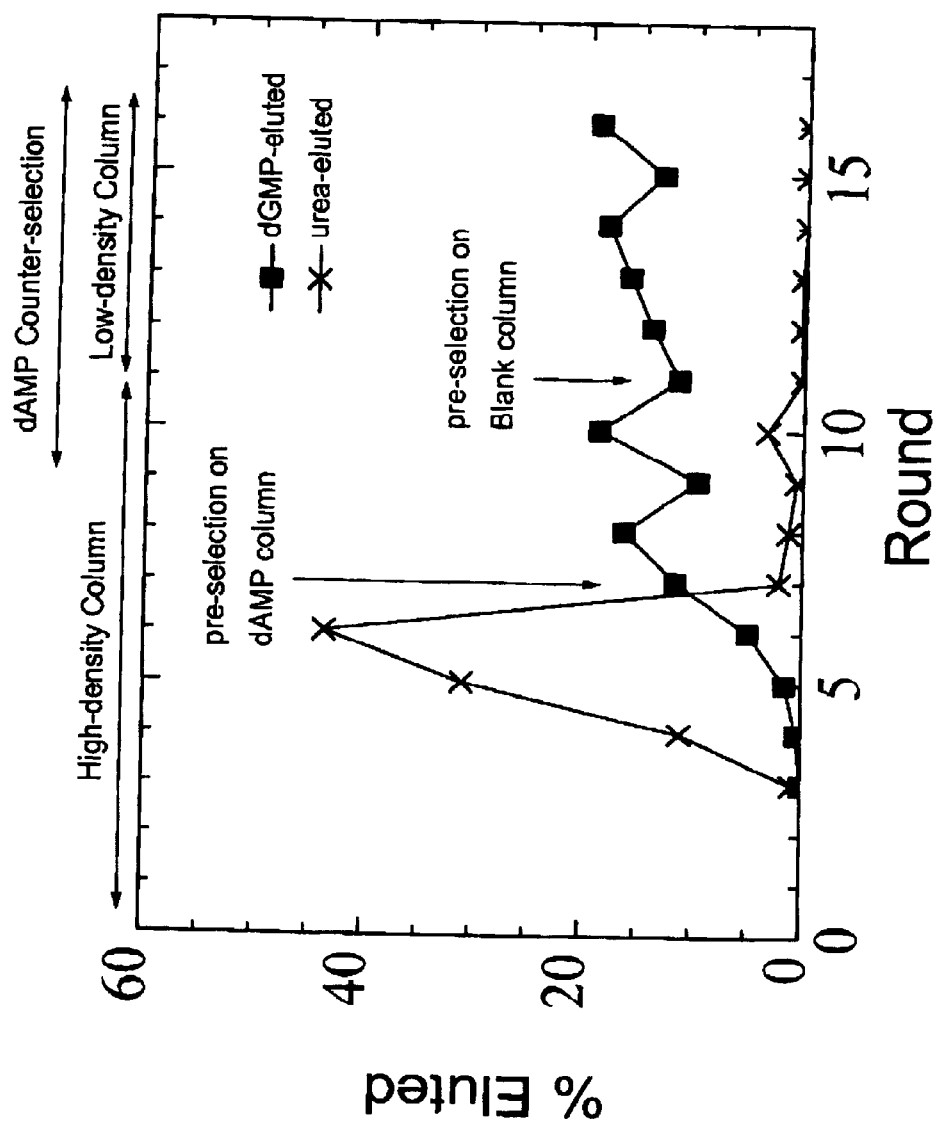

FIG. 14 depicts the percentage of DNA specifically eluted vs. round number for the dGMP selection.

FIGS. 15a–15b discloses the (15a) sequence of clones obtained from Round 16 dGMP selection, and (15b) sequence of abridged clones. Clone sequence is composed of fixed sequence (lower case), variable sequence (uppercase), highly conserverd or consensus sequence (boldtype), and complimentary regions (underlined) flanking the consensus. The sequences have been assigned the following sequence identifier number:

| Sequence | Sequence Identifier |
| --- | --- |
| dG17 | SEQ ID NO:37 |
| dG20 | SEQ ID NO:38 |
| dG26 | SEQ ID NO:39 |
| dG5 | SEQ ID NO:40 |
| dG7 | SEQ ID NO:41 |
| dG4 | SEQ ID NO:42 |
| dG32 | SEQ ID NO:43 |
| dG14 | SEQ ID NO:44 |
| dG29 | SEQ ID NO:45 |
| dG8 | SEQ ID NO:46 |
| dG21 | SEQ ID NO:47 |
| dG36 | SEQ ID NO:48 |
| dG3 | SEQ ID NO:49 |
| dG35 | SEQ ID NO:50 |
| dG37 | SEQ ID NO:51 |
| dG15 | SEQ ID NO:52 |
| dG19 | SEQ ID NO:53 |
| dG17.44 | SEQ ID NO:54 |
| dG17.44.g | SEQ ID NO:55 |
| dG4.48 | SEQ ID NO:56 |
| dG21.52 | SEQ ID NO:57 |
| dG15.42 | SEQ ID NO:58 |

FIGS. 16a–16d depicts the elution profiles on dGMP-Jeffamine-agarose for the abridged clones (16a) dG17.44, (16b) dG4.48, (16c) dG21.52, and (16d) dG15.42.

FIGS. 17a–17d depicts the Elution profile for clone dG17.44 on affinity columns containing (17a) dAMP, (17b) dGMP, (17c) TPM, and (17d) dCMP.

Figure 18:
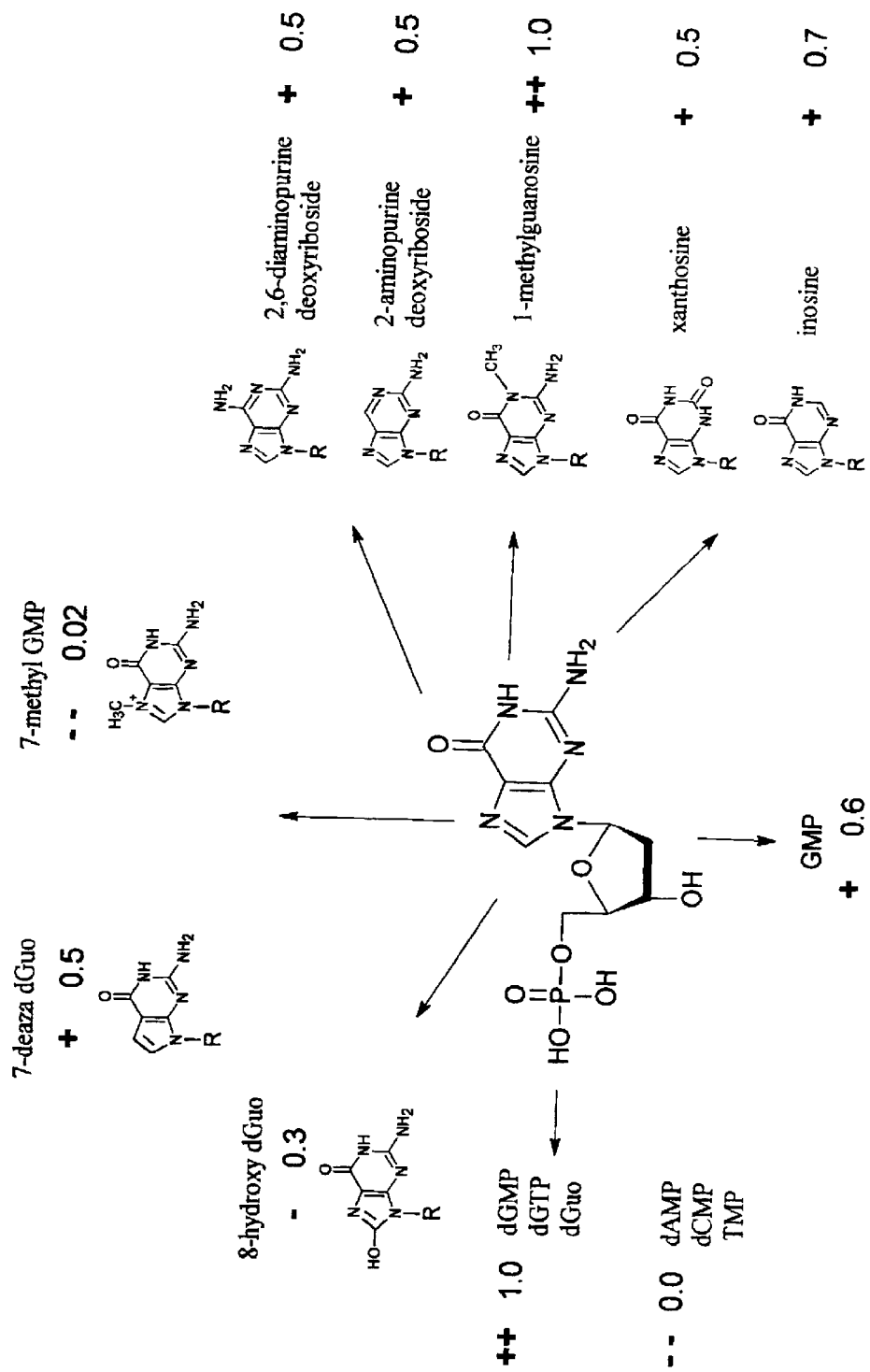

FIG. 18 depicts the relative binding affinities of various G-analog nucleotides and nucleosides for dGMP-aptamer clone dG17.44.

Figure 19:
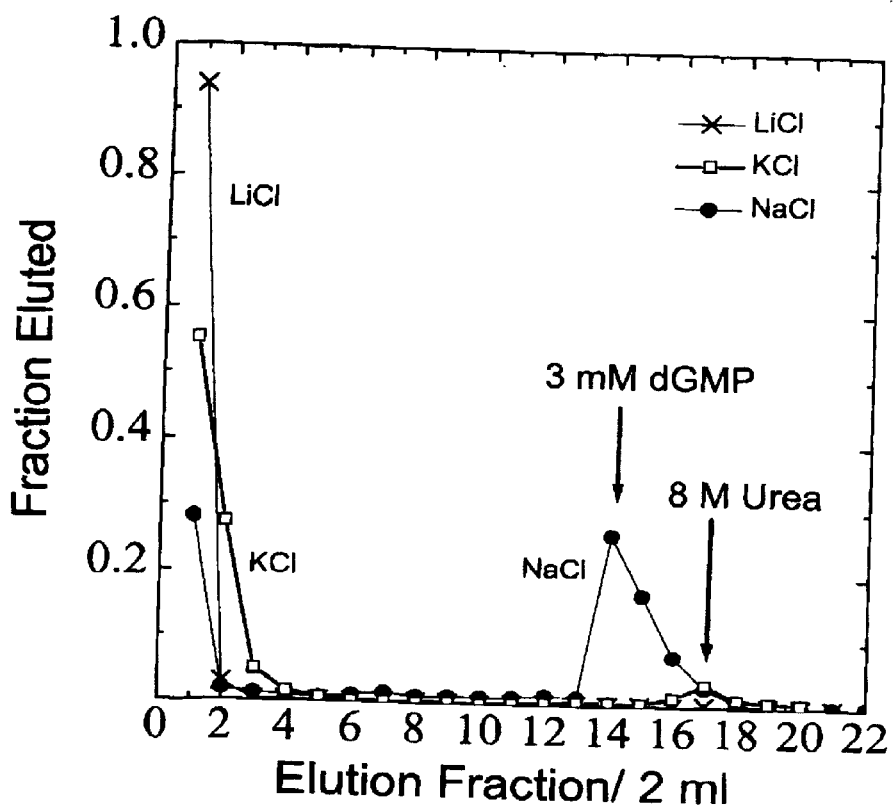

FIG. 19 depicts the elution profile for clone dG17.44 in buffer containing either LiCl, KCl, or NaCl.

Figure 20:
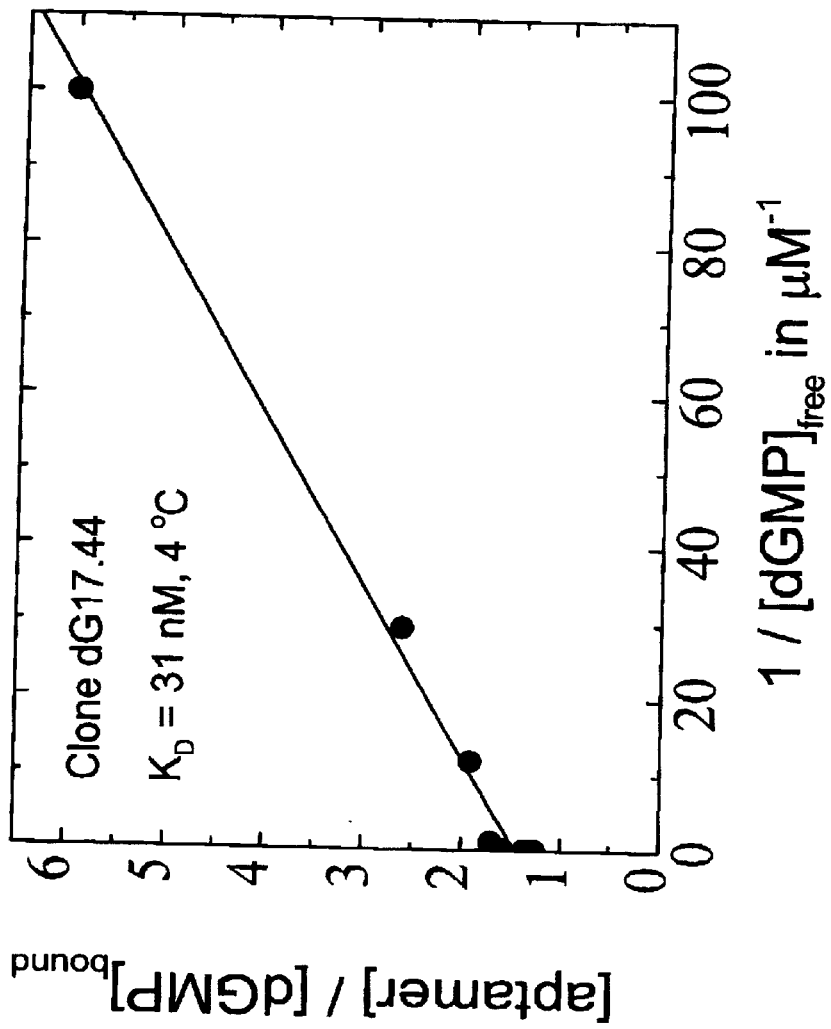

FIG. 20 depicts the solution binding titration based on analytical ultrafiltration for binding of dGMP and clone dG17.44 at 4° C.

Figure 21:
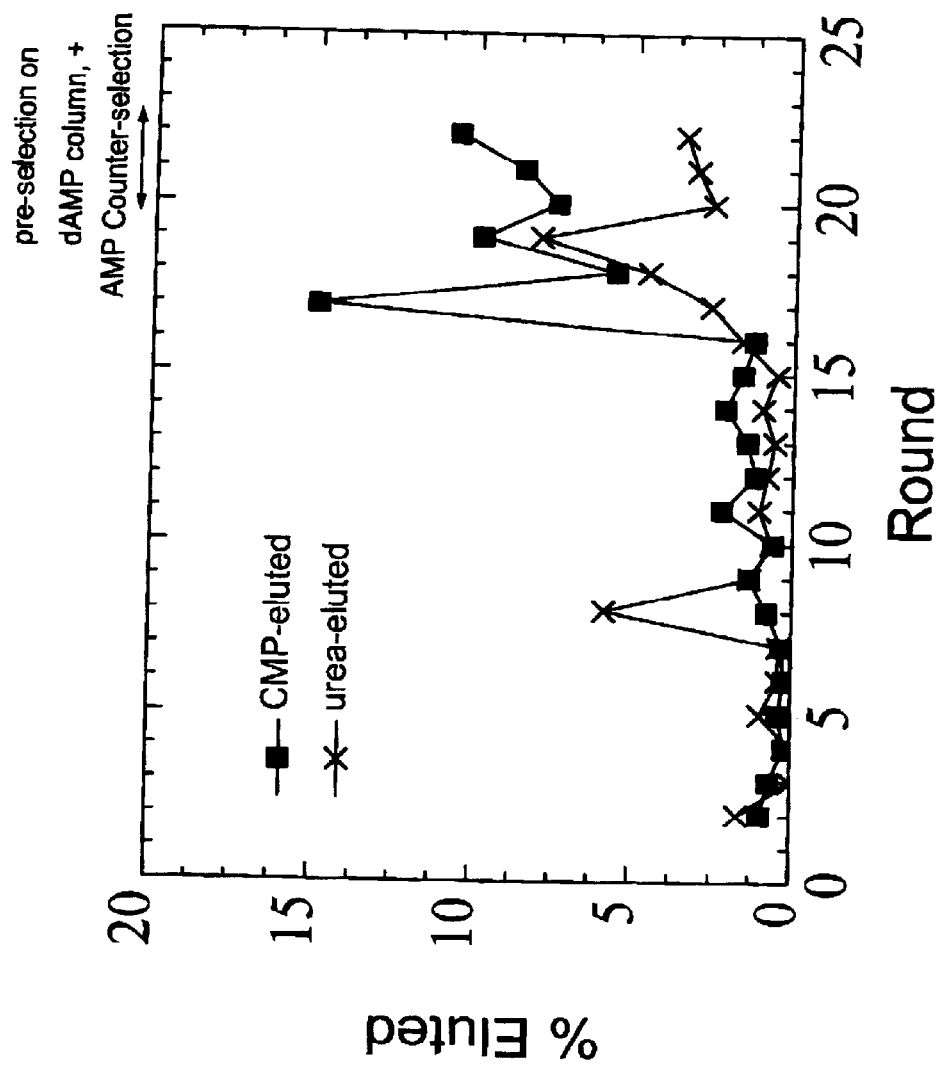

FIG. 21 depicts the fraction of DNA eluted either specifically by CMP, or non-specifically by urea, versus selection round.

Figure 22:
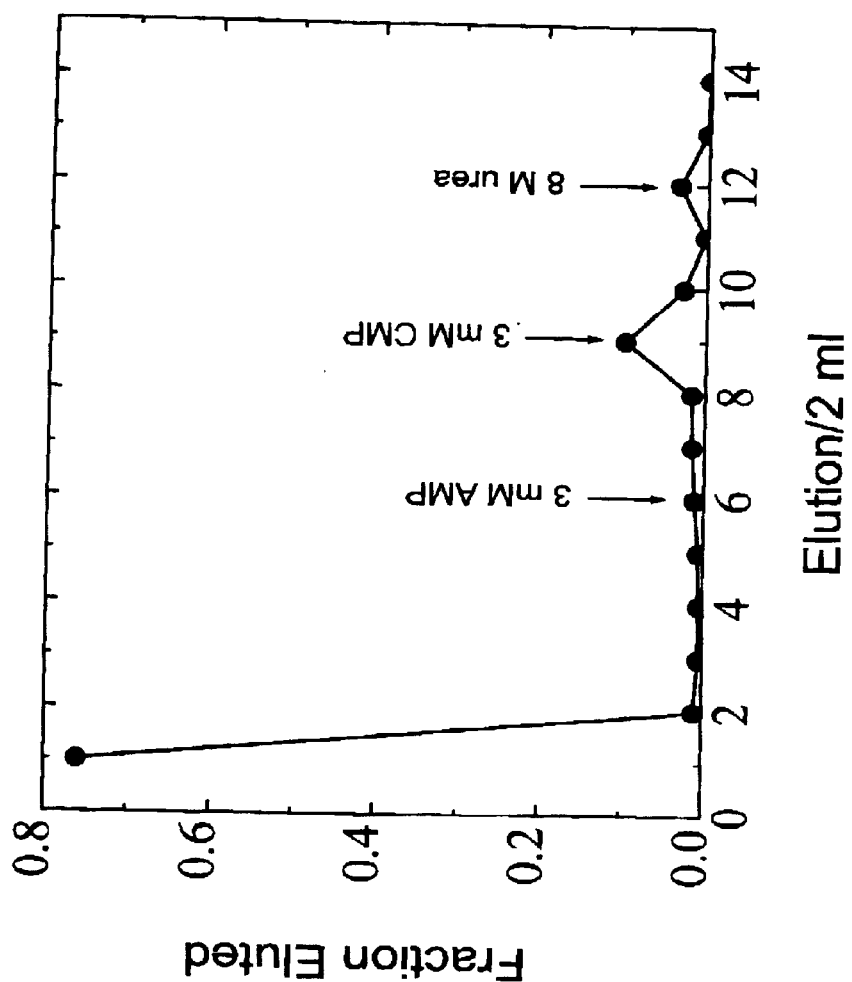

FIG. 22 depicts the elution profile of Round 22 selection for a CMP-agarose column.

FIGS. 23a–23b discloses the (23a) arsequence of clones obtained from Round 22 CMP selection, and (23b) sequence of abridged clones. Clone sequence is composed of fixed sequence (lower case), variable sequence (uppercase), and highly conserved or consensus sequence (boldtype). The sequences have been assigned the following sequence identifier numbers:

| Sequences | Sequence Identfiers |
|---|---|
| C3 | SEQ ID NO:59 |
| C10 | SEQ ID NO:60 |
| C30 | SEQ ID NO:61 |
| C9 | SEQ ID NO:62 |
| C25 | SEQ ID NO:63 |
| C12 | SEQ ID NO:64 |
| C8 | SEQ ID NO:65 |
| C32 | SEQ ID NO:66 |
| C29 | SEQ ID NO:67 |
| C6 | SEQ ID NO:68 |
| C1 | SEQ ID NO:69 |
| C38 | SEQ ID NO:70 |
| C21 | SEQ ID NO:71 |
| C17 | SEQ ID NO:72 |
| C5 | SEQ ID NO:73 |
| C2 | SEQ ID NO:74 |
| C3.48 | SEQ ID NO:75 |
| C9.58 | SEQ ID NO:76 |

Figure 24:
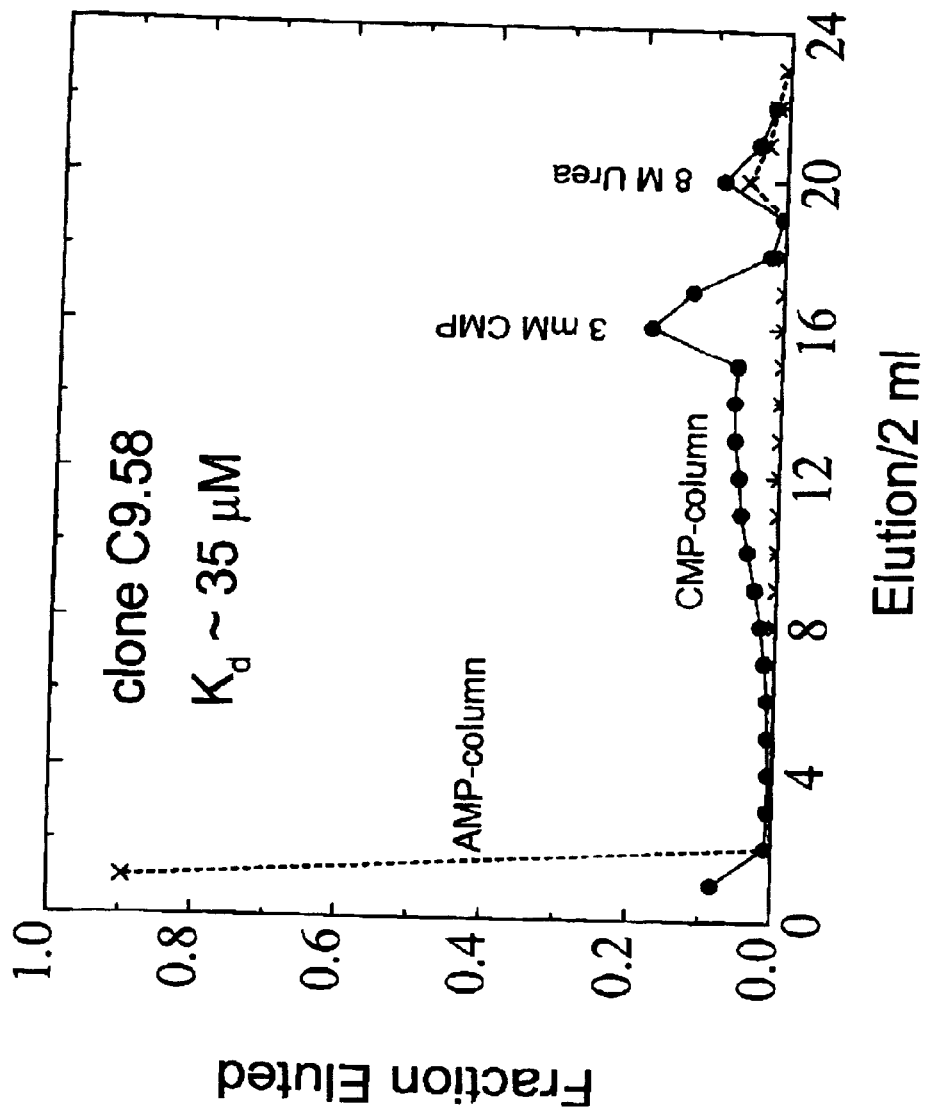

FIG. 24 depicts the elution profile of the CMP-aptamer clone C9.58 on either a CMP- or AMP-agarose affinity column.

Figure 25:
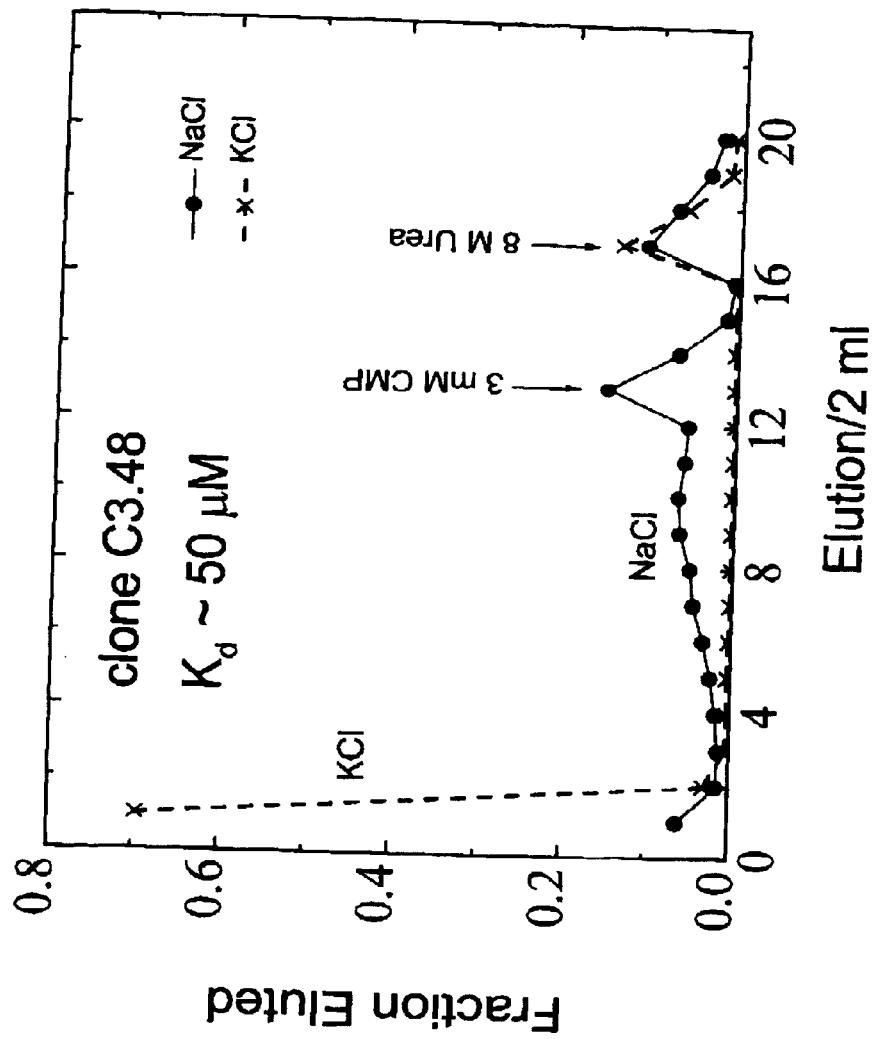

FIG. 25 depicts the elution profile of the CMP-aptamer clone C3.48 on a CMP-agarose affinity column in column-buffer containing either NaCl or KCl.

Figure 26:
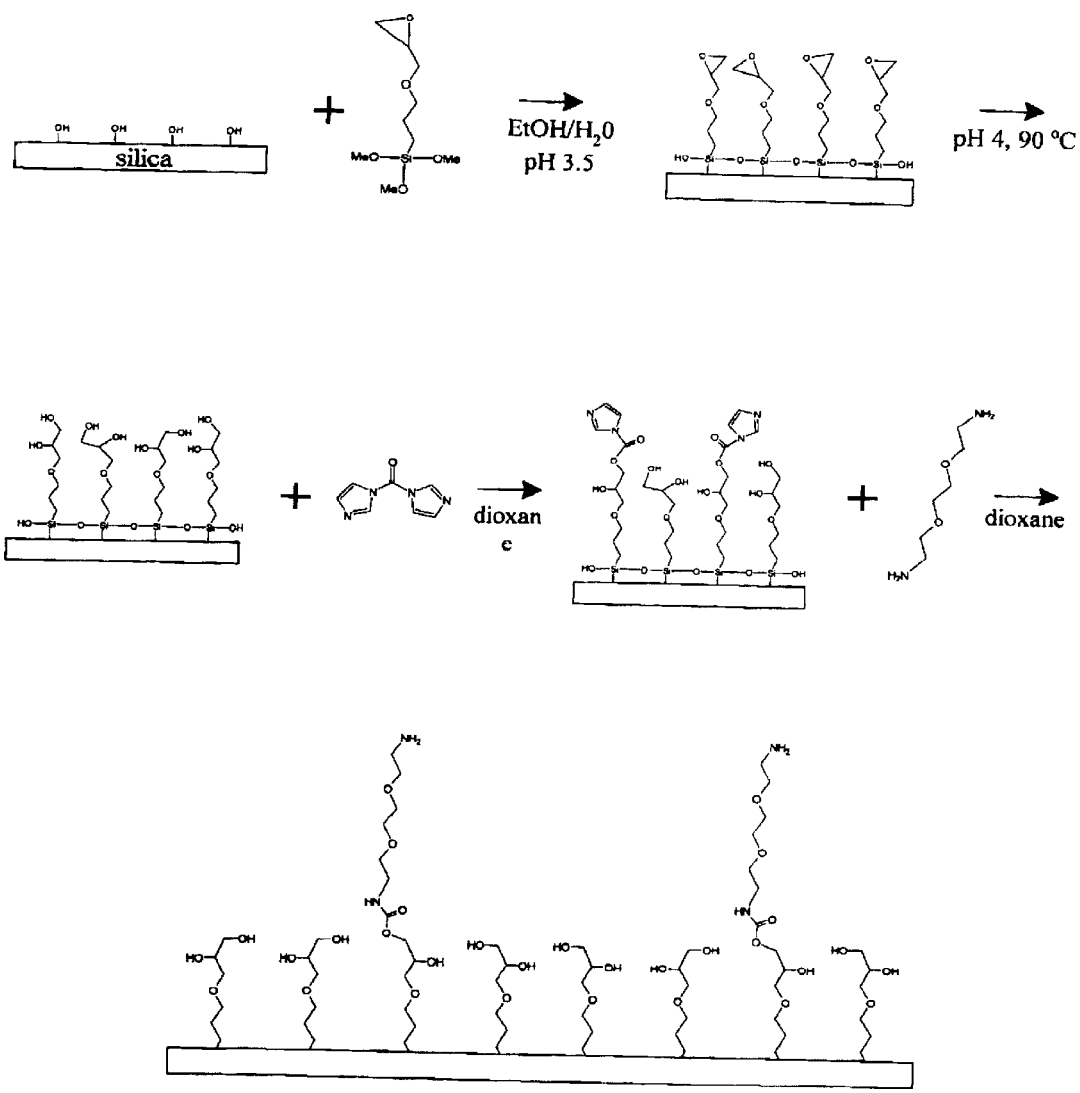

FIG. 26 depicts the steps involved to fabricate silica surfaces with amine-terminated linkers, for subsequent covalent coupling of nucleotides, that exhibit very low non-specific binding of aptamers.

Figure 27:
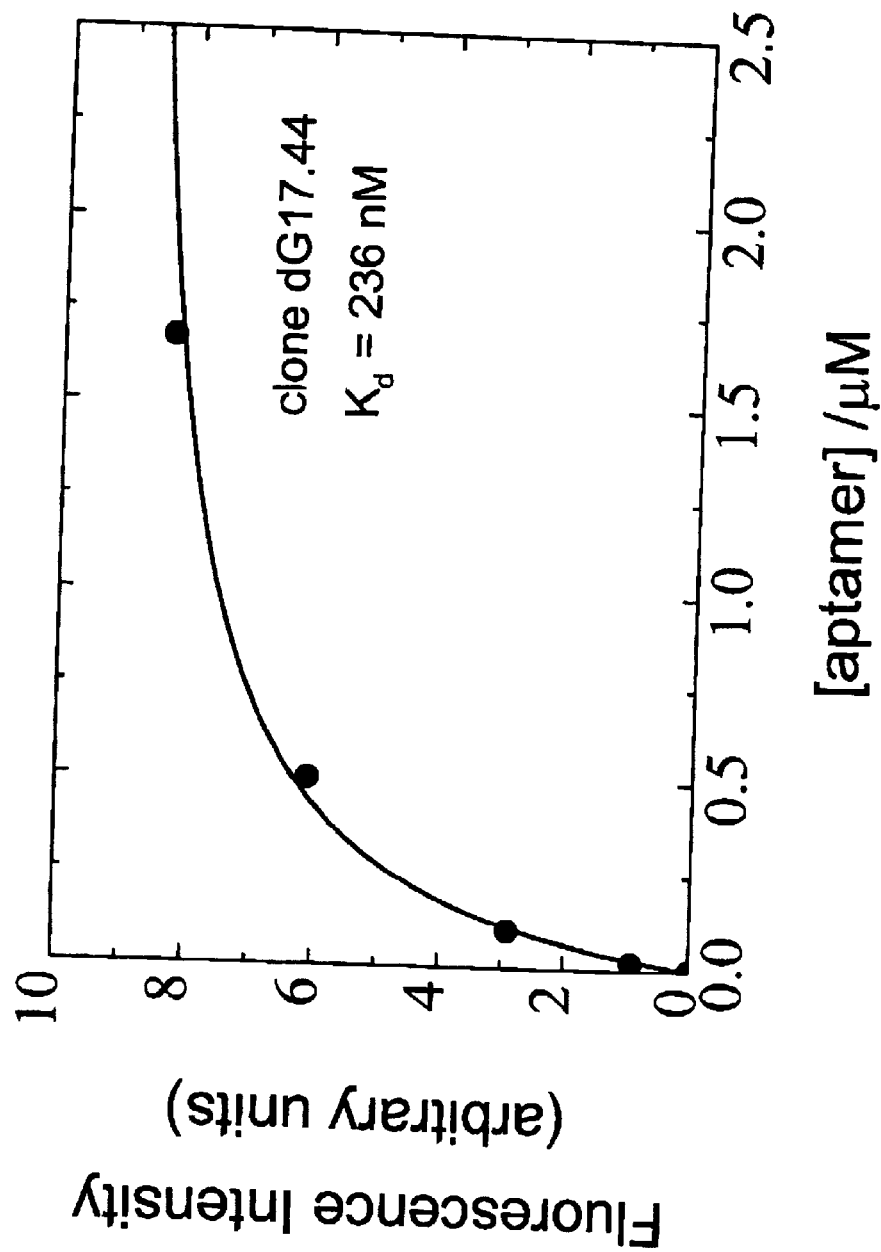

FIG. 27 depicts the equilibrium binding curve of a dGMP-aptamer (clone dG17.44) binding to surface-bound dGMP.

FIG. 28 discloses fluorescence images showing location of single dGMP molecules on a surface by binding dye-labeled aptamers (clone dG17.44 labeled with a single Cy5 dye). Surfaces are derivatized with either dCMP or dGMP as indicated.

DETAILED DESCRIPTION OF THE INVENTION

The present invention provides methods for sequencing or structually characterizing a polymeric biomolecule using an aptamer, a method for producing an aptamer for recognizing the base of a nucleotide and aptamers produced by the method.

Structural information derived from the results of the method of this invention includes information about any of the following attributes of the primary structure of the polymeric biomolecule which can be derived from the interaction of the aptamer with a monomer of the polymeric biomolecule, e.g., the monomeric composition of the biomolecule and the order in which the monomers are linked, including the presence of any branched structures; the linkage positions between the monomers; and the linkage configuration.

A polymeric biomolecule according to this invention is a molecule which comprises monomers covalently linked together such as nucleic acids, polypeptides, polysaccharides. In a preferred embodiment, the polymeric biomolecule is an nucleic acid (RNA or DNA), a polypeptide or a polysaccharide. A polymeric biomolecule used in this invention includes long chain biomolecules, e.g., DNA molecules 50,000 base pairs in length as well as oligomers such as oligosaccharides, oligonucleotides and peptides which are approximately 100 monomers or less in length. A polymeric biomolecule according to this invention may be artificially synthesized, isolated from nature or modified for ease of use in the methods of this invention (e.g., polysaccharides may be neutralized by mild acid or neuraminidase to remove sialic acid, by alkaline phosphatase to remove phosphate, or with sulfatases or by chemical means to remove sulfate). A polymeric biomolecule according to this invention may be bound to another molecule to form, for example, a glycolipid or a glycoprotein. In this case, the polymer to be analyzed according to the methods of this invention may be cleaved off of the molecule to which it is anchored by methods known in the art or may be analyzed while still attached to the molecule to which it is anchored.

An aptamer according to this invention is a small single stranded nucleic acid molecule approximately 10–120 nucleotides or 20–50 nucleotides that forms secondary and/or tertiary structures which allows it to bind to a monomer of a polymeric biomolecule of this invention. Preferred aptamers of this invention are those that have high affinities, with equilibrium dissociation constants ranging from 100 micromolar to sub-nanomolar depending on the selection used, and/or have high selectivity. In a preferred embodiment for the sequencing method according to this invention, aptamers with equilibrium dissociation constants less than 3 $\mu$M are used.

Aptamers according to this invention may be modified to improve binding specificity or stability as long as the aptamer retains a portion of its ability to bind and recognize its target monomer. For example, methods for modifying the bases and sugars of nucleotides are known in the art. Typically, phosphodiester linkages exist between the nucleotides of an RNA or DNA. An aptamer according to this invention may have phosphodiester, phosphoroamidite, phosphorothioate or other known linkages between its nucleotides to increase its stability provided that the linkage does not substantially interfere with the interaction of the aptamer with its target monomer.

An aptamer suitable for use in the methods of this invention may be synthesized by a polymerase chain reaction (PCR), a DNA or RNA polymerase, a chemical reaction or a machine according to standard methods known in the art. For example, an aptamer may be synthesized by an automated DNA synthesizer from Applied Biosystems, Inc. (Foster City, Calif.) using standard chemistries.

According to this invention, an aptamer useful for recognizing and binding a AMP or a dAMP is a nucleic acid molecule comprising the DNA sequence:

5'-CGGRGGAGGNACGGRGGAG-3' (SEQ ID NO:1),
wherein R is G or A and N is T, C, A or G. Examples of such aptamers include SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO:35 and SEQ ID NO:36, Another aptamer that recognizes and binds a AMP or dAMP is SEQ ID NO:17. Hereinafter, SEQ ID NO: 1 will also be referred to as the consensus sequence for the A aptamer.

According to this invention, an aptamer useful for recognizing and binding a CMP or a dCMP is a nucleic acid molecule comprising the DNA sequence:

5'-GGGAGGGTN$_1$N$_2$N$_3$GGN$_4$G-3' (SEQ ID NO:2),
wherein N$_1$, N$_2$, N$_3$, and N$_4$ is any monomer selected from the group consisting of A, C, G and T. In a preferred embodiment, N$_4$ is T or C. Examples of sequences of such molecules include SEQ ID NO:59, SEQ ID NO:60, SEQ ID NO:61, SEQ ID NO:62, SEQ ID NO:63, SEQ ID NO:64, SEQ ID NO:66, SEQ ID NO:67; SEQ ID NO:75 and SEQ ID NO:76.

Another aptamer useful for recognizing and binding CMP or dCMP is a nucleic acid molecule comprising the DNA sequence:

5'-GGT N$_1$N$_2$N$_3$GGN$_4$G-3' (SEQ ID NO:3)
wherein N$_1$, N$_2$, N$_3$, and N$_4$ is any monomer selected from the group consisting of A, C, G and T. Examples of sequences of such aptamers include SEQ ID NO:70, SEQ ID NO:71, SEQ ID NO:72; SEQ ID NO:73 or SEQ ID NO:74. Other sequences for making aptamers that are useful for recognizing and binding a CMP or dCMP include SEQ ID NO:65, SEQ ID NO:68 and SEQ ID NO:69. Hereinafter, SEQ ID NOs:2 and 3 will also be referred to as the consensus sequences for the C aptamer.

According to this invention, an aptamer useful for recognizing and binding a GMP or a dGMP is a nucleic acid molecule comprising a DNA sequence 5'-TGGGN$_1$TGGGN$_2$N$_3$TGGGN$_4$AGGGT-3' (SEQ ID NO:4 or SEQ ID NO:90),
wherein N$_1$, N$_2$, and N$_4$ is any monomer selected from the group consisting of A, C, G and T and N$_3$ is no momomer or any monomer selected from the group consisting of A, C, G and T. Examples of sequences of such aptamers include SEQ ID NO:37, SEQ ID NO:38, SEQ ID NO:39, SEQ ID NO:42; SEQ ID NO:44, SEQ ID NO:46, SEQ ID NO:47, SEQ ID NO:49, SEQ ID NO:54, SEQ ID NO:55, SEQ ID NO:56 and SEQ ID NO:57. Other sequences that are useful for making aptamers for recognizing and binding a GMP or dGMP include SEQ ID NO:40, SEQ ID NO:41, SEQ ID NO:43, SEQ ID NO: 45; SEQ ID NO:48; SEQ ID NO:50, SEQ ID NO:51, SEQ IS NO:52, SEQ ID NO:53 and SEQ ID NO:58. Hereinafter, SEQ ID NO: 4 will also be referred to as the consensus sequence for the G aptamer.

To improve binding specificity, affinity and/or stability of the aptamers comprising SEQ ID Nos. 1–4, the nucleic acid molecule may be engineered to further contain sequences upstream and downstream of any one of consensus sequences described above (hereinafter, 5' flanking region and 3' flanking region, respectively) to have Watson-Crick base pairing complementarity with each other. Generally, a useful 5' flanking region according to this invention will have several contiguous base pairs that are complementary to the 3' flanking region. The optimal 5' and 3' flanking regions for increasing the binding affinity, specificity and/or stability of the aptamer may be determined by preparing an aptamer pool comprising aptamers with a fixed DNA sequence for the consensus region and randomized DNA sequences for the flanking regions, and separating and amplifying the desired aptamer using the methods of this invention.

In one embodiment, the nucleic acid molecule comprising SEQ ID NO:1 further comprises a 5' flanking region comprising the DNA sequence 5'-CCTACT-3' and a 3' flanking region comprising the DNA sequence 5'-AGTAGG-3'. In another embodiment, the nucleic acid molecule comprising SEQ ID NO:1 further comprises a 5' flanking region comprising the DNA sequence 5'-AGATG -3' and a 3' flanking region comprising the DNA sequence 5'-CATCG-3'. In one preferred embodiment, the DNA sequences flanking SEQ ID NO:1 is 5'-GCCTCATGTCGAACCTACTGGA-3' (SEQ ID NO:77) and 5'-GGAAGTAGGTGAGGGAG-3' (SEQ ID NO:78) upstream and downstream, respectively.

In another embodiment, the aptamer comprising SEQ ID NO:2 further comprises a 5' flanking region comprising the DNA sequence 5'-TCATGTCGAAGGGGCGTATGGGCTTTG-3' (SEQ ID NO:79) and a 3' flanking region comprising the DNA sequence 5'-ACATGT-3'. In another embodiment, the aptamer comprising SEQ ID NO:2 further comprises a 5' flanking region comprising the DNA sequence TGATCCGCGGCAGTGC-3' (SEQ ID NO:80) and a 3' flanking region comprising the DNA sequence 5'-TGCTTGGAGCAATGGCGATGACGGATC-3' (SEQ ID NO:81).

In another embodiment, the aptamer comprising SEQ ID NO:4 further comprises a 5' flanking region comprising the DNA sequence 5'-AGTGACACCAC-3' (SEQ ID NO:82) and a 3' flanking region comprising the DNA sequence 5'-TGTGGAATCAC-3' (SEQ ID NO:83). In another embodiment, the aptamer comprising SEQ ID NO:4 further comprises a 5' flanking region comprising the DNA sequence 5'-AGATCGCCATAAG-3' (SEQ ID NO:84) and a 3' flanking region comprising the DNA sequence 5'-GGAGCAATGGCGAT-3' (SEQ ID NO:85).

Selection of aptamers suitable for use in the methods of this invention may be derived by creating an affinity column with a monomer of the polymeric biomolecule attached to it, screening mixtures of random aptamers using the affinity column, and then amplifying the aptamers that bound, e.g., following the methods of Gold, et al. (U.S. Pat. No. 5,270,163) which describes the "SELEX" (Systematic Evolution of Ligands by Exponential Enrichment) method.

The sequencing method according to this invention comprises the step of separating a terminal monomer from the polymeric biomolecule. The separation step comprises using a cleaving reagent to catalyze the hydrolysis of the terminal monomer from the polymeric biomolecule.

In a preferred embodiment of this invention, the method for structurally characterizing the polymeric biomolecule comprises the step of cleaving one or more linkages between the monomers using a cleavage reagent. Thus, a cleavage reagent according to this invention can act by liberating monomers at either termini of the polymeric biomolecule, or by breaking internal bonds thereby generating fragments or single monomers of the subject polymeric biomolecule. Typically, the bond is a peptide bond for a polypeptide, a glycosidic bond for a polysaccharide, or a phosphodiester bond for a nucleic acid. A cleavage reagent for the structural characterizing method may interrupt the primary sequence by cleaving before or after a specific monomer(s) or may cleave between all the monomers of the polymeric biomolecule. The cleavage reagent(s) useful according to the methods of this invention will depend upon the nature of the polymer and the sequence or type of structural information desired. Several cleaving reagents are known in the art for polymeric biomolecules.

When the biomolecule is to be sequenced according a method of this invention, the preferred cleavage reagent is an exohydrolase (i.e., cleaves the linkage between the terminal monomer and the adjacent monomer). For example, when the biomolecule to be sequenced is a polypeptide the preferred cleavage reagent is a mono-exopeptidase. Exopeptidases may cleave at the carboxy terminus (carboxypeptidases) or the amino-terminus (aminopeptidases) of a polypeptide. Exopeptidases may be mono-peptidases and poly-peptidases, such as di-peptidases and tri-peptidases. This invention contemplates, in one particular aspect of this invention, the use of carboxypeptidase Y, carboxypeptidase P, carboxypeptidase A and carboxypeptidase B. Also contemplated is the use of aminopeptidases, such as leucine aminopeptidase, microsomal peptidase, aminopeptidase 1, LAP, proline aminodipeptidase and cathepsin C and so forth. Exopeptidases are commercially available, for example from reagent suppliers such as Sigma Chemicals (St. Louis, Mo.) and Oxford Glycosystems (Rosedale, N.Y.).

Preferred exoglycosidases for polysaccharide sequencing include but are not limited to alpha-Mannosidese I, alpha-Mannosidese, beta-Hexosaminidese, beta-Galactosidase, alpha-Fucosidase I and II, alpha-Galactosidase, alpha-Neuraminidase and, alpha-Glucosidase I and II. Representative lists of useful exoglycosidases may be found, for example, in A. Kobata, Anal. Biochem., 100, 1 (1979), R. Parekh et al., PCT Application No. WO 92/19768 (Nov. 12, 1992), T. W. Rademacher et al., U.S. Pat. No. 5,100,778 (Mar. 31, 1992), and R. J. Linhardt et al., U.S. Pat. No. 5,284,558 (Feb. 8, 1994), Kobata, A., in Biology of Carbohydrates, Volume 2, V. Ginsburg et al., ed., John Wiley & Sons, New York, pp. 88 ff (1984)) all of which are incorporated herein by reference. It is to be understood that these lists are illustrative only and in no way limit the selection of exoglycosidases used herein.

Preferred exonucleases for nucleic acid sequencing include, but are not limited to lambda-exonuclease, t7 Gene 1 exonuclease, exonuclease III, exonuclease I, exonuclease V, exonuclease II, DNA polymerase II, venom phosphodiesterase, spleen phosphodiesterase, Bal-31 nuclease, E. coli exonuclease I, E. coli exonuclease VII, Mung Bean Nuclease, S1 Nuclease, an exonuclease activity of E. coli DNA polymerase 1, an exonuclease activity of a Klenow fragment of DNA polymerase 1, an exonuclease activity of T4 DNA polymerase, an exonuclease activity of T7 DNA polymerase, an exonuclease activity of Taq DNA polymerase, an exonuclease activity of DEEP VENT DNA polymerase, and an exonuclease activity of VENTR DNA polymerase.

The cleavage reagent according to this invention may alternatively be a chemical compound, such as those known in the art for catalyzing the cleavage of the terminal monomers of polymeric biomolecules or partial or total cleavage of all the linkages between the monomers of the polymeric biomolecules. See, supra, background section of this application. Currently preferred agents other than an enzyme include but are not limited to: cyanogen bromide, hydrochloric acid, sulfuric acid, and pentafluoroproprionic fluorohydride. In some embodiments, hydrolysis can be accomplished using partial acid hydrolysis in accordance with the methods disclosed herein.

Any of the aforementioned cleavage reagents may be suitable for elucidating the structure of the polymeric biomolecule according to the method of this invention. Enzymes which may degrade the linkages between the internally located monomers of the polymeric biomolecules are known, for example, endonucleases, endopeptidases, and endogycosylases (e.g., A. Kobata, Anal. Biochem., 100, 1 (1979)). The instant method provides for the use of combinations of the above-described individual cleaving agents to structurally characterize the polymeric biomolecules. For example, chemical cleaving agents may be used with enzymatic cleaving agents or enzymatic cleaving agents from one class or different classes may be used together (e.g., a mixture of exonucleases versus a mixture of an endoprotease and a endopeptidase). Two or more cleaving agents may be used simultaneously or sequentially on a polymeric biomolecule. The exact combination and the circumstances under which such a combination is appropriate will depend upon the nature of the polymer and the information desired.

The methods of the invention is useful for polymeric biomolecules of either known or unknown structure. In the case of a known or putative structure, as where synthetic polymeric biomolecules are obtained from a commercial supplier or isolated from a glycoprotein of known or suspected structure, a combination of cleavage agents can be designed to verify or confirm the putative structure or sequence. For example, an enzymatic array may be designed to cleave verify or confirm the structure of a polysaccharide, as described in U.S. Pat. No. 5,753,454 (Lee) incorporated by reference. If the oligosaccharide of unknown structure is known to be an N-linked oligosaccharide, knowledge of the common core structure of N-linked oligosaccharides, as described above, can be used to design a suitable enzyme array.

The term "array" is used to convey the underlying principle of the cleavage protocol utilized in U.S. Pat. No. 5,753,454 (Lee) and further described as "Reagent Array Analysis" in Rademacher et al., U.S. Pat. No. 5,100,778 (Mar. 31, 1992), incorporated herein by reference. Essentially, two or more suitable cleaving agents are selected, and an array of reagents is prepared such that each reagent lacks one of the selected cleaving agents. In a variation of the invention, one or more reagents can lack two of the selected cleaving agents. Each aliquot is then reacted with a different reagent to cleave the polymeric biomolecule and produce a plurality of cleaved products. The reaction is typically carried out for a predetermined amount of time, or to a predetermined end point, such that the reaction is carried to completion. This method is particularly useful for sequencing according to the method of this invention. The released fragments or monomers are separated and/or deposited onto a surface for analysis by aptamers which recognize the monomers or monomers within the fragments.

In one preferred embodiment of this invention, polymeric biomolecules are sequenced or characterized by (a) a separation step comprising: cleaving the polymeric biomolecule which is attached to a solid support, transporting the cleaved fragment or monomer away from the uncleaved portion of the polymeric biomolecule; and depositing the cleaved fragment or monomer onto a surface; and (b) a detection step comprising the binding of aptamers to the monomers on the surface or the monomers in the fragment. In one embodiment of this invention, the polymeric biomolecule is covalently attached to the solid support. In another embodiment, the polymeric biomolecule is attached to the solid support through a biotin-streptavidin interaction. In another preferred embodiment of this invention, a mixture of exohydrolases such as a mixture of exoglycosidases or a mixture of carboxyexopeptidases are exposed to the polysaccharide or polypeptide, respectively, under conditions which allow processive degradation of the polymer from one terminus. In another preferred embodiment of this invention, DNA sequencing is performed according to the method provided in U.S. Pat. No. 5,674,743 (Ulmer) (incorporated by reference) except that the detection step comprises binding aptamers labeled with an optically detectable species to each separated nucleotide and detecting each separated nucleotide by the spectrosopic emission of the label.

Solid supports useful for binding to a polymeric biomolecule according to this invention will depend upon the type of polymeric biomolecule being analyzed and the type of method being performed. For example, for carboxypeptidase sequencing, the polypeptide of interest should not be attached to the solid support at or near its C-terminus. Solid supports useful for binding to polysaccharides, polypeptides, and nucleic acids are known in the art, e.g., glass beads, cellulose beads, polystyrene beads, SEPHADEX beads, SEPHAROSE beads, polyacrylamide beads and agarose beads (e.g., Ghosh, S. S. and Musso, G. F., "Covalent Attachment of Oligonucleotides to Solid Supports," Nucleic Acids Research. 15:(13) 5353–5372 (1987); U.S. Pat. No. 4,992,383 (Farnsworth); incorporated by reference). In one embodiment, the polymeric biomolecule is covalently attached to the solid support. In another embodiment, the polymeric biomolecule is attached to the support through a biotin-streptavidin interaction.

The aptamers used in the sequencing or physical characterization methods of this invention may be labeled or may be tagged (e.g., biotinylated), but the label or tag should not substantially interfere with the interaction of the aptamer with the cleaved monomer or fragment. Alternatively, to boost the signal derived from the binding of the aptamer to the monomer of the polymeric biomolecule and/or increase the sensitivity of the method, the methods of this invention may additionally comprise the step of contacting a secondary factor to the aptamer that is bound to the monomer. This secondary factor, for example, may be an aptamer, an antibody, a protein or a compound which is labeled and recognizes the aptamer or a tag which is bound to the aptamer. Preferably, a label according to this invention is an optically detectable species such as fluorophore. In one embodiment, such as for sequencing DNA, aptamers for each nucleotide shall be labeled with a different fluorophore. The aptamers may optionally have two or more of the same fluorophores attached to them. Preferably, such as for sequencing, the wavelength emissions of each fluorophore should be measurably distinct from each other so as to facilitate identification of the cleaved nucleotide. Fluorophores useful in the methods of this invention are commercially available such as TAMRA, Hoechst dye, fluorescein, rhodamine, Texas Red, or the 40 nm fluorescent beads sold by Molecular Probes TransFluoSpheres, which can attached to an aptamer or protein by standard methodologies. Dye labels may be laser-excited using confocal, evanescent-wave or other geometries for low background detection of the individual labels.

In a preferred embodiment of this invention, the steps of the sequencing method or the physical characterization method are optimized for automation. In another preferred embodiment of this invention, the cleaved monomer or the released portion of the polymer biomolecule is deposited onto a surface in an orderly manner such that it is separated from prior and subsequently cleaved monomers/released portions of biomolecule. A mixture of aptamers, at least one of which is expected to bind to a monomer, can be applied to the surface having the cleaved monomer or released portion of biomolecule under conditions which favor aptamer binding. The surface onto which the monomer is deposited may be washed before and after an aptamer is bound to the monomer or released portion of the biomolecule. Then, the identity of the aptamer can be determined as described above.

In a preferred embodiment, the surfaces according to this invention which bind the cleaved monomer have been prepared to bind the cleaved monmer in an orderly fashion. For example, the surface will have binding sites for the monomer. In a preferred embodiment, the binding site is situated such that a nucleotide will bind to it through its 5' phosphate group thereby forming a phosphoroamidite bond. In a further embodiment, the surface will be treated to reduce non-specific binding, e.g., treated with polyethylene glycol. In a further embodiment of this invention, the surface is patterned so as to facilitate containment of the cleaved monomer to a region on the surface and/or create a reaction chamber to facilitate the binding of the monomer to the pre-treated surface.

Preferably, fluorescent autoradiation from the label on the aptamer, protein or compound used in the methods of this invention will be detected by a microscope. The emitted autoradiation may be directed by the microscope onto detection elements such as a charged-coupled device (CCD) camera. For example, in the sequencing method according to this invention, the microscope may have four unique optical filters each connected to a CCD camera such that only one of the four dyes used with each aptamer will be recorded by each CCD camera. The CCD camera will then convert the emitted autoradation into an electrical signal which is read by a computer. Framing times can be faster than one field-of-view per second, i.e., 25 bases/second per strand of DNA. A 50 kB DNA strand may take approximately 30 minutes to read.

One example of the DNA sequencing envisioned by this invention described below. Base-at-a-time sequencing of DNA is accomplished by the sequential and repeated enzymatic hydrolysis of the terminal nucleotide of a strand of DNA whose sequence of bases is to be determined. The DNA strand is held fixed at the end distal to the enzymatic hydrolysis in a channel containing aqueous buffer under laminar flow conditions. Nucleotides released following enzymatic hydrolysis are entrained in the flowing buffer, and move away from the stationary DNA at an average speed determined by the buffer flow speed. The channel containing the single DNA strand additionally acts as a dispenser of the flowing buffer into isolated drops onto a moving nucleotide-capture surface. Drop isolation prevents any mixing of a nucleotide from one drop to another, thus preserving their order. To minimize the probability that two nucleotides end up in one drop (thereby confusing their order), this channel dispenser divides the flowing buffer between entrained nucleotides into approximately 3–10 drops; i.e. more drops than nucleotides, to insure that any two sequential nucleotides are spaced apart by drops containing no nucleotides. The dimensions of the channel, the speed of the buffer flow, the speed of the moving capture surface, the drop volume, and the rate of enzymatic digestion are all chosen to provide drops on the surface which preserve the order of hydrolyzed nucleotides at a spacing larger than the resolution of the detection apparatus, typically greater than 0.5 microns. This process of hydrolysis of nucleotides into flowing buffer that is subsequently dispensed onto a moving surface is continued until the full length of the DNA strand in question is digested. Preferably, the process is multiplexed, so that a plurality (Nchannels, each with one DNA strand and side-by-side, dispense drops onto the nucleotide-capture surface in N separate lanes, each lane containing the nucleotides from only one DNA stand. Subsequent parallel processing and readout of the surface-bound nucleotides greatly improves the effective sequencing rate.

The use of the nucleotide-capture surface provides a potentially permanent physical recording of the order of nucleotide molecules from the DNA strand whose sequence was in question. To make a permanent record which can subsequently be washed and otherwise be treated in batch format, the nucleotides are covalently coupled to the surface. The surface substrate is preferably silica, silicon, glass, or plastic, functionalized to enable covalent coupling of nucleotides. Functionalized surfaces made be obtained using conventional silanization methods to incorporate reactive groups, or by thin-film deposition of polymers containing reactive functional moieties. The functional group is chosen to facilitate covalently binding of nucleotides, preferably through the phosphate or hydroxyl group of the nucleotide sugar, i.e. a group common to a nucleotide of any base, either directly as a consequence of droplet evaporation, or from droplet solution by the action of a coupling reagent, that is either present on the surface prior to drop dispensing, or mixed into the flowing buffer prior to drop dispensing, or added after the drop has been dispensed. Preferably, the surface is otherwise passive to the absorption of nucleotides, or reagents that detect nucleotides. Preferably, the functional group is an amine that terminates a surface-bound linker, to which the nucleotide is covalently coupled in the presence of imidazole and a carbodiimide, e.g., EDAC. See Example 4. The surface may additionally be patterned to help maintain or contain the drops from the dispenser. Patterns of hydrophillic patches separated by hydrophobic regions, or patterns of surface depressions (nanowells) serve this purpose, and can be obtained by replication from a master generated by standard lithographic techniques.

The steps for detecting and identifing the nucleotides spatially to determine their sequence could be carried out as follows. Base-specific nucleotide affinity reagents such as the aptamers are pooled into a solution, where each aptamer that binds a specific base has been synthesized to include a unique label, preferably a dye or group of dyes or dye FRET-dye pairs (Fluorescent Resonant Energy Transfer) that yield a distinguishable measurement, e.g. in their spectral or temporal fluorescence properties. The concentration of each type of aptamer is adjusted to be approximately 10–100 times the value of the equilibrium binding constant for its specific ligand nucleotide. The substrate containing the surface-bound nucleotides is incubated in the solution containing the pooled aptamers for a sufficient time to allow equilibrium to be reached. This surface is then washed free of solution phase aptamers and the weak, non-specifically-bound aptamers possibly on the surface. The wash time should be short enough so that specifically-bound aptamers are not removed in any significant number. The surface is then dried to immobilize the specifically-bound aptamers at the location of their respective nucleotide ligand. The substrate is then scanned under appropriate illumination, and the fluorescence from the dye-labeled aptamers recorded as a function of position on the surface. By discrimination of the fluorescence properties, a map of the identity and location of nucleotides on the surface is obtained, and thus of the sequence of the original DNA in question.

The present invention provides a method for producing an aptamer for recognizing a target monomer comprising the steps of(1) separating the aptamer from a mixture of aptamers by subjecting the mixture of aptamers to an affinity system comprising the target monomer at low temperature, (2) amplifying the aptamer that bound to the affinity system, and (3) repeating the separation and amplification steps until the aptamer having the desired affinity and selectivity for the target monomer is obtained. The low temperature referred to above is approximately a temperature between less than 10° C. to above freezing point. In one embodiment, the low temperature is 4° C. In a preferred embodiment, the temperature is closer to the freezing point.

An affinity system according to this invention is a system for selecting the aptamer for the target monomer by using the target monomer to bind to the desired aptamer and then eluting the desired aptamer from binding to the target monomer. For example, the affinity system may be a target nucleoside or nucleotide bound to a solid support. In a preferred embodiment, an affinity system according to this invention also comprises pre-selection and/or counterselection to screen out undesireable aptamers.

Pre-selection involves filtering out aptamers which bind to the matrix or solid support by, for example, exposing the aptamer pool to the solid support of the affinity sytem, wherein the solid support does not have target monomers bound to it.

Counterselection involves using a monomer of the polymeric biomolecule to be sequenced, other than the target monomer, or some part thereof, to bind and remove the undesirable aptamers. Undesireable aptmers are aptamers that bind to a monomer other than the target monomer and/or the matrix or solid support. Thus, aptamers that did not bind to the other monomer or part thereof or solid support, would be collected. For example, in order to obtain an aptamer with high selectivity to dAMP, one could counterselect with dCMP, dGMP and dTMP. The amplification step according to this invention is carried out by using polymerase chain reaction (PCR).

The present invention also provides a method for producing an aptamer useful for nucleic acid sequencing. Specifically, the method provides aptamers for recognizing the base of a target nucleotide comprising the step of partitioning the aptamer from a mixture of aptamers using an affinity system, wherein the affinity system comprises the target nucleotide attached to a solid support through the 5' carbon of the sugar ring of the target nucleotide. Preferably, the target nucleotide is attached to the solid support through the phosphate on the 5' carbon of the sugar ring to allow maximum interaction with the base and decreased background binding to the surface. The selected apatmer is then subjected to polymerase chain reaction (PCR) for amplification and converted to single-stranded DNA by asymmetric PCR. The single-stranded DNA is reformed into an aptamer, subjected to the same affinity system, eluted from the affinity system, amplified by PCR and converted into single-stranded DNA. This process is repeated for 11+ rounds.

In a particularly preferred embodiment, the target nucleotides are orientated and positioned on the solid support in approximately the same orientation and position that the cleaved nucleotides take on the surface in the above sequencing method, infra. In this way, the selection process and a sequencing method of this invention are "self-consistent" with each other.

In another preferred embodiment, the 5' end of the primer DNA used in the PCR reactions is labeled with a fluorophore such as N,N,N',N'-tetramethyl-6-carboxyrhodamine (TAMRA), to allow quantitative measurements of the amount of labeled aptamer DNA recovered during elution.

Preferred solid supports for selecting aptamers for nucleic acid sequencing are those that are capable of binding to the nucleotide through the phoshate on the 5' carbon of the sugar ring and exhibit little non-specific binding to nucleotides. In another preferred embodiment, the surface of the solid support is modified to reduce non-specific binding, for example using polyethylene glycols (PEG) (Sigal et al., (1996) Anal Chem, 68, 490–497). Other strategies for enhancing the affinities and selectivities of aptamers are known (Eaton et al., (1997) Biorg & Med Chem., 5, 1087–1096; Kawakami J, et al. (1997) Nucleic Acids Symp Ser., 37, 201–202).

The concentration of the nucleotide on the surface of the affinity column should be sufficient to isolate aptamers against the individual nucleotides without recovering aptamers against closely spaced dimers of nucleotide. Preferably, the concentration range of the nucleotides attached to the surface of the affinity column is 50 $\mu$M–500 $\mu$M (approximately 30 Angstrom to 300 Angstrom distance between nucletides). Preferably, the solid support columns used in the later rounds of selection have a decreasing concentration of target nucleotide attached to them.

In another preferred embodiment of the selection method, the mixture of aptamers is subjected to counter selection against the surface of the solid support alone and other non-target nucleotides before or after the aptamer mixture is passed through the affinity column to minimize the nonspecific binding of the selected aptamers. In a more preferred embodiment, the mixture of aptamers are subject to counter selection subsequent to the initial selection. Preferentially, such counter selection is be incorporated into the final selection rounds. Such counter selection will decrease the representation of cross reacting aptamers in the pool. Preferably, the selectivity of the aptamer exceed 100 fold for the target nucleotide over a non-target nucleotide (i.e. for 99% detection accuracy).

In one embodiment of the invention, the properties of the selected aptamer may be improved by replacing selected residues in the aptamer. For example, a pyrimidine may be replaced with a 2'fluoro-pyrimidine to increase the affinity of the aptamer. In another embodiment of the invention, the aptamer backbone may be replaced by phosphorothioate or phosphoroamidite to increase the stability of an aptamer or its affinity for its target. In another embodiment of this invention, mixtures of aptamers may be exposed to the target nucleotide and then subjected to crosslinking such that a covalent linkage is formed between the relevant aptamers and target nucleotides. However, the modifications to the DNA aptamer should not substantially interfere with PCR amplification of modified nucleotides. Alternatively, after selection of a suitable group of aptamers, the aptamers may be modified and then be partitioned to select for improved affinity and selectivity.

Modification may also be made to the aptamer to limit the non-specific binding of the aptamer. For example, the phosphates backbone may be modified such that a peptide nucleic acid (PNA) aptamer is formed. Given its neutral charge, a PNA should exhibit improved binding to a negative nucleotide and essentially be inert to any surface designed to bind nucleotide through interaction of the phosphate. This would have the double advantage of enhanced affinity and decreased non-specific surface binding.

Unless specifically stated, the term "nucleotide" as used herein is meant to include a nucleoside.

In order that the invention described herein may be more fully understood, the following examples are set forth. These examples are for illustrative purposes only and are not to be construed as limiting this invention in any manner.

EXAMPLES

Example 1

Selection of dAMP-specific Aptamers

The following example illustrates the selection, isolation, and characterization of oligonucleotide aptamers that specifically bind the nucleotide dAMP but not nucleotides containing the bases guanine, cytosine, or thymine. In order to provide a highly diverse initial pool of DNA sequence, from which ligand-binding aptamers can be obtained, single-stranded DNA was synthesized that contained a 42-base segment where at each position bases where incorporated with equal probability. This variable sequence was flanked by fixed-sequence segments: 5'-GGCAAGCTTGGGCCTCATGTCGAA-(N)$_{42}$-GAGCAATGGCGATGACGGATCCTCA-3' (SEQ ID NO:5).

Figure 1:
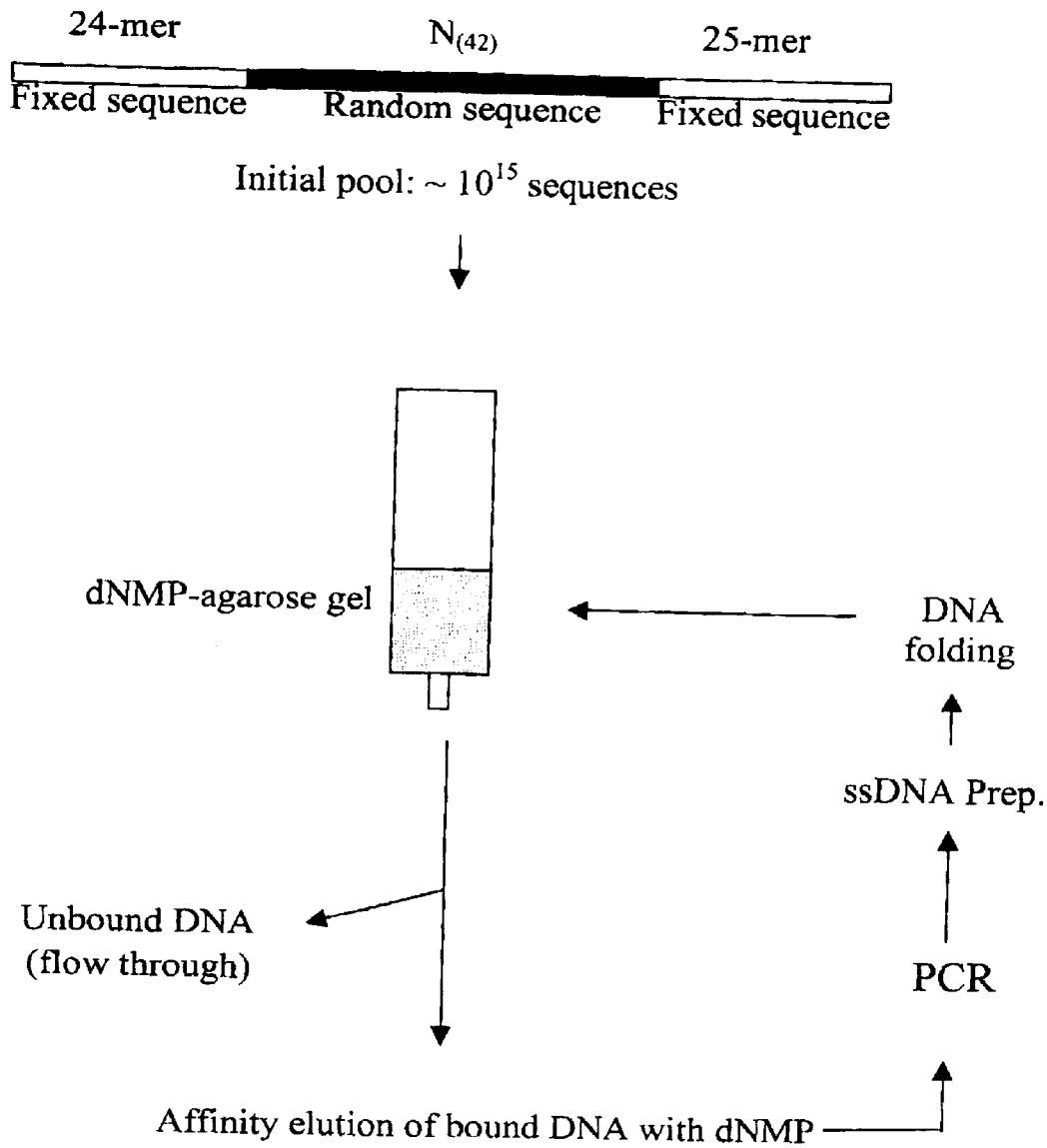
FIG. 1 depicts a schematic diagram of the process for selecting a nucleotide-binding aptamer.

The fixed-sequence segments are necessary for subsequent amplification, and are complimentary to the primers used for PCR. The 42-base random sequence can in principle yield up to $10^{25}$ unique sequences, but practical constraints on DNA synthesis yield (on order of nmoles) limits the diversity to at most $10^{15}$ sequences. Filtering of this initial pool of DNA is then obtained by the process of repeated rounds of selection for a target ligand (here dAMP) using affinity chromatography, followed by PCR amplification of specifically-eluted oligos, to yield an enriched pool of dAMP-binding DNA. This general scheme is indicated in FIG. 1.

Figure 2:
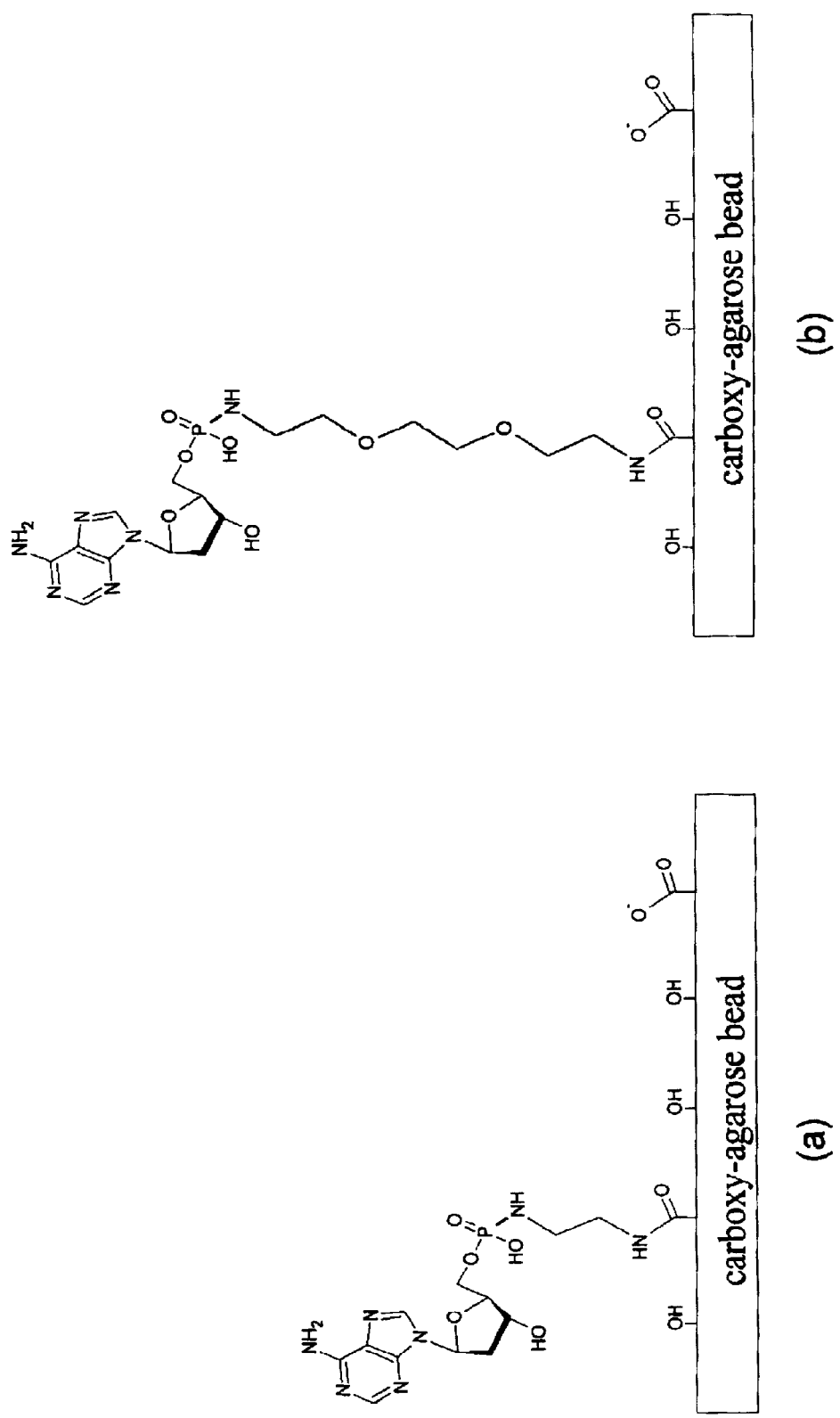
FIGS. 2a–2b is a diagram of the linkage that covalently couples dAMP to an agarose matrix through (2a) a 4-atom ethylenediamine linker, or (2b) a 10-atom triethleneglycold-iamine linker (Jeffamine).
Figure 3:
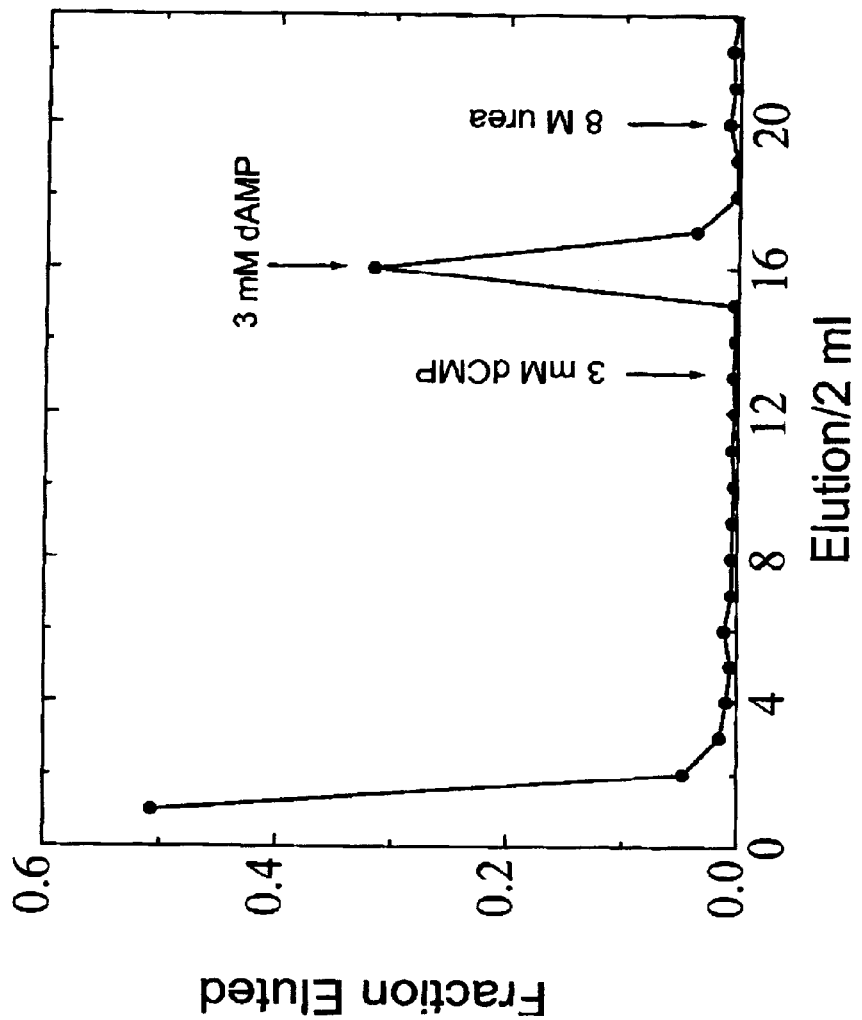
FIG. 3 depicts the elution profile of round 14 pool for aptamers that bind dAMP.

An initial pool (3 nmole) of ssDNA containing a 42-base segment of randomized sequence flanked by primers of fixed sequence, was folded (75° C. for 5 min, cooled to room temperature over 20 min.) in 100 mL of column buffer (0.3 M NaCl, 20 mM Tris, pH 7.6) and applied to an affinity column containing a 1-mL bed of dAMP-ethylenediamine-agarose (350 nmole/mL) that had been pre-equilibrated with 10 mL of column buffer. Nucleotide coupling to the agarose matrix is shown in FIG. 2(a). After a 10-minute incubation, the column was washed with 10 mL of column buffer to remove weakly-bound oligos. The bound oligos were then eluted with 4 mL of 8M Urea. The wash and elution were collected in 2 mL fractions. The fractions containing the eluted DNA were pooled, ethanol-precipitated, amplified by PCR, and purified for size on an agarose gel. Size purification was important in later rounds as increasing amounts of high-molecular weight DNA was generated by PCR (which was subsequently found to be a PCR artifact). This selection procedure was repeated up to round 6. For all rounds after the first round, the elution profile was monitored by fluorescence from a TAMRA dye that labeled the 5'-primer. At round 7, the elutant for bound DNA was changed from urea to 4 mL of 3 mM dAMP, to force specificity in the pool for the dAMP nucleotide. At round 8 and above, the selection conditions were made more stringent by washing with 4 mL of 3 mM dGMP or dCMP prior to elution, to remove the fraction of bound aptamers with undesirable cross-specificity for a guanine- or cytosine-containing nucleotide. At round 11, 5 mM MgCl$_2$ was added to the column buffer. This had a significant effect on improving the fraction of the pool that specifically bound to the affinity column. Selection continued to round 14, where the fraction of DNA eluted with dAMP was 35%. The elution profile for round 14 is shown in FIG. 3.

The selected DNA aptamer from round 14 were primer-extended to double-stranded DNA by PCR amplification, and cloned into the pCRII cloning vector. The round 14 pool was cloned and sequenced under two conditions. In the first batch, the pool was PCR-amplified and cloned without gel-purification for size. Here, 36 clones were sequenced, of which 28 contained acceptable sequence reads. In the second batch, the round 14 pool was amplified and gel-purified for size, selecting only those sequences corresponding to 91-mers. Here, 14 clones were sequenced, of which 10 contained acceptable sequence reads.

The sequences obtained from cloning are shown in FIG. 4(a). The sequence derived from the 42-base variable segment is shown in uppercase, while the fixed primer sequence is shown in lowercase. The sequences are grouped to emphasize the consensus (boldtype) sequence contained within flanking complimentary sequences (underlined). The consensus consists of a 19-base sequence CGG RGG AGG NAC GGR GGAG (SEQ ID NO:1), of which 14 bases are absolutely conserved, 2 bases very highly conserved (only clone 14 differs), two bases that are strictly purines R, and one base N that is mostly not a G. The consensus is guanine-rich (63% G) for the dAMP aptamer clones. As FIG. 4(a) shows, the batch 1 clones obtained without size selection are almost all 115-mers, although the starting aptamer was 91 bases in length. As noted above, in early rounds the PCR-amplified DNA pools, run on an agarose gel, contained only 2 bands (ss and ds DNA of one size of ~90 bases), while in later rounds additional bands appeared, and these dominated the pool in the final rounds, even though they were gel-isolated and rejected at each round. The additional bands appear to be a sequence-dependent PCR artifact that produced a ladder of bands from the 91-mer DNA. However, there is agreement in the consensus sequence for both long (115-mers) and short (91-mers) clones. Initially, clones from both size classes were examined.

Figure 5:
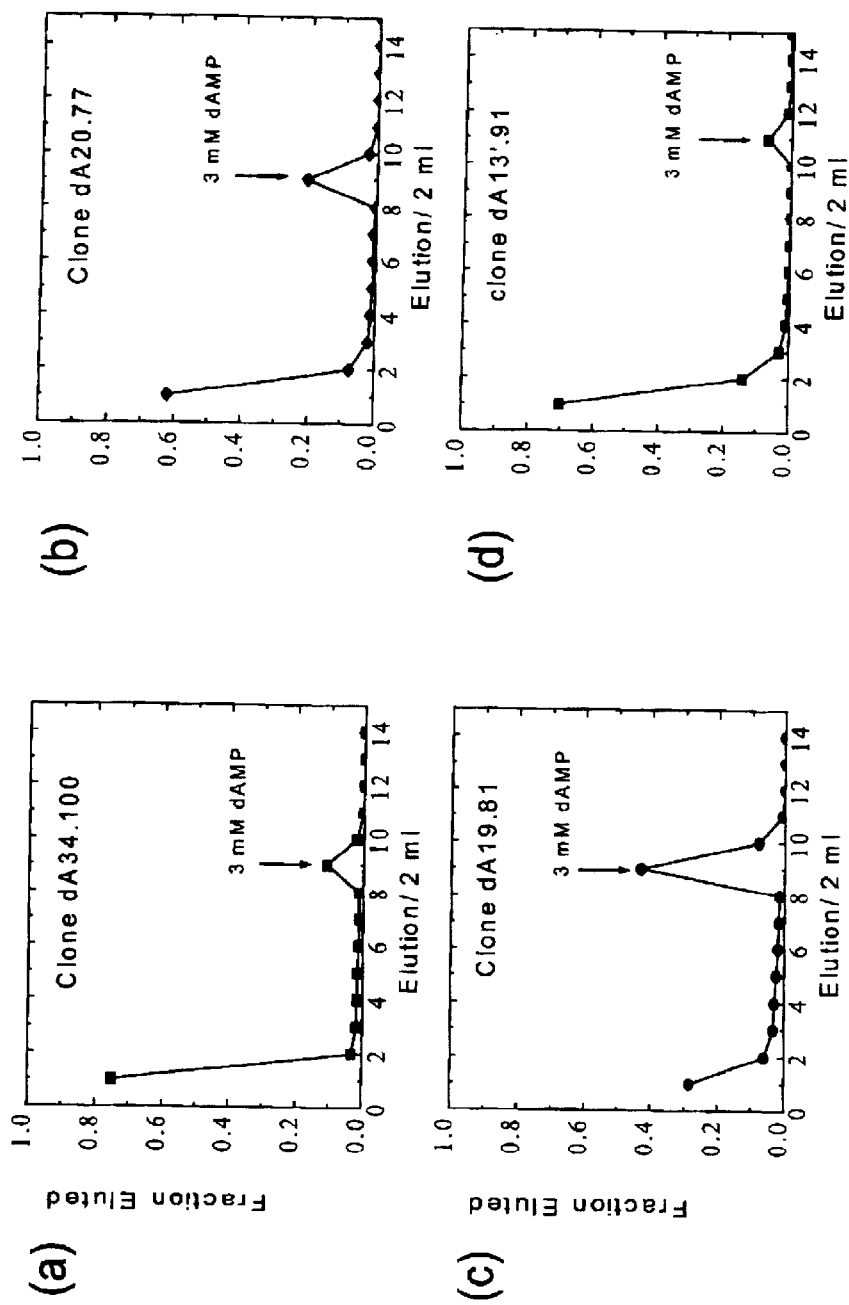

Four clones (dA19, 20, 34, 13') were synthesized for binding assays. In addition to the random sequence region, approximately 10 bases of the fixed sequence at the 5' end and all 24 bases of the fixed sequence at the 3' end were included. These sequences are shown in FIG. 4(b). The synthesized clones, each labeled with a TAMRA dye at the 5' end, were folded and tested on separate dAMP-ethylenediamine-agarose columns (350 nmole dAMP/mL of gel, 1 mL bed) to determine relative binding affinity. As shown in FIG. 5, all four clones bind to the dAMP column, and differ mainly in the fraction that passes through in the first 1–2 fractions, which for each clone is the fraction not properly folded to bind dAMP.

Figure 6:
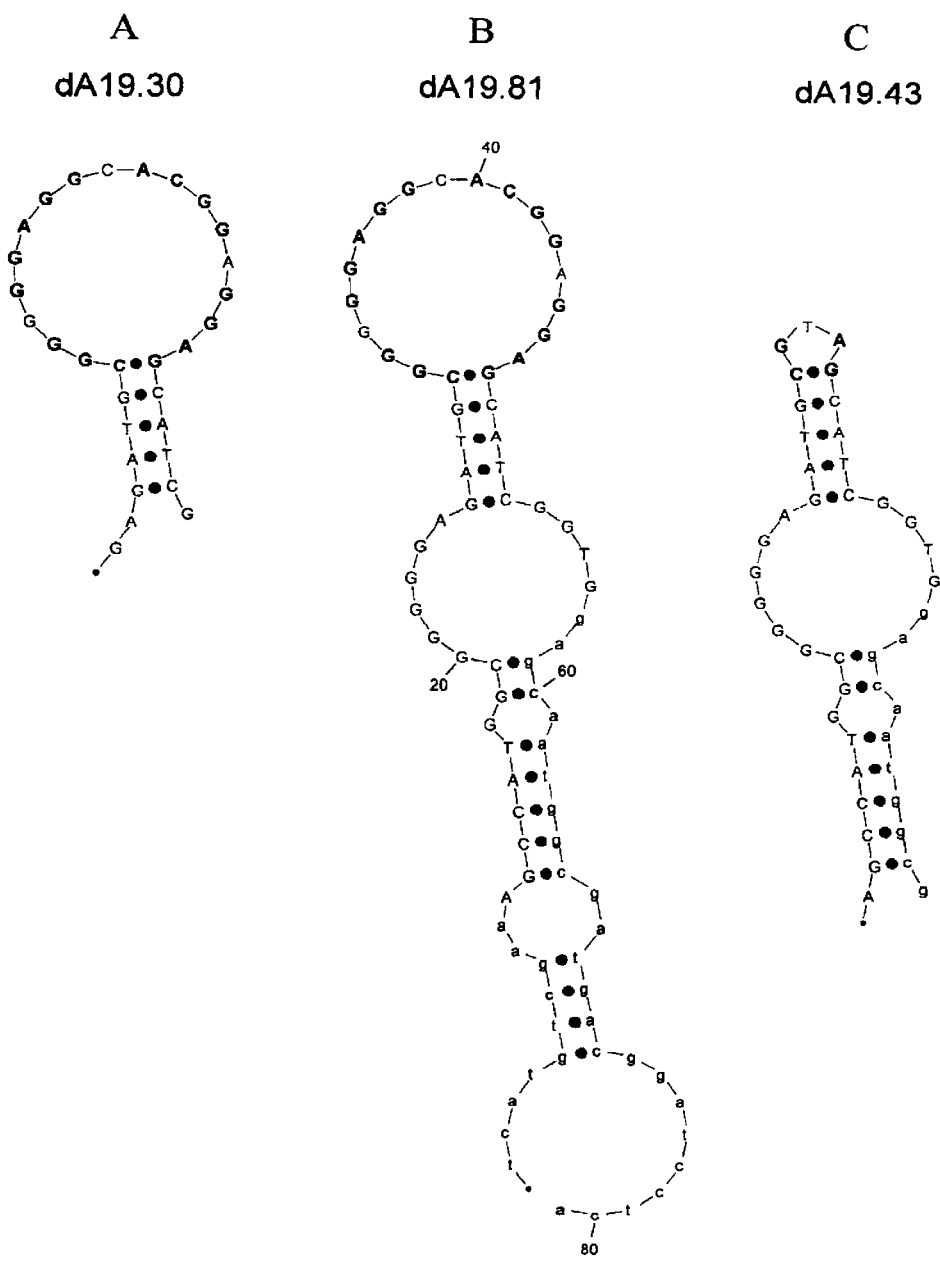

In order to show that the consensus region present in all of the clones is required for binding the dAMP ligand, clone dA19 was examined in greater detail. As shown in FIG. 6, the ssDNA oligo can be predicted to be folded to contain two loop regions held together by two stem regions (defined by Watson-Crick base-pairing). Of the two loops, only one contains the consensus (in boldfaced).

Figure 7:
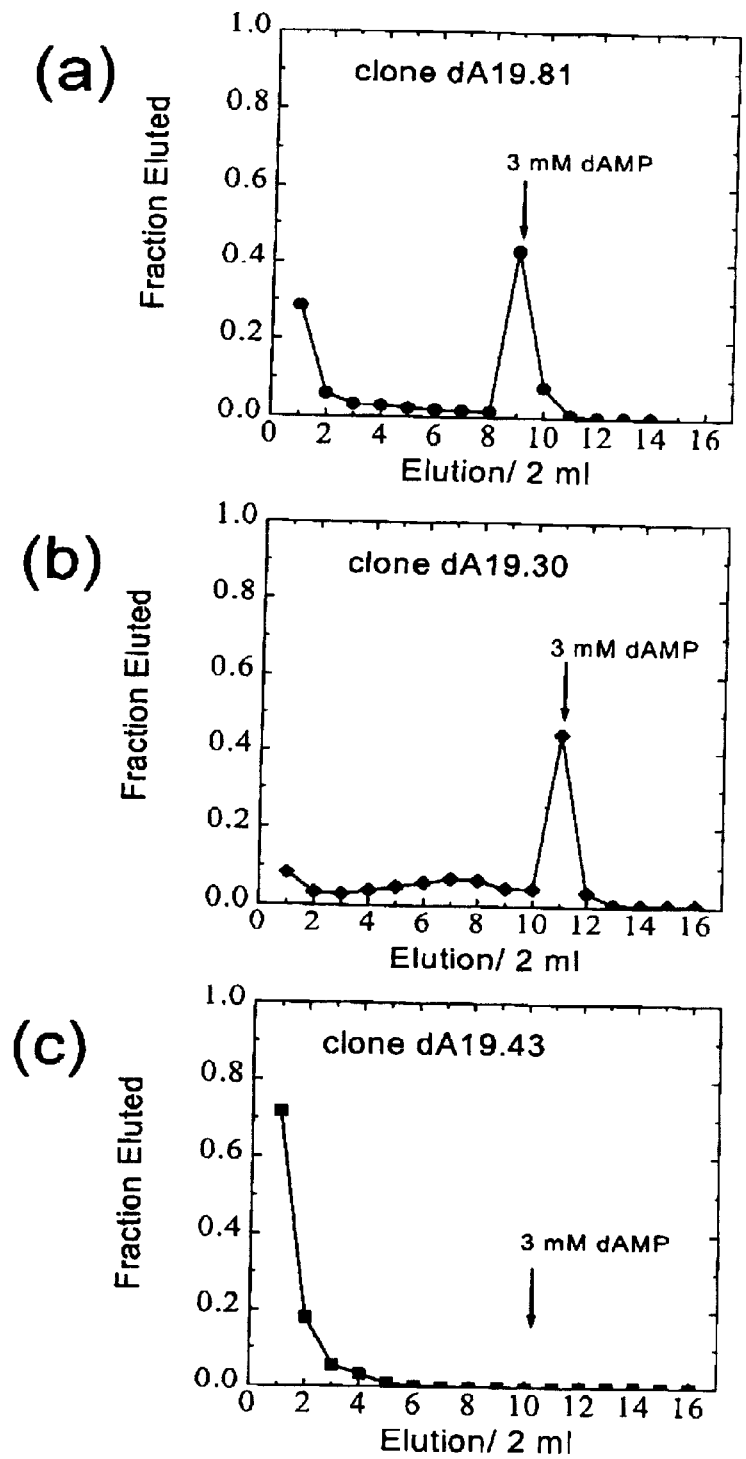

Two abridged versions of clone dA19 were synthesized, dA19.30 containing the loop with the consensus sequence and one stem, and dA19.43 containing the second loop flanked by a stem on either side but not containing the consensus region. As shown in FIG. 7, the elution profiles run on separate dAMP-ethylenediamine-agarose affinity columns for these oligos indicate that while the 30-mer dA19.30 binds almost as well as the 81-mer dA19.81, the 43-mer, which does not contain the consensus, washes of the column in the first three fractions. This test indicates that the loop containing the consensus is necessary for binding, and that much of the sequence of the 81-mer is unnecessary.

The effect of the length of the linker used to covalently bind nucleotide ligands to the agarose matrix for the affinity columns used here was tested using the shortened aptamer dA19.30. In FIG. 8, the elution profiles for this aptamer on aragose gel containing 200 nmole/mL coupled via a 4-atom ethylenediamine linker [FIG. 2(a)] or a 10-atom triethyleneglycol diamine ceffamine) linker [FIG. 2(b)] are shown. Both affinity columns exhibit the same passthrough, as expected, but the amount of aptamer which 'leaks' off the column during washing is substantially higher for the ethylenediamine linker. This suggests that the short ethylenediamine linker leads to greater inhomogeneity than the 10-atom jeffamine linker. A preferred linker like jeffamine minimizes this inhomogeneity, presumably by moving the nucleotide ligand farther from the surface of the solid support, yielding a more solution-like binding.

For any given aptamer clone, the fraction that passes through the affinity column is presumably the fraction not properly folded, and this fraction can be as high as 80%. This should be distinguished from the affinity of the correctly folded fraction. The avidity of an aptamer clone, the combination of affinity and fraction of active species, can be improved with some experimentation. For long sequences there may exist multiple structures with comparable free energy and only one of which may bind with high affinity to the nucleotide ligand. For example, the 91-base sequence of clone dA13' can form several different structures with comparable free energy, based on predicted secondary structure using the ssDNA folding program DNA Mfold [M. Zucker, http://.www.cbr.nrc.ca/zukerm/cgi-bin/form1-dna.cgi; Zucker, M., Meth. Enzy. 180, 261 (1989)]. By removing part of the primer sequence at both the 5' and the 3' ends, one finds the predicted number of structures decreases to just two.

Figure 9:
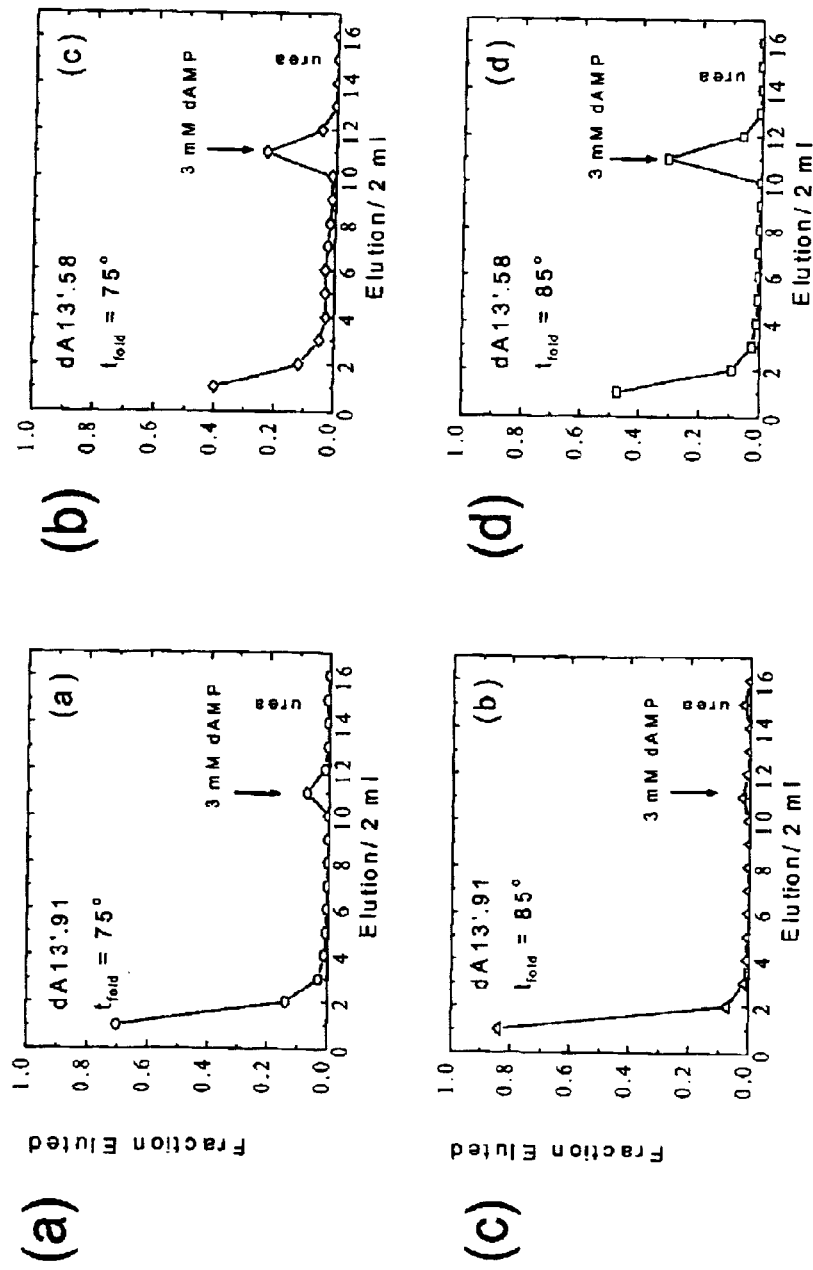

This shortened version of clone dA13' was synthesized and tested at two different folding temperatures. As shown in FIG. 9, the fraction of aptamer retained by the dAMP-jefferamine-agarose column, increases from ~15% for the full length aptamer to ~40% for the shortened 58-mer, and that the 58-mer is less sensitive to folding temperature. The structures formed by the 58-mer, shown in FIGS. 10(A) and 10(B), can be further tested by removing bases 8–13 (i.e. removing TGTCGAA), which yields a unique minimal-energy structure (based on calculation) shown in FIG. 10(C). This 51-mer was synthesized and tested on a dAMP-jeffamine-agarose affinity column. As shown in FIG. 11, about 80% of dA13'.51 is retained by the column, a 5-fold improvement over that for the original 91-mer version of this clone. Additional improvements in aptamer avidity through removal of non-essential sequence could be made but were not attempted here. (Programs such as Mfold calculate energies based on Watson-Crick and G-T wobble base-pairing; so that hairpins, base triples, pseudoknots, etc. are not included. Structure calculations like these are useful as guides, but are unlikely to reveal the actual structure of the aptamer).

Figure 12:
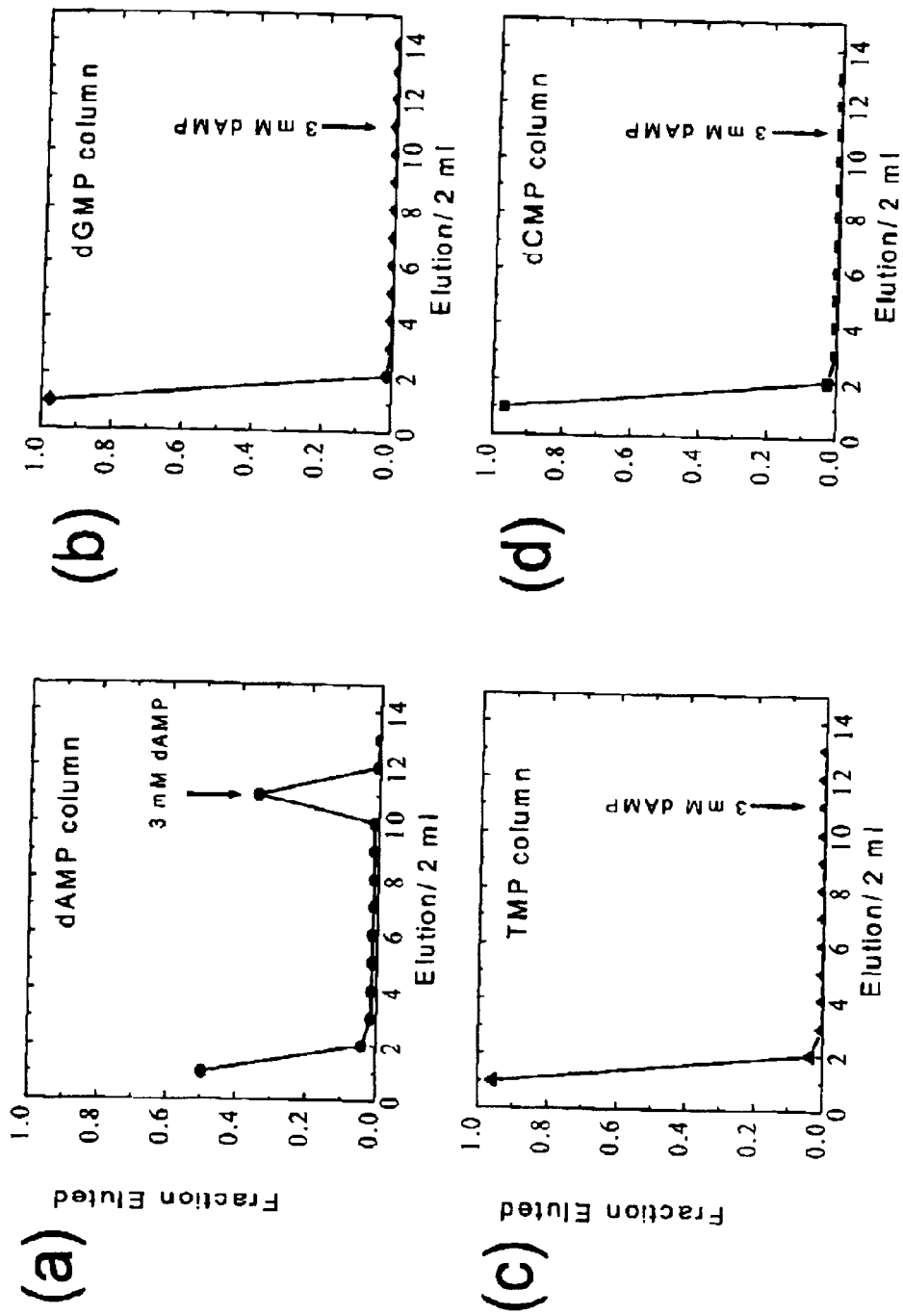

Several clones were tested for specifity using affinity columns (1-mL beds) of agarose beads with the jeffamine linker and derivatized with approximately equal concentrations (400 nM dNMP per mL of gel) of either dAMP, dGMP, dCMP, or TMP. For example, elution profiles on the four columns for the clone dA13'.58 are shown in FIG. 12. For the G, C, and T gels, greater than 95% of the aptamer passes through the columns in the first fraction of 2 mL, indicating that the $K_d$ for these nucleotides exceeds 0.1 mM. For the A gel, 50% passes in the first fraction, while 33% of the aptamer is retained after 10 fractions of washing, based on the amount eluted with 3 mM dAMP. These measurements indicate a high degree of specificity of the aptamer for the base A, but not for G, C, or T.

The ionic components of the buffer were tested to determine their effect on aptamer binding. Assays were performed using clone dA1340 .58, in which modified buffer was used for both folding and applying this aptamer to the affinity columns. The standard buffer was 0.3 M NaCl, 20 mM Tris, 5 mM MgCl2, pH 7.6. Only one component was changed in an assay. It was found that the binding affinity disappears without Mg ions in the buffer, but there is little difference in binding between 5 mM and 20 mM Mg ions. The sodium salt concentration can be dropped to 50 mM with slightly better binding affinity. There is no change in the binding affinity when the Na+ cation is replaced by Li+ (at 0.3 M). Finally, at standard buffer conditions, the binding affinity is improved 2–4 fold by lowering the temperature from 23° C. to 4° C.

The equilibrium dissociation constant, $K_d$, was determined by ultrafiltration binding titration. For these measurments, 100 µL of 1-µM dA13'.51 was incubated for 45 min with $^{32}$P-labeled dGMP at concentrations ranging from 10 nM to 50 µM. Free and bound radio-labeled nucleotide were separated by ultracentrifuge in a spin filter column, and the bound nucleotide measured. These measurements, shown in FIG. 13, show that the $K_d$ is 1.8 µM at 4° C.

Example 2

Selection of dGMP-specific Aptamers

The following example illustrates the selection, isolation, and characterization of oligonucleotide aptamers that specifically bind the nucleotide dGMP and not nucleotides dNMP, N=A, C, or T. To obtain aptamers with specific binding to dGMP, an initial pool (1.6 nmole) of ssDNA oligos containing a 42-base segment of randomized nucleotides flanked by primers of fixed sequence, was folded (heated to 85° C. for 5 min, then cooled to 4° C. at 6° C./min) in 100 µL of column buffer (0.3 M NaCl, 20 mM Tris, 5 mM MgCl2, PH 7.6) and applied to an affinity column containing a 1-mL bed of dGMP-jeffamine-agarose (500 nmole/mL) that had been pre-equilibrated with 25 mL of column buffer. The jeffamine (triethyleneglycoldiamine) linkage is shown in FIG. 2(b). After a 10-min incubation, the column was washed with 20 mL of column buffer to remove unbound DNA, followed by 6 mL of 8 M urea to elute bound DNA. The wash and elution were collected in 2 mL fractions. The amount of DNA in each fraction was measured by fluorescence detection of a TAMRA dye label, attached to the DNA on the 5' end. The fractions containing the eluted DNA were pooled, ethanol-precipitated, amplified by PCR, and purified for size on agarose gels, typically yielding 50–100 pmole of ssDNA. This selection procedure was repeated on a new column for 1 additional round.

For the 3rd round, the elution procedure was changed to enhance specificity to dGMP. After loading and incubating the amplified DNA from round 2, the column was washed with 20 mL of column buffer, then 6 mL of 3 mM dGMP in column buffer to collect bound DNA eluted by free dGMP, and then with 6 mL of 8 M urea to determine the amount of DNA bound retained by the column. The dGMP-eluted DNA was pooled, amplified, purified, folded and applied to a new column for further selection.

At round 7, pre-selection against dAMP was performed. The DNA-aptamer pool derived from round 6 was first applied to a dAMP column, and the material that passed through this column was applied to a dGMP column. For Round 9 and subsequent rounds, the selection procedure was modified to include counter-selection, so that the wash prior to elution included 2–3 fractions of 3 mM dAMP, to remove bound oligos with affinity for dAMP. At round 11, the aptamer pool was first passed through a blank column (derivatized with linker but without nucleotides), then applied to a low-density dGMP column (160 nmole of dGMP per mL of gel). A low density dGMP-column was used for all subsequent rounds. Selection continued to round 16, where the amount of DNA eluted with dGMP reached a plateau at 20%. The fraction eluted versus round is shown in FIG. 14.

The round 16 pool was cloned into the pCRII cloning vector and sequenced, and these sequences are shown in FIG. 15(a). A number of clones contained identical sequence. For clarity, FIG. 15(a) condenses the redundancy and shows the 42-base randomize segment distinguished (in uppercase) from the fixed primer sequences (lower case). Bases that are conserved in these clones (shown in boldface) are grouped to emphasize a consensus. The consensus sequence for each clone is contained within flanking sequences that differ from clone to clone but contain complimentary sequence segments (underlined). For several clones (e. g. clones 4, 14, 21, etc) complimentary sequence segments can recruit part of the primer sequence. The consensus sequence apart from point mutations, TGGGNTGGGNNTGGGNAGGGT or TGGGNTGGGNTGGGNAGGGT (SEQ ID NO:4 or SEQ ID NO:90, respectively) is 60% G-rich, whereas the variable flanking regions, on average, are only slightly so (29%).

Figure 16:
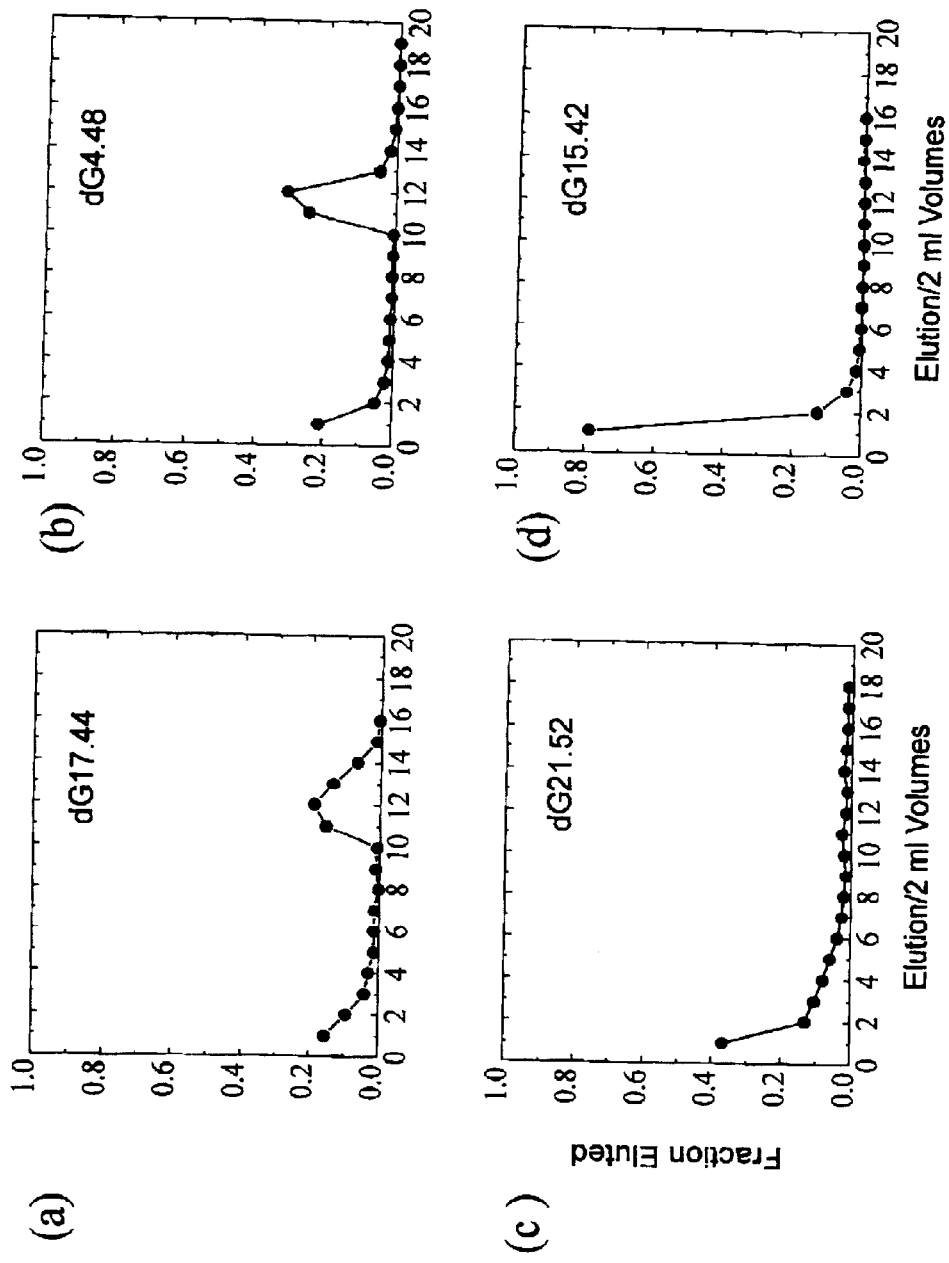

Four clones (clones 17, 4, 21, and 15) were synthesized for further tests. For practical reasons (e.g. synthesis yield), these clones were reduced in length (FIG. 15(b)) by deleting the primer sequences, unless these sequences appeared to base-pair with part of the random sequence. For example, a portion of the 3' primer sequence was included for clones 4 and 2 1, a portion likely to be necessary for folding. In addition, a TAMRA dye molecule was conjugated to these shortened clones at the 5' end. Each of these four clones, after folding, were tested on separate dGMP-jeffamine agarose columns (160 nmole dGMP/mL of gel, 1 mL bed) to determine relative binding affinity. As shown in FIG. 16, clones 17 (dG17.44) and 4 (dG4.48) bind strongly to the columns, whereas clones 21 (dG21.52) and 15 (dG15.42) have very low affinity, washing off the column in the first few fractions. It is possible that for these clones more of the primer sequence is necessary for formation of a high affinity aptamer. However, in the case of clone 15, part of the consensus region is missing, suggesting that affinity for dGMP requires the full consensus region. Clone 21, on the other hand, differs from clone 17 (a successful clone) in their consensus region by just one base. To test whether this one-base change significantly alters binding affinity, an oligo dG17.44.g (shown in FIG. 15(b)) was synthesized. This oligo bound the dGMP affinity column as well as dG17.44, so that the one base change within the consensus region was not responsible for the reduced binding of clone 21. This indicates that the sequence of the flanking region, or the order and degree of complimentary base pairing in this region, contributes to the binding affinity.

Figure 17:
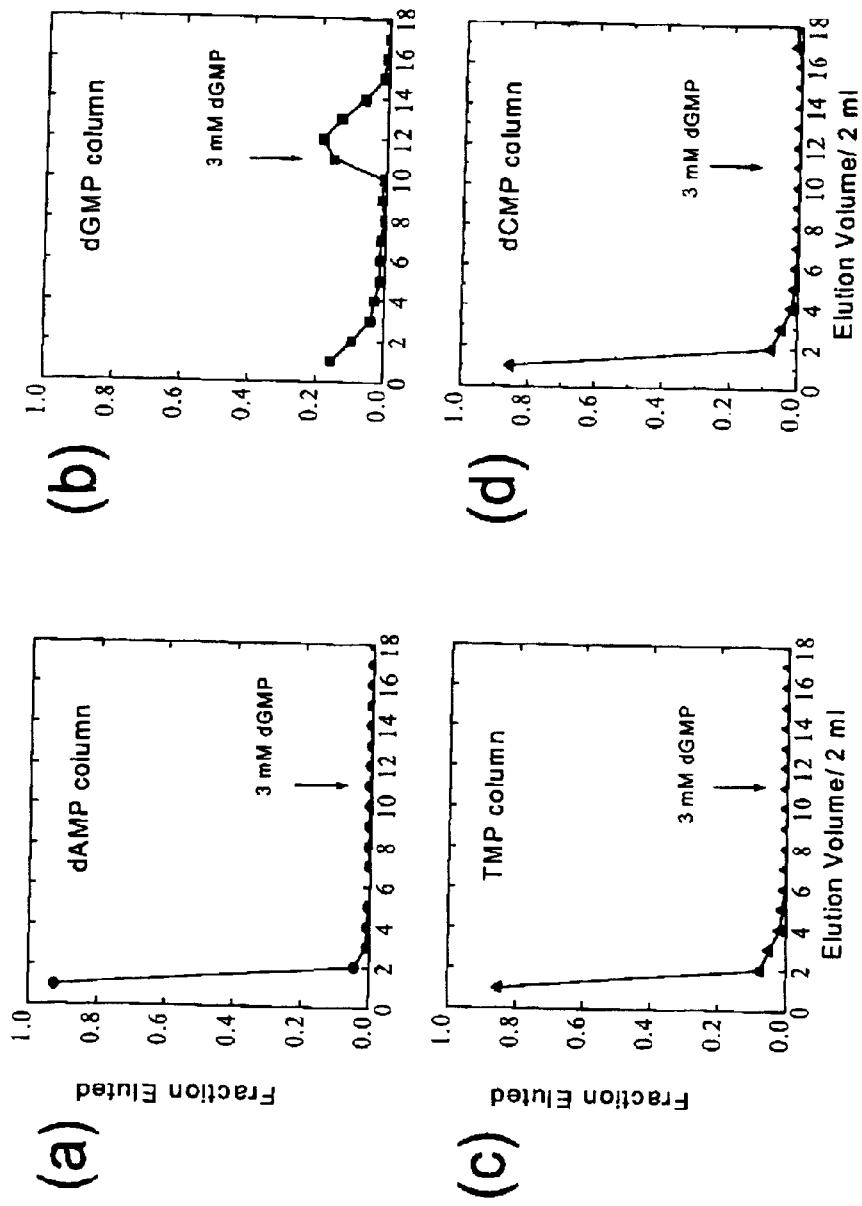

Both abridged clones dG17.44 and dG4.48 were further tested for binding nucleotides other than dGMP. Each clone was tested on affinity columns (1-mL beds) of agarose beads with the jeffamine linker and derivatized with approximately equal concentrations (400 nmole dNMP per mL of gel) of either dAMP, dGMP, dCMP, or TMP. Elution profiles on the four columns for clone 17 (dG17.44) are shown in FIG. 17. For both clones on the A, C, or T gels, greater than 90% of the aptamer passes thru the columns in the first two fractions (4 mL), and no measurable aptamer is eluted by 3 mM dGMP. For the dGMP gel, 60% is retained on the column after 10 fractions of washing, and this is recovered in elution with 3 mM dGMP. For both clones 17 and 4, the A, C, and T elution indicates that the Kd for binding these nucleotides exceeds 100 µM, estimated from the equations for isocratic elution. For comparison, an isocratic elution profile for clone 17 on a dGMP column, using only column buffer as the elutant (data not shown), indicated that the affinity of clone 17 for dGMP is less than 1 $\mu$M.

To determine what part of the dGMP nucleotide contributes to binding specificity, measurements were made of the relative affinity of clone 17 for nucleotides or nucleosides of various G-analogs containing substitutions at locations around the purine or sugar rings. The experiment involved loading dG17.44 on a dGMP column, and measuring the fraction eluted by 3 mM of G-analog, compared to that eluted by 3 mM of dGMP. As shown in FIG. 18, many of the analogs tested had 30–100% of the affinity of dGMP, while 7-methylGMP had very weak affinity, and the deoxynucleotides of A, C, or T had no measurable affinity. These results indicate that clone 17 is tolerant to some modifications of the guanine structure, but not for transformation to the other common bases.

To shed light on the aptamer structure, the effect of the salt and Mg used for the buffer was measured. The elution profile of clone 17 on a dGMP-gel in a buffer where the NaCl was replaced with either LiCl or KC was measured. The buffer was 300 mM salt (either LiCl or KCl), 20 mM Tris, 5 mM $MgCl_2$, pH 7.6. The aptamer was folded in this buffer, applied to the column pre-equilibrated in this buffer, and washed with this buffer. As shown in FIG. 19, the dG17.44 aptamer has no affinity for dGMP in either Li or K salts, indicating that both Li and K ions either disrupt or alter the aptamer structure, or otherwise interfere with ligand binding. In a separate experiment, a NaCl buffer without $MgCl_2$ was tested: 20 mM Tris, 300 mM NaCl, 1 mM EDTA, pH 7.6. The EDTA was added to chelate any residual divalent ions present. The elution profile (data not shown) was unchanged from that of the standard buffer, indicating that the Mg ion does not play a role in dGMP-aptamer binding.

The equilibrium binding constant $K_d$ was determined by isocratic elution and by analytical ultrafiltration, to yield a value for binding dGMP in solution. For the method of isocratic elution, a 2.7 mL affinity gel bed ($V_t$ is the total column volume, with area of 0.2 $cm^2$) containing 160 $\mu$M of bound dGMP, was loaded with 100 $\mu$L of 3-mM clone 17 (dG17.44) aptamer. Column buffer was applied at 0.25 mL/min, and 70 fractions (1.75 mL/fraction) were collected, at which point the remaining bound aptamer (75%) was removed with 3 mM dGMP. The measured void volume $V_o$ was. 1.4 mL, while the eluted volume $V_e$ was 122 mL. The value of $K_d$ can be estimated from $(0.5)[dGMP]_{bound}(Vt-V_o)/(V_c-V_o)$ to be less than 0.85 $\mu$M.

For ultrafiltration binding measurements, 100 $\mu$L of 1-M dGMP17.44 was incubated for 45 min with $^{32}$P-labeled dGMP at concentrations ranging from 10 nM to 10 $\mu$M. Free and bound radio-labeled nucleotide were separated by ultracentrifuge in a spin filter column, and the bound nucleotide measured. These measurements revealed that the solution $K_d$ is 350 nM at room temperature and 45 nM at 4° C. These are effective values of $K_d$. FIG. 20 shows the binding curve at 4° C., and based on a linear best fit to the data, the y-intercept is 0.65, indicating that only 65% of the aptamers in solution are active, but these have a $K_d$ of 30 nM. This fraction of active aptamers, (i.e. that are properly folded and bind dGMP) is the same as that found from the affinity column measurements (where the fraction not active wash off the column in the first few fractions).

The structure of the G aptamer is discussed below. The appearance of the triplet GGG four times in the consensus region suggests that G-quartets are involved in the structure of the aptamer. The thrombin DNA aptamer, a 15-mer containing four GG repeats, is known from both solution NMR and X-ray crystallography measurements to form a structure consisting of two tiers of G-guartets. G-quartet structures are generally known to either form intramolecular structures, intermolecular quadruplexes, or to not form in solution depending on the buffer salt. Because G-quartets involve phosphate base pairing of the N7 position of the guanine base, whereas Watson-Crick does not, protection studies were performed on the clone dG17.44, to determine if the N7 position of the guanines in the consensus region were involved in N7 bonding. It was found that all of the guanines in the consensus region were protected, while none of the guanines in the flanking regions outside of the consensus were, suggesting the dGMP-aptamer adapts a G-quartet structure for binding the dGMP ligand.

The salt dependance of the aptamer binding, noted above, lends support to a G-quartet structure for the aptamer. It is known that the Li+ cation diminishes the formation of quartet structures, while high concentrations of K+ ions enhance formation of intermolecular quaduplexes, and Na+ ions promote formation of the unimolecular g-quartet. The measured salt dependence of the dG17.44 binding to dGMP correlates with the preferential formation of a unimolecular G-quartet structure.

Example 3

Selection of CMP-specific Aptamers

Selection for a CMP-binding aptamer followed the general prescription used above, where the affinity column consisted of CMP-agarose (Sigma) containing 2.8 $\mu$mole of bound ligand per mL of gel. Here, the nucleotide was linked to the solid matrix through the sugar hydroxyls. Affinity columns of 1 mL bed volume were pre-equilibrated with 20 mL of standard column buffer, to which a nmole-quantity of randomized-sequence DNA, folded at 85° C., was applied. After incubation and washing, 3 mM CMP in solution was used to specifically elute bound DNA. PCR amplification and ssDNA preparations were performed as previously described. The selection continued for 21 additional rounds. By round 19, about 10% of the DNA eluted with solution CMP. For subsequent rounds, both pre-selection and counter-selection using AMP nucleotides was employed to improve specificity for the CMP-nucleotide. The percentage of DNA eluted by CMP versus selection round is shown in FIG. 21. The elution profile for round 22 is shown in FIG. 22.

The fraction of CMP-eluted DNA from round 22 was amplified by symmetric PCR, and gel-purified dsDNA was cloned into the pCRII cloning vector and subsequently sequenced. Thirty-five out of thirty-eight clones yielded acceptable. sequence, shown in FIG. 23(a). The sequences are arranged to organize the variable-sequence segments (upper case), fixed primer sequence (lower case), and consensus (boldface). The redundancy in sequence for identical clones is suppressed, with the number of clones with identical sequence indicated. The clones appear to break into two groups, with the first exhibiting a more complex consensus given by GGGAGGGTNNNGGNG (SEQ ID NO:2), wherein N is any base and the last N is often a pyrimidine base. The less dominant consensus is GGTNNNGGNG (SEQ ID NO:3).

Two clones were selected for further tests. Abridged sequences of clones 3 and 9, shown in FIG. 23(b), were synthesized and tested for affinity. The choice of sequence reduction was guided by secondary structure calculations using the program DNAMfold. As in previous examples, the 5' end of the shortened aptamers were labeled with a TAMRA dye. Using standard column buffer, clone 9 (C9.58) was folded, and applied to separate affinity columns of either CMP or AMP (each with approximately 2 μmole of bound ligand per mL of gel, and each employing the same linker). As shown in FIG. 24, only the CMP column yields binding of aptamers that specifically elutes with CMP. Both columns retain the same small fraction of aptamers that are removed with urea and are non-specifically bound to the matrix. From the elution profile of clone 9 on the CMP column it is clear that the fraction of aptamers properly folded is high (>90%), while the affinity, estimated from the isocratic elution behavior of the aptamer during washing, is about 35 μM. Clone 3 yielded similar results, as shown in FIG. 25, of high yield of properly-folded aptamers and a binding constant $K_d$ of about 50 μM. When clone 3 is folded in column buffer containing KCl in place of NaCl, and applied to a CMP column in this modified buffer, no binding is measured to the CMP nucleotide, although some non-specific binding is still present. The CMP-aptamers isolated here could be further improved by using known methods of mutagenic PCR to obtain a low-diversity pool. This would provide a starting pool for re-selection for a CMP aptamer with better affinity, using more stringent selection conditions such as lower concentration of nucleotide ligand on the affinity column. Such a pool could also provide an initial pool for the selection and isolation of aptamers that bind dCMP.

Example 4

Fabrication of Functionalized Surfaces for Coupling Nucleotides

This example describes the fabrication of surfaces suitable for coupling nucleotides and that have very low non-specific binding of aptamers. The substrate material is chosen to be optically-transparent silica, so that for single-nucleotide detection, the excitation and emission light paths need not employ the same optics, and excitation of fluorescence by total-internal reflection (TIR) can be used. Silica is a very clean material and generally free of contaminants, while its surface can also be made clean using standard glass-cleaning methods. Cleanliness means that the surface and substrate exhibit no significant auto-fluorescence when illuminated by visible or infrared light. Hence the substrate and surface do not contribute to false-positive detection of the desired fluorescent signal from dye-labeled aptamers. Alternatively, oxide-coated silicon can be used in an epi-illumination geometry for exciting and detecting fluorescence from surface-bound detection reagents. Silicon is at least as clean as silica, and the surface chemistry reactions involving silanol groups are the same. Silicon normally has a native oxide layer about 1.5 nm thick. This thickness should be increased, by oxidation for example, to more that 10 nm, since the silicon substrate (the subsurface atomic silicon) quenches fluorescence of fluorophores within about 5 nm of the uppermost layer of atomic silicon. Such thick oxide silicon is available commercially. For the case where an aptamer detection reagent is labeled with a sufficiently bright fluorophore or group of fluorophores, glass or plastic substrates can be used. Both of these materials exhibit some autofluorescence and fluorescence from contaminants, but this will not contribute to a false positive when very bright fluorophores are used as labels. Surface chemistry for glass is the same as silica, while plastic can be plasma-etched and cleaned and converted to a hydrophilic surface for silica-like surface chemistry.

While surface treatments are known for introducing a functional group to the surface of silica, almost all methods lead to some degree of non-specific binding of reagents that are not intended to be retained by the surface.

One-millimeter thick silica substrates (from either ESCO Products or CVI, Inc) were first cleaned using the base/acid wash procedure known as SC1 and SC2. The surfaces were immersed in a solution of 5 parts $H_2O$, part $H_2O_2$, 1 part $NH_3OH$, for 10 minutes at 80° C., rinsed with high-purity DI water (18 Mohm), then immersed in a solution of 5 parts $H_2O$, 1 part $H_2O_2$, 1 part HCl for 10 minutes at 80° C., and finally rinsed extensively with high-purity DI water.

In order to accomplish silanization and activation, the following procedure, modified from that of Potyrailo et al (Anal. Chem. 70, 3419 [1998]), was used to first make a diol-silica surface, and then to activate some fraction of the hydroxyl groups with carbonyldiimidazole (CDI) for subsequent coupling of a diamine linker. Clean silica substrates were silanized by immersion in an aqueous solution of 10% Glycidoxypropyltrimethoxysilane (GOPS, United Chemical Technologies) at pH 3.5 using HCl overnight at room temperature, then heated at 90° C. for 4 hrs. After cooling back to room temperature, surfaces were briefly rinsed by dipping in clean water (10–14 times), dried with $N_2$ gas, and baked at 120° C. for 1 hr. These diol-coated substrates (as shown in FIG. 26) are then activated with CDI by reaction in a solution of dry dioxane containing 3 mM CDI for 4 hours, then rinsed with clean dioxane, and stored under vacuum in a dessicator. The treated substrates could be stored for at least several days in the dessicator without significant loss of activation.

For linker coupling, the CDI-activated surfaces were immersed in a solution of 3.4 mM triethyleneglycoldiamine (Jeffamine or ERD-148, Huntsman Corp.) in dry dioxane overnight, then washed first with clean dioxane, then water. Surfaces were then stored in column buffer (0.3 M NaCl, 20 mM Tris, 5 mM MgCl2, pH 7.6) for at least 1 day, to passivate the surface by hydrolyzing any active CDI-sites. This surface is then ready for use in nucleotide coupling. This procedure results in about $1000/(\text{micron})^2$ jeffamine linkers coupled to the surface and with one free amine group. Higher and lower surface concentrations of surface-coupled jeffamine can be achieved by varying the reaction solution concentrations of CDI or jeffamine.

Nucleotide coupling to the surface-bound jeffamine linker was obtained using aqueous solutions of 50 mM 1-ethyl-3-(3-dimethylaminopropyl)carbodiimide (EDC, Pierce Chemical), 50 mM 1-methylimidazole, 100 mM MES buffer, 10 mM dNMP, pH 6.0 for 2 hours at room temperature. Surfaces were then washed with H20, and stored in column buffer.

To determine the binding characteristics of aptamers to nucleotides linked to silica substrates, the dGMP-aptamer clone dG17.44, labeled with a single tetramethylrhodamine dye, was folded and then diluted to various concentrations, and each of these applied to a surface containing dGMP linked to the surface via a jeffamine linker. The surfaces were illuminated with 515-nm laser light in a total-internal-reflection (TIR) geometry, and the fluorescence monitored with a CCD camera. This arrangement allowed measurement of both time dependent binding (i.e. to yield the on-rate and off-rate) and equilibrium binding. FIG. 27 shows a plot of the equilibrium data, and the hyperbolic curve expected for a $K_d$ of 260 nM. From time-dependent measurements, the association rate constant and dissociation rate were $1.5 \times 10^4$ $M^{-1}$ $\sec^{-1}$ and 0.006 $\sec^{-1}$, respectively. These values yield a $K_d$ value of 400 nM. These surface measurements, made at room temperature, agree within 50% of the solution binding measurements described in Example 2.

Example 5

Base Specific Detection of Single Nucleotides Using Aptamer Affinity Probes

In order to demonstrate base-specific detection of single nucleotides, nucleotides (either dGMP or dCMP) were first coupled to the jeffamine linker using an EDC/Methylimidazole reaction, purified by HPLC, and then applied to the CDI-activated surfaces described above in Example 4, from an aqueous solution of 50 mM phosphate buffer, pH 8.3. Concentrations and time were chosen to load about 0.1 nucleotide/micron$^2$, a surface coverage that allows individual nucleotides to be resolved optically. After incubation, the surfaces were washed and soaked in column buffer for two hours, then incubated in a solution of 1 micromolar dG17.44 aptamer labeled with a single Cy5 dye in column buffer (CB) containing 0.1% Tween-20 for 15 minutes. These surfaces were then washed with 10 ml CB plus 0.1% tween-20 for 10 sec from a squirt bottle, dried and measured in a microscope set up for single molecule detection. Surfaces were imaged using a 100×, 0.9 NA dry objective onto a $LN_2$-cooled CCD camera (Princeton Instruments). Surfaces were illuminated with 7 mW of 633-nm laser light, focused onto the surface in TIR in a spot approximately 30 microns in diameter. A bandpass filter, centered at 670 nm and of width 40 nm, was used after the microscope objective, to pass fluorescence but block laser light. The CCD camera acquires an image of the surface in 2 seconds, a time sufficient to provide a S/N>20 for detection of individual Cy5-labeled aptamers, which appear as isolated bright dots on the image.

As shown in FIG. 28, based on the number of single aptamers detected, non-specific binding of dG17.44 aptamers on surfaces containing dCMP is very small (approximately 0.003 aptamer/micron$^2$). The surface containing dGMP retains a much larger number of aptamers, close to the expected number of dGMP molecules on the surface. (The exact number of surface-bound dGMP cannot be measured directly. The amount is estimated by extrapolation from measurements made at higher loading concentrations.)

Based on these measurements, the specificity of the dG17.44 aptamer for dGMP is at least 100×greater than the specificity for dCMP, in agreement with the specificity measurements made on affinity columns as described in Example 2. In addition, the functionalized silica surfaces used here have very low non-specific binding.

Example 6

Methods and Materials of Fabricating Affinity Matrix

Adenosine-monophosphate was covalently coupled to beaded agarose via ethylenediamine using carbodiimide chemistry, resulting in the linkage shown in FIG. 2(a). The agarose gel (CM Bio-Gel A, BIORAD) was carboxylate-modified, with 20 μmole COOH groups per mL of gel. The gel was first column-washed with 4 column volumes of high-purity water, adjusted to pH 5, then resuspended in $H_2O$ at 50% V/V. To couple ethylenediamine to the COOH-agarose via EDAC (Sigma), a 45 mL aqueous solution of 0.23 M EDAC and 5 mM ethylenediamine (Sigma) was made and adjusted to pH 5 with 1M HCl. Next, 45 mL of gel was poured into two polypropylene tubes and rotated end-over-end for 1 hr. (HCl was added at ½ hour to maintain pH at 5). The gel was drained and rinsed with $H_2O$ (20×column volumes) and then resuspend in $H_2O$ at 50% V/V. To couple the nucleotide to the amine-derivatized gel, a 45 mL aqueous solution of 0.23 M EDAC, 0.17 M 1-methylimidazole, and 20 mM dAMP, at pH 6.2 was added to 45 mL of diamine-reacted gel, adjusted to pH 6.2, and rotated end-over-end for 2 hrs. In order to terminate excess free amines on the gel, succinic acid was used to cap terminal amines with carboxylates. A 5 mL solution of 0.46 M EDAC and 150 mM succinic acid, adjusted to pH 6, was added to 45 mL of nucleotide-modified gel and rotated end-over-end for 2 hrs. Then, it was drained and rinsed in a column with $H_2O$ (2 column volumes) and then with Buffer A (40 column volumes). Buffer A is 0.3 M NaCl, 20 mM Tris, pH 7.6. The derivative gel was then resuspended in Buffer A at 50% v/v and store at 4° C.

dNMP-Jeffamine-Agarose affinity matrix.: Nucleoside-monophosphates were covalently coupled to agarose beads via the triethyleneglycoldiamine linker Jeffamine (XTJ-504, Huntsman) using carbodiimide chemistry, resulting in the linkage shown in FIG. 2(b). Typically, 50 ml of carboxy-modified agarose gel (Biorad) was washed with 500 mL of high purity deionized water and resuspended at 50% V/V in a reaction mixture of 0.1 M EDC (Pierce), 20 mM of Jeffamine, and 0.1 M MES buffer at pH 5.2 for 90 min. under gentle mixing conditions. This slurry was column-washed with 500 mL of high-purity deionized water, and resuspended in reaction mixture B. This mixture consisted of first reacting 0.2 M EDC, 0.2 M Methylimidazole (Sigma), and 40 mM dNMP at pH 6.2 for 30 min, then adding the diamine-reacted gel at 50% V/V overnight (about 14 hr) with gentle mixing. This slurry was column-washed with 2.5 Liters of 0.3 M NaCl, 20 MM Tris, pH 7.6 buffer, and resuspended in this buffer at 50% V/V. The quantity of nucleotide coupled to the agarose gel was measured by uv absorption after melting the reacted nucleotide-agarose gel using perchloric acid. Typically, 0.25 mL of perchloric acid was added to 0.25 mL of 50% V/V gel, placed in a 37° C. heat bath for 30 sec until the agarose beads melted, then diluted to 2 mL with high-purity water. After subtracting the absorption of gel reacted without a nucleotide, and using acid-pH extinction coefficients, [dNMP] concentrations for the reacted gel at 50% V/V were typically 180 mM, or 360 nmoles of nucleotide coupled per ml of gel. Storage at 4° C. resulted in no apparent degradation over periods of greater than 1 month.

Example 7

Molecular Biology Methods

DNA Pools: The pool of random-sequence DNA used for the initial selections was prepared by commercial synthesis of the 91-mer oligo 5'-GGC AAG CTT GGG CCT CAT GTC GAA (N)$_{42}$ GAG CAA TGG CGA TGA CGG ATC CTC A-3' (SEQ ID NO:5), where N is any one of the four nucleotides occurring with an equal probability.

Folding Procedure: Prior to use in a selection, the initial pool or amplified ssDNA were folded at either 75° C. (for dAMP selection) or 85° C. (for G or C selections) for 5 min, then cooled to 4° C. at 6° C./min.

Affinity Columns: Nucleotide-agarose columns (Area= 0.77 cm$^2$) Of 1 mL bed volume were pre-equilibrated with approximately 25 mL of column buffer (300 mM NaCl, 5 mM MgCl2, 20 mM Tris, pH 7.6). For each round of selection a fresh column and gel was used. Eluted fractions containing the DNA of interest were pooled, ethanol precipitated (1 μg tRNA or glycogen was added to facilitate the precipitation), and amplified by PCR.

PCR. The PCR reactions contained 200 μM of each dNTP, 10 mM Tris-HCl, pH 8.4, 50 mM KCl, 2.5 mM MgCl2, and 2.5 units of Taq polymerase per 100 μL reaction. The primer concentrations were 1 μM HPLC purified oligonucleotide. The 5' primer was 5'-LGG CAA GCT TGG GCC TCA TGT CGA A-3' (SEQ ID NO:86), where L=Amino linker+ TAMRA dye. The 3'-primer was 5'-TGA GGA TCC GTC ATC GCC ATT GCT C-3' (SEQ ID NO:87). Thermal cycling was 94° C. for 45 sec, 55° C. for 30 sec, and 72° C. for 60 sec (30–35 cycles) for both Symmetric PCR and Asymmetric PCR. However, preheating time for symmetric PCR was 5 minutes while for asymmetric PCR was 2 minutes. For symmetric PCR, 1 μM for both primers were used. For asymmetric PCR, 6 μM 5'-primer and 0.2 μM 3'-primer were used. All of PCR amplified DNA mix were loaded onto 4% NuSieve GTG agarose gel (FMC) for TAMRA-labeled single-stranded aptamer purification. This was also important for isolating the bands of the right length.

Cloning: The single-stranded DNA aptamer pool recovered from the last round of selection was amplified by PCR to give a single identifiable double-stranded DNA band. The primers to the ends of the aptamer were 5'-GGC AAG CTT GGG CCT CAT GTC GAA-3' (SEQ ID NO:88), and 5'-TGA GGA TCC GTC ATC GCC ATT GCT C-3' (SEQ ID NO:89). The cycling steps were as follows: 1. 94° C. for 3 minutes, 2. 94° C. for 0.5 minutes, 3. 60° C. for 0.5 minutes, 4. 72° C. for 0.5 minutes, repeat steps 1–4 30 times, then 5. 72° for 5 minutes, then 4° C. for storage. The annealing temperature and the 5 minutes at 72° C. were empirically found to be necessary for obtaining the correct sized PCR product with a single 3' A overhang suitable for subsequent cloning. The double-stranded DNAs were gel purified and isolated using the QIAEX II Agarose Gel extraction Kit (Qiagen). Purified DNA was ligated directly into PCR2.1 vector (Invitrogen) and transformed into the *E. coli* SURE strain (Invitrogen) to minimize rearrangements. Individual aptamer clones were then isolated for sequencing.

Binding Assays. Nucleotide-jeffamine-agarose columns (Area=0.77 cm2) of 1 mL bed volume were pre-equilibrated with approximately 25 mL of column buffer (unless noted, this was 300 mM NaCl, 5 mM MgCl2, 20 mM Tris, pH 7.6). Solutions of aptamers were folded in the same buffer and then applied to the column for 10 minutes, after which the column was washed for 10–100 mL of buffer.

Dissociation Constants. $K_d$ by Equilibrium Ultrafiltration The interaction of aptamers and dNMPs was measured by ultrafiltration using the method of Menguy et al. (Anal.Biochem. 264, 141–148 (1998)). In brief, TAMRA-labeled aptamer was incubated in the presence of a32P-dNMP under the specified binding conditions in a total volume of 100 μl. The reactions were placed in MicroCon 10 spin filters (Millipore) and centrifuged at 11,800×g for 8 minutes. The filtrate and retentate were collected. Aptamer concentration was determined by comparing the TAMRA fluorescence against the fluorescence of samples of known aptamer concentration. The concentration of nucleotide was determined by liquid scintillation counting. Control experiments indicate the dNMP passes freely through these filters and greater than 90% of a 58-mer aptamer is retained.

Throughout the specification and claims, the word "comprise," or variations such as "comprises" or "comprising," will be understood to imply the inclusion of a stated integer or group of integers but not the exclusion of any other integer or group of integers.

U.S. Provisional application No. 60/135,863 and other United States applications cited herein are hereby incorporated by reference.

While hereinbefore a number of embodiments of this invention have been presented, it is apparent that the basic construction can be altered to provide other embodiments which can utilize the methods of this invention. Therefore, it will be appreciated that the scope of this invention is to be defined by the claims and specification rather than the specific embodiments which are exemplified here.

We claim:

1. A method for sequencing a DNA or RNA molecule comprising the steps of separating a terminal monomer from the DNA or RNA molecule, contacting the separated terminal monomer with an aptamer that is 120 nucleotides or less and comprises a sequence selected from the group consisting of:

(a) 5'-CGGRGGAGGNACGGRGGAG-3' (SEQ ID NO:1), wherein R is G or A and N is T, C, A or G;

(b) 5'-GGGAGGGTN$_1$N$_2$N$_3$GGN$_4$G-3' (SEQ ID NO:2), wherein N$_1$, N$_2$, N$_3$, and N$_4$ is any monomer selected from the group consisting of A, C, G and T;

(c) 5'-GGT N$_1$N$_2$N$_3$GGN$_4$G-3' (SEQ ID NO:3), wherein N$_1$, N$_2$, N$_3$, and N$_4$ is any monomer selected from the group consisting of A, C, G and T; and (d) 5'-TGGGN$_1$TGGGN$_2$N$_3$TGGGN$_4$AGGGT-3' (SEQ ID NO:4), wherein N$_1$, N$_2$, and N$_4$ is any monomer selected from the group consisting of A, C, G and T and N$_3$ is no monomer or any monomer selected from the group consisting of A, C, G and T; and determining whether the aptamer of subsections (a) to (d) bound to the terminal monomer.

2. A method for detecting an AMP, dAMP, CMP, dCMP, GMP or dGMP comprising the steps of (1) contacting a nucleotide or nucleoside with an aptamer and (2) determining whether the aptamer bound to the nucleoside or nucleotide, wherein the aptamer is 120 nucleotides or less and comprises the sequence of:

(a) SEQ ID NO:1 when the nucleotide or nucleoside to be detected is AMP or dAMP, wherein R is G or A and N is T, C, A or G;

(b) SEQ ID NO:2 when the nucleotide or nucleoside to be detected is CMP or dCMP, wherein N$_1$, N$_2$, N$_3$, and N$_4$ is any monomer selected from the group consisting of A, C, G;

(c) SEQ ID NO:3 when the nucleotide or nucleoside to be detected is CMT or dCMP, wherein N$_1$, N$_2$, N$_3$, and N₄ is any monomer selected from the group consisting of A, C, G and T; or (d) SEQ ID NO:4 when the nucleotide or nucleoside to be detected is GMP or dGMP, wherein N₁, N₂, and N₄ is any monomer selected from the group consisting of A, C, G and T and N₃ is no monomer or any monomer selected from the group consisting of A, C, G and T.

3. A method for sequencing a DNA or RNA molecule comprising the steps of separating a terminal monomer from the DNA or RNA molecule, contacting the separated terminal monomer with an aptamer that is 120 nucleotide or less comprising a sequence selected from the group consisting of SEQ ID NO: 17, SEQ ID NO:40, SEQ ID NO:41, SEQ ID NO:43, SEQ D NO: 45; SEQ ID NO:48; SEQ ID NO:50, SEQ ID NO:51, SEQ ID NO:52, SEQ ID NO:53, SEQ ID NO:58, SEQ ID NO:65, SEQ ID NO:68, and SEQ ID NO:69 and determining whether the aptamer bound to the terminal monomer.

4. A method for detecting a monomer selected from the group consisting of an AMP, dAMP, CMP, dCMP, GMP and dGMP comprising the steps of (1) contacting a nucleotide or nucleoside with an aptamer and (2) determining whether the aptamer bound to the nucleoside or nucleotide, wherein the aptamer is 120 nucleotides or less and comprises the sequence of (a) SEQ ID NO: 17, when the monomer to be detected is AMP or dAMP; (b) SEQ ID NO:40, SEQ ID NO:41, SEQ ID NO:43, SEQ ID NO: 45; SEQ ID NO:48; SEQ ID NO:50, SEQ ID NO:51, SEQ ID NO:52, SEQ ID NO:53 or SEQ ID NO:58, when the monomer to be detected is GMP or dGMP; or (c) SEQ ID N:65, SEQ ID NO:68 or SEQ ID NO:69, when the monomer to be detected is CMP or dCMP.

5. The method according to claim 1, wherein N₄ of SEQ ID NO:2 is T or C.

6. The method according to claim 1 or claim 2, wherein the aptamer comprises the sequence selected from the group consisting of SEQ ID NO:6, SEQ ID NO:7; SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO:35, SEQ ID NO:36, SEQ ID NO:37, SEQ ID NO:38, SEQ ID NO:39, SEQ ID NO:42, SEQ ID NO:44, SEQ ID NO:46, SEQ ID NO:47, SEQ ID NO:49, SEQ ID NO:54, SEQ ID NO:55, SEQ ID NO:56, SEQ ID NO:57, SEQ ID NO:59, SEQ ID NO:60; SEQ ID NO:61, SEQ ID NO:62, SEQ ID NO:63, SEQ ID NO:64, SEQ ID NO:66, SEQ ID NO:67, SEQ ID NO:70, SEQ ID NO:71, SEQ ID NO:72; SEQ ID NO:73, SEQ ID NO:74, SEQ ID NO:75 and SEQ ID NO:76.

7. The method according to claim 1 or claim 2, wherein the upstream sequence of SEQ ID NO:1 is a 5' flanking region comprising the sequence 5'-CCTACT-3' and the downstream sequence of SEQ ID NO:1 is a 3' flanking region comprising the sequence 5'-AGTAGG-3'.

8. The method according to claim 1 or claim 2, wherein the upstream sequence of SEQ ID NO:1 is a 5' flanking region comprising the sequence 5'-AGATG-3' and the downstream sequence of SEQ ID NO:1 is a 3' flanking region comprising the sequence 5'-CATCG-3'.

9. The method according to claim 1 or claim 2, wherein the upstream DNA sequence of SEQ ID NO:1 is a 5' flanking region comprising the sequence 5'-GCCTCATGTCGAACCTACTGGA-3' (SEQ ID NO:77) and the downstream DNA sequence of SEQ ID NO:1 is a 3' flanking region comprising the sequence 5'-GGAAGTAGGTGAGGGAG-3' (SEQ ID NO:78).

10. The method according to claim 1, or claim 2, wherein the upstream sequence of SEQ ID NO:2 is a 5' flanking region comprising the sequence 5'-TCATGTCGAAGGGGCGTATGGGCTTTG-3' (SEQ ID NO:79) and the downstream sequence of SEQ ID NO:2 is a 3' flanking region comprising the sequence 5'-ACATGT-3'.

11. The method according to claim 1 or claim 2, wherein the upstream sequence of SEQ ID NO:2 is a 5' flanking region comprising the DNA sequence TGATCCGCGGCAGTGC-3' (SEQ ID NO:80) and the downstream sequence of SEQ ID NO:3 is a 3' flanking, region comprising the sequence 5'-TGCTTGGAGCAATGGCGATGACGGATC-3' (SEQ ID NO:81).

12. The method according to claim 1 or claim 2, wherein the upstream DNA sequence of SEQ ID NO:4 is a 5' flanking region comprising the sequence 5'-AGTGACACCAC-3' (SEQ ID NO:82) and the downstream sequence of SEQ ID NO:4 is a 3' flanking region comprising the sequence 5'-TGTGGAATCAC-3' (SEQ ID NO:83).

13. The method according to claim 1 or claim 2, wherein the upstream sequence of SEQ ID NO:4 is a 5' flanking region comprising the sequence 5'-AGATCGCCATAAG-3' (SEQ ID NO:84) and the downstream sequence of SEQ ID NO:4 is a 3' flanking region comprising the sequence 5'-GGAGCAATGGCGAT-3' (SEQ ID NO:85).

14. The method according to claim 1 or claim 2, wherein one or more of the phosphodiester linkages between the nucleotides in the aptamer have been replaced with a linkage that increases the stability of aptamer.

15. The method according to claim 1, or claim 2, wherein the equilibrium dissociation constant of the binding of the aptamer to the nucleotide is less than 3 μM.

* * * * *